United States Patent
Urano et al.

(10) Patent No.: US 7,664,608 B2
(45) Date of Patent: Feb. 16, 2010

(54) DEFECT INSPECTION METHOD AND APPARATUS

(75) Inventors: Yuta Urano, Yokohama (JP); Akira Hamamatsu, Yokohama (JP); Shunji Maeda, Yokohama (JP); Kaoru Sakai, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 11 days.

(21) Appl. No.: 11/776,572

(22) Filed: Jul. 12, 2007

(65) Prior Publication Data

US 2008/0015802 A1    Jan. 17, 2008

(30) Foreign Application Priority Data

Jul. 14, 2006   (JP)   ............................. 2006-193549
Aug. 4, 2006   (JP)   ............................. 2006-212744

(51) Int. Cl.
   *G01B 9/00*      (2006.01)
   *G06F 19/00*     (2006.01)
(52) U.S. Cl. .................. 702/40; 356/237.1; 356/237.2; 356/237.3; 356/237.4; 356/237.5; 356/364; 356/369; 356/388; 356/390; 356/394; 382/100; 382/141; 382/144; 382/145; 382/149; 702/33; 702/35; 702/187; 702/189
(58) Field of Classification Search .............. 356/237.1, 356/237.2, 237.3, 237.4, 237.5, 337, 338, 356/340, 341, 342, 343, 364, 369, 88, 390, 356/394, 388; 382/100, 141, 144, 145, 149; 702/1, 33, 35, 40, 127, 128, 187, 189
See application file for complete search history.

(56) References Cited

U.S. PATENT DOCUMENTS

| | | | | |
|---|---|---|---|---|
| 4,648,053 A | * | 3/1987 | Fridge | 382/147 |
| 4,893,932 A | * | 1/1990 | Knollenberg | 356/369 |
| 2006/0002604 A1 | * | 1/2006 | Sakai et al. | 382/141 |

FOREIGN PATENT DOCUMENTS

| | | |
|---|---|---|
| JP | 62-089336 | 4/1987 |
| JP | 63-135848 | 6/1988 |
| JP | 01-117024 | 5/1989 |
| JP | 01-250847 | 10/1989 |

(Continued)

OTHER PUBLICATIONS

Kazuhiko Oka; Spectral Polarimetry Using Channel Spectra; O plus E, 2003; pp. 1,248-1,253; vol. 25, No. 11.

(Continued)

*Primary Examiner*—Edward R Cosimano
(74) *Attorney, Agent, or Firm*—Antonelli, Terry, Stout & Kraus, LLP.

(57) ABSTRACT

A pattern inspection apparatus which compares images of regions, corresponding to each other, of patterns that are formed so as to be identical and judges that non-coincident portions in the images are defects. The pattern inspection apparatus is equipped with an image comparing section which plots individual pixels of an inspection subject image in a feature space and detects excessively deviated points in the feature space as defects. Defects can be detected correctly even when the same patterns in images have a brightness difference due to a difference in the thickness of a film formed on a wafer.

26 Claims, 37 Drawing Sheets

FOREIGN PATENT DOCUMENTS

| | | |
|---|---|---|
| JP | 05-264467 | 10/1993 |
| JP | 06-258239 | 9/1994 |
| JP | 06-324003 | 11/1994 |
| JP | 08-210989 | 8/1996 |
| JP | 08-271437 | 10/1996 |
| JP | 2001-005961 | 1/2001 |
| JP | 2004-271470 | 9/2004 |
| JP | 2005-158780 | 6/2005 |
| JP | 2005-321273 | 11/2005 |
| JP | 2006-145305 | 6/2006 |

OTHER PUBLICATIONS

Kazuhiko Oka; Compact complete imaging polarimeter using birefringent wedge prisms; Optics Express, Jun. 30, 2003; pp. 1,510-1,519; vol. 11, No. 13.

Hisao Kikuta, et al.; Polarization Image Measuring System; O plus E, 2003; pp. 1,241-1,247; vol. 25, No. 11.

* cited by examiner

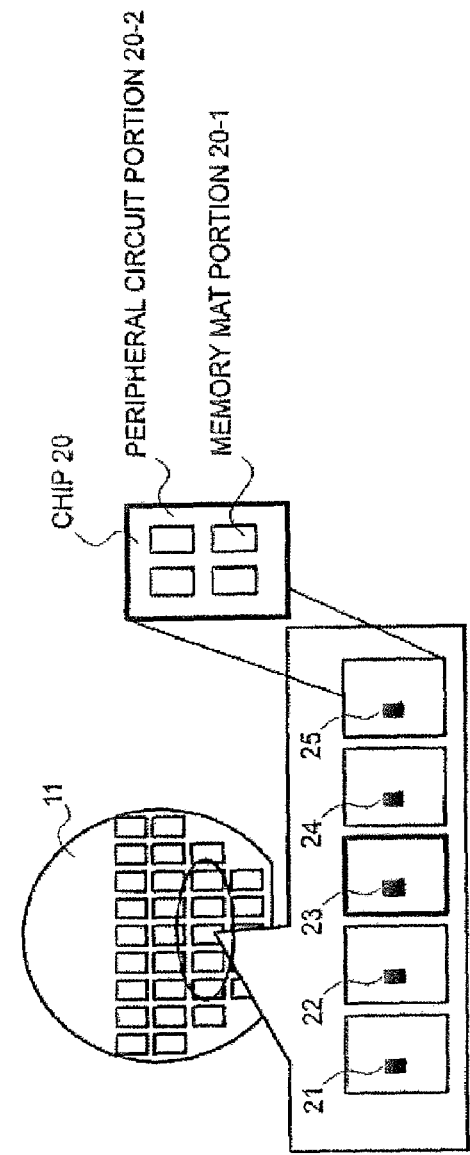

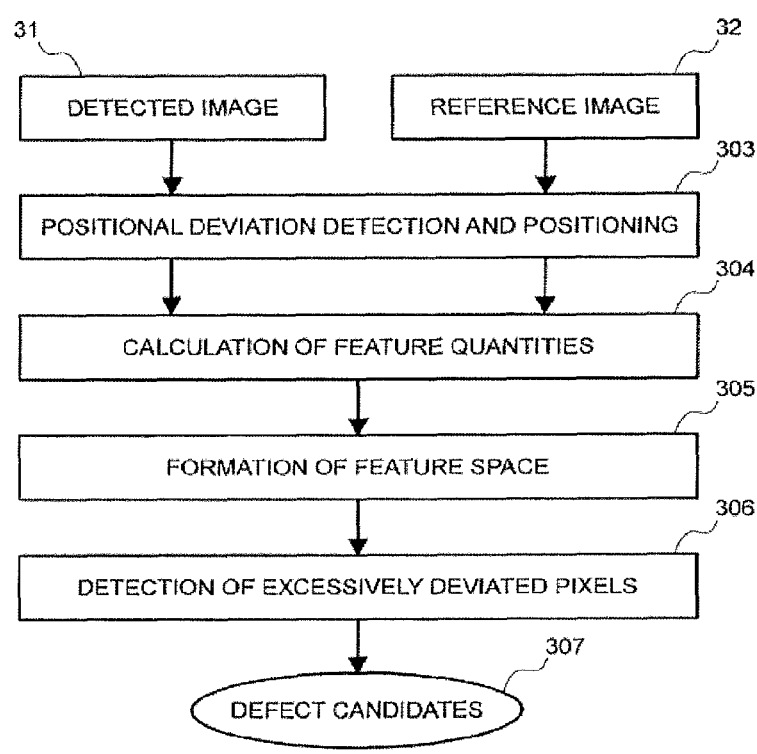

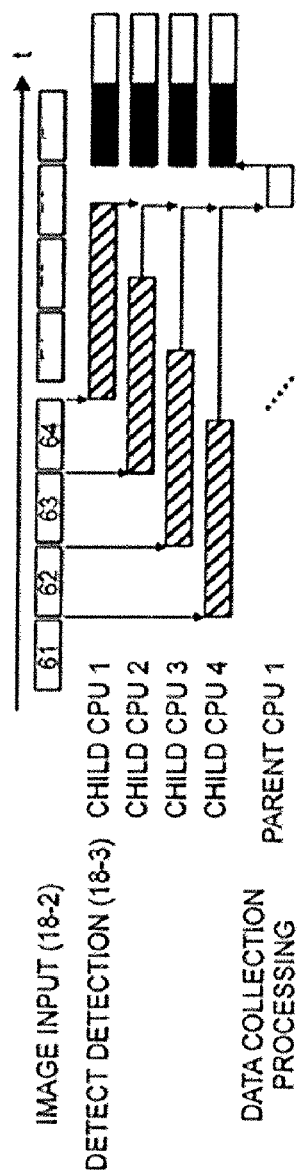

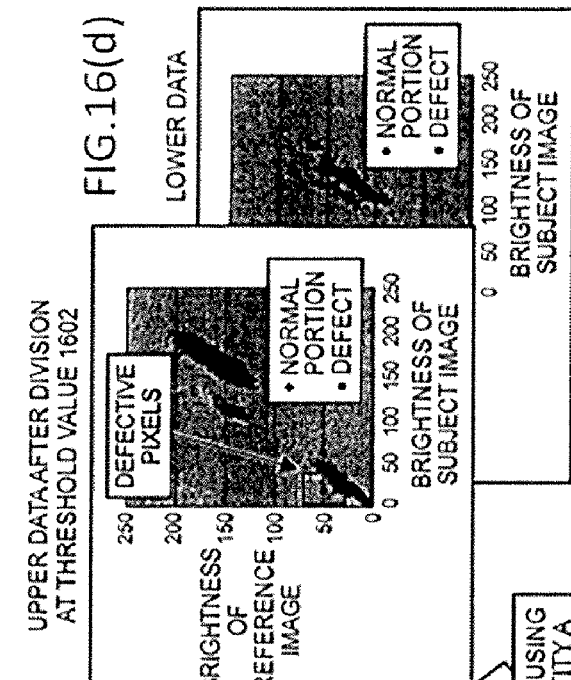
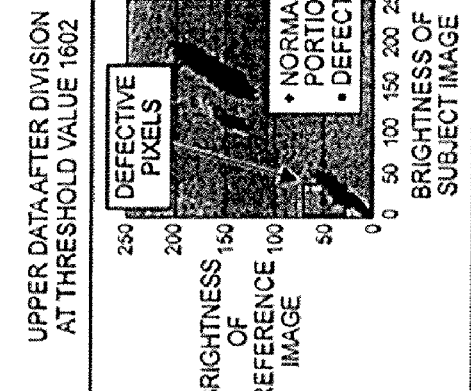
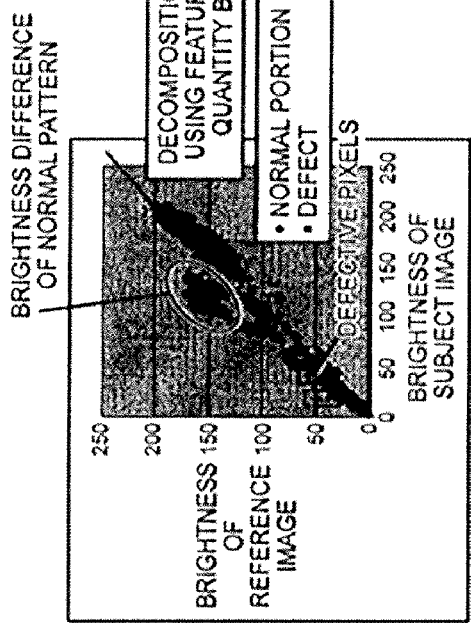
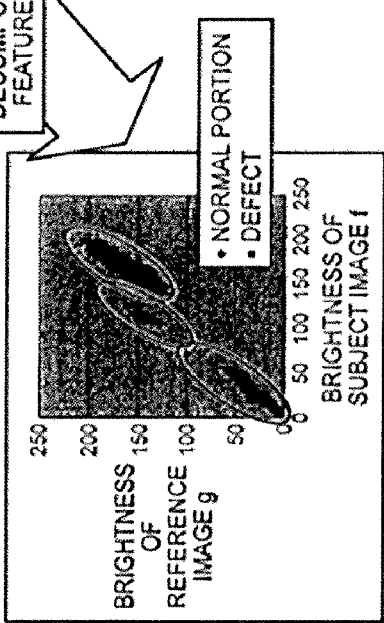
FIG.16(a) FIG.16(b) FIG.16(c) FIG.16(d) FIG.16(e)

FIG.22(a)
FIG.22(b)
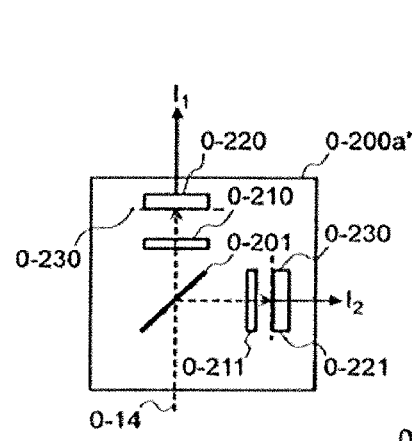
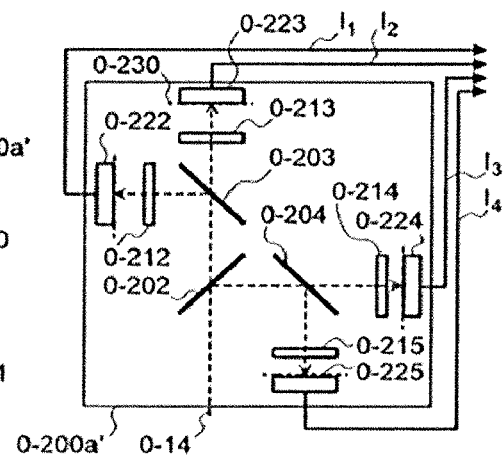
FIG.23(a)
FIG.23(b)
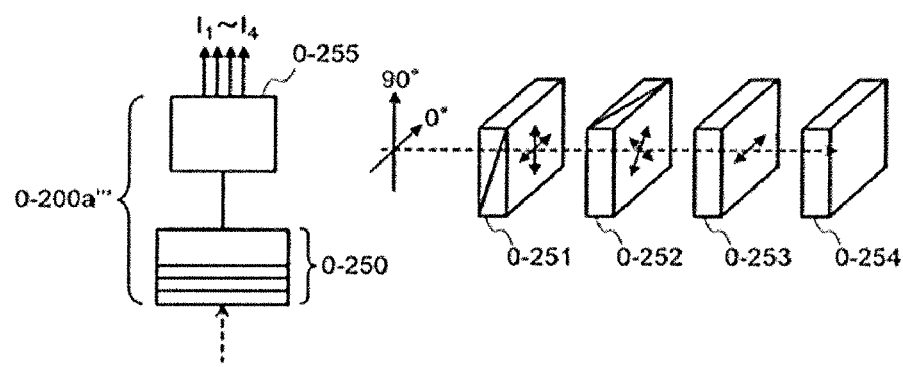

FIG.27(a)
FIG.27(b)
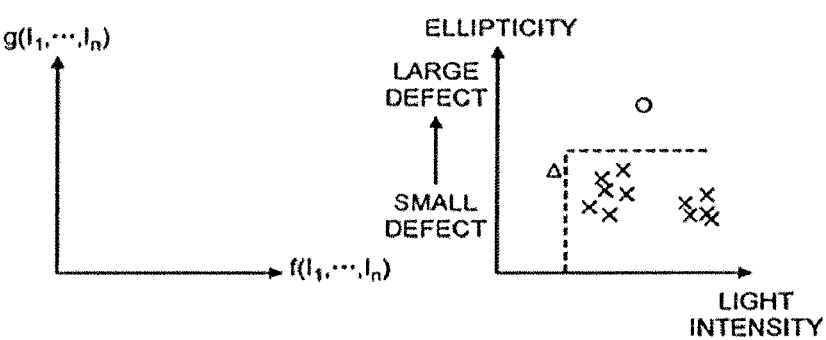
FIG.27(c)
FIG.27(d)
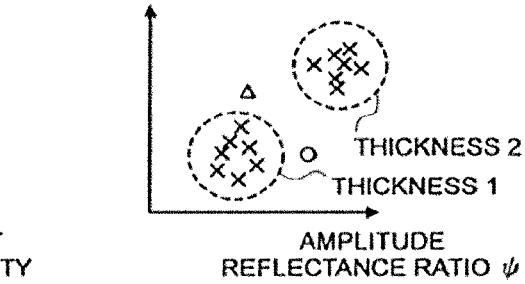

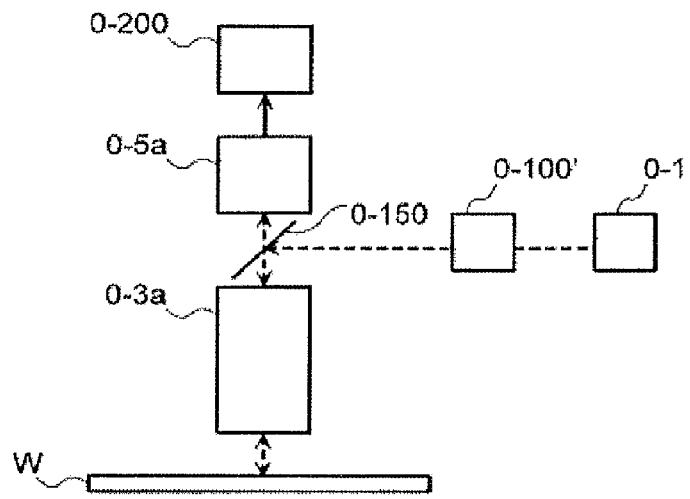
FIG. 33
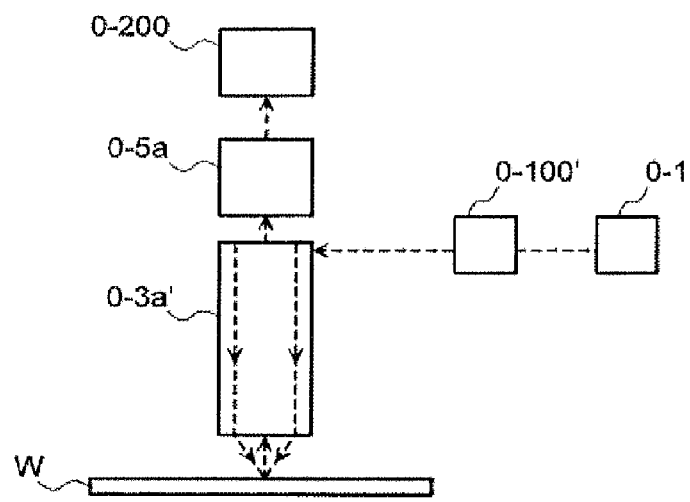
FIG. 34
FIG. 35
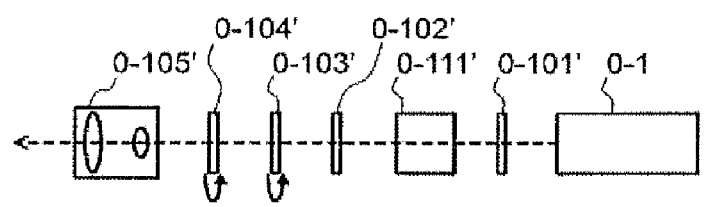

FIG.38(a) FIG.38(b)
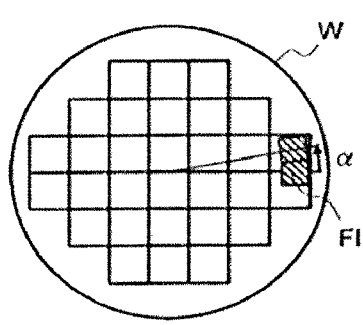 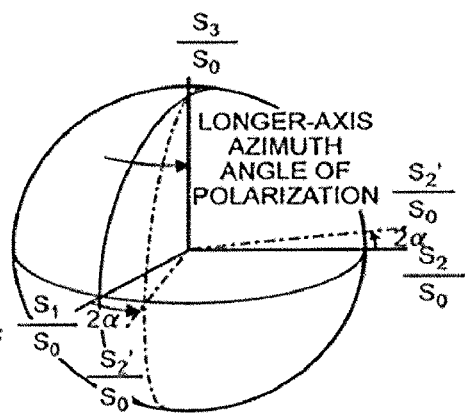
FIG.39
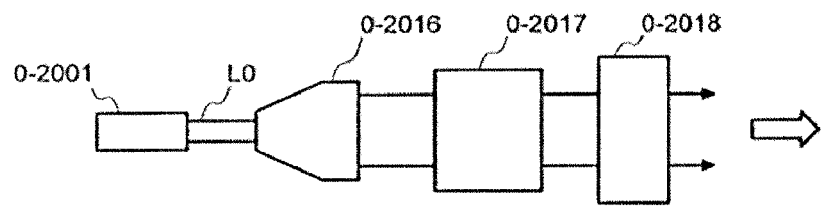

| | | P POLARIZATION |
|---|---|---|
| | | S POLARIZATION |
| | | P+S |
| O | : | ELLIPTICAL POLARIZATION |

DEFECT INSPECTION METHOD AND APPARATUS

BACKGROUND OF THE INVENTION

The invention disclosed in this specification relates to an inspection of comparing an image of a subject obtained by using light, laser light, or an electron beam with a reference image and detecting fine-pattern defects, foreign particles, etc. on the basis of a result of the comparison. In particular, the invention relates to a defect inspection method and apparatus which are suitable for an appearance inspection of semiconductor wafers, TFTs, photomasks, etc.

Among conventional techniques for detecting defects by comparing an inspection subject image with a reference image is a method disclosed in JP-A-5-264467 (Patent document 1).

In this technique, repetitive patterns that are arranged regularly on an inspection subject sample are shot sequentially and each resulting image is compared with an image that has been delayed by a time corresponding to a pattern repetition pitch. Non-coincident portions are detected as defects. This kind of conventional inspection method will be described below by taking, as an example, a defect inspection of a semiconductor wafer. As shown in FIG. 2(a), a number of chips having the same pattern are arranged regularly on a semiconductor wafer as an inspection subject. In memory devices such as DRAMs, each chip can be generally divided into memory mat portions 20-1 and a peripheral circuit portion 20-2. Each memory mat portion 20-1 is a set of small repetitive patterns (cells), and the peripheral circuit portion 20-2 is basically a set of random patterns. In general, in each memory mat portion 20-1, the pattern density is high and an image obtained is dark. On the other hand, in the peripheral circuit portion 20-2, the pattern density is low and an image obtained is bright.

In the conventional pattern inspection, for the peripheral circuit portion 20-2, images of regions located at the same position of adjoining chips are compared with each other; for example, regions 22 and 23 shown in FIG. 2(a) are compared with each other. A portion having a luminance difference that is larger than a threshold value is detected as a defect. In the following, this type of inspection will be referred to as "chip comparison." For each memory mat portion 20-1, images of adjoining cells in the memory mat portion 20-1 are compared with each other. A portion having a luminance difference that is larger than a threshold value is likewise detected as a defect. In the following, this type of inspection will be referred to as "cell comparison." These comparative inspections need to be performed at high speed.

JP-A-2001-5961 (Patent document 2) discloses a defect inspection apparatus which performs, in parallel, positional deviation detection and positional deviation correction and comparative image processing on multi-channel image signals received from an image sensor in parallel and multi-channel reference image signals obtained from a delay circuit section.

JP-A-2004-271470 (Patent document 3) discloses a pattern inspection apparatus which processes images at a processing speed that is approximately the same as an image capturing speed of an image sensor by performing, in the form of parallel processing, positional deviation correction, brightness correction, and defect detection on images taken by the image sensor and captured.

JP-A-2005-158780 (Patent document 4) discloses a pattern defect inspection apparatus in which pieces of image acquisition processing are performed in parallel for plural inspection areas on a sample by using plural image sensors and defects are detected by processing acquired images and classified asynchronously with the image acquisition.

JP-A-2005-321237 (Patent document 5) discloses a pattern inspection apparatus which is equipped with plural detection optical systems, plural image comparison processing means corresponding to the respective detection optical systems, and a classification processing means and which thereby detects a variety of detects with high sensitivity.

On the other hand, the invention disclosed in this specification relates to a defect inspection method and apparatus for inspecting a situation of occurrence of defects such as foreign particles in a manufacturing process. The defect inspection method and apparatus detect defects such as foreign particles occurring in a manufacturing process for producing a subject by forming patterns on a substrate such as a semiconductor manufacturing process, a liquid crystal display device manufacturing process, or a printed circuit board manufacturing process, and take a proper countermeasure by analyzing the defects.

In conventional semiconductor manufacturing processes, foreign particles existing on a semiconductor substrate (inspection subject substrate) may cause a failure such as an interconnection insulation failure or short-circuiting. If minute foreign particles exist on a semiconductor substrate bearing very fine semiconductor devices, the foreign particles may cause a capacitor insulation failure or breakage of a gate oxide film or the like. Such foreign particles exist in various states after being mixed in various manners; for example, they are generated from a movable portion of a transport apparatus or from human bodies, are generated through reaction involving a process gas in a processing apparatus, or are ones originally mixed in chemicals or materials.

Likewise, in conventional liquid crystal display device manufacturing processes, if a certain defect occurs because of a foreign particle placed on a pattern, the liquid crystal display device is rendered not suitable for use as a display device. The same is true of printed circuit board manufacturing processes. Mixing of foreign particles is a cause of pattern short-circuiting or a connection failure. One conventional technique for detecting such foreign particles on a semiconductor substrate is disclosed in JP-A-62-89336 (Conventional technique 1). In this technique, laser light is applied to a semiconductor substrate and scattered light which comes from foreign particles if they are attached to the semiconductor substrate is detected. A detection result is compared with one obtained immediately before for a semiconductor substrate of the same type. This prevents false judgments due to patterns and enables a high-sensitivity, high-reliability foreign particle/defect inspection. JP-A-63-135848 (Conventional technique 2) discloses a technique in which laser light is applied to a semiconductor substrate and scattered light which comes from foreign particles if they are attached to the semiconductor substrate is detected. The detected foreign particles are analyzed by laser photoluminescence, secondary X-ray analysis (XMR), or the like.

Among techniques for detecting foreign particles is a method which detects non-repetitive foreign particles or defects in an emphasized manner by illuminating an inspection subject substrate with coherent light and eliminating, with a spatial filter, light that is emitted from repetitive patterns on the inspection subject substrate.

JP-A-1-117024 (Conventional technique 3) discloses a foreign particle inspection apparatus in which light is applied to circuit patterns formed on an inspection subject substrate from a direction that is inclined by 45° from major straight lines of the circuit patterns, whereby 0th-order diffraction light is prevented from entering the opening of an objective lens. JP-A-117024 refers to interruption of light coming from other straight lines (which are not the major ones) with a spatial filter.

Conventional techniques relating to apparatus and methods for inspecting a subject for defects such as foreign particles are disclosed in JP-A-1-250847 (Conventional technique 4), JP-A-6-258239 (Conventional technique 5), JP-A-6-324003 (Conventional technique 6), JP-A-8-210989 (Conventional technique 7), and JP-A-8-271437 (Conventional technique 8).

JP-A-2006-145305 (Conventional technique 9) discloses a surface inspection apparatus which finds the thickness and the properties of a thin film formed on an inspection subject substrate by detecting plural polarization components simultaneously.

Among techniques for detecting plural polarization components simultaneously are polarimetry using channel spectra which is disclosed in Kazuhiko Oka, "Spectral Polarimetry Using Channel Spectra," O plus E, Vol. 25, No. 11, p. 1,248, 2003 (Non-patent document 1), polarimetry using birefringent wedges which is disclosed in Non-patent document 1 and K. Oka, "Compact Complete Imaging Polarimeter Using Birefringent Wedge Prisms," Optics Express, Vol. 11, No. 13, p. 1,510, 2003 (Non-patent document 2), and polarimetry using amplitude-division prisms and polarimetry using a minute polarizing element array which are disclosed in Hisao Kikuta et al., "Polarization Image Measuring System, O plus E, Vol. 25, No. 11, p. 1,241, 2003 (Non-patent document 3).

SUMMARY OF THE INVENTION

In a semiconductor wafer as an inspection subject, patterns of even adjoining chips have slight differences in film thickness and images of those chips have local brightness differences. If a portion where the luminance difference is larger than a particular threshold value TH is judged a defect as in the conventional method disclosed in Patent document 1, such regions having brightness differences due to differences in film thickness are detected as defects. However, these portions should not be detected as defects; that is, this is a false judgment. One method that has been employed to avoid such a false judgment is to set the threshold value for defect detection large. However, this lowers the sensitivity and makes it unable to detect defects whose difference values are approximately equal to the threshold value. Brightness differences due to differences in film thickness may occur between particular chips among the chips arranged on a wafer as shown in FIG. 2(a), for example, or between particular patterns in a certain chip. Where the threshold value is set for such local areas, the total inspection sensitivity is made very low.

Another factor in lowering the sensitivity is a brightness difference between chips due to pattern thickness variation. In conventional brightness-based comparative inspections, such brightness variation causes noise during an inspection.

On the other hand, there are many types of defects and they are generally classified into defects that need not be detected (i.e., defects that can be regarded as noise) and defects that should be detected. Although appearance inspections are required to extract defects desired by a user from an enormous number of defects, it is difficult to satisfy this requirement by the above-mentioned comparison between luminance differences and a threshold value. In this connection, in many cases, the appearance depends on the defect type, more specifically, the combination of inspection-subject-dependent factors such as the material, surface roughness, size, and depth and detection-system-dependent factors such as illumination conditions.

Patent documents 2-4 disclose the techniques for processing, in parallel, images acquired by an image sensor(s) However, there references do not refer to a configuration capable of flexibly accommodating, without lowering the processing speed or detection sensitivity, even a case that the appearance varies depending on the defect type.

Patent document 5 discloses the apparatus which is equipped with plural detection optical systems and can detect a variety of defects with high sensitivity. However, this reference does not refer to a configuration capable of flexibly accommodating, without lowering the processing speed or detection sensitivity, even a case that the appearance varies depending on the defect type.

The aspect of the invention for solving the above-described first problems of the conventional inspection techniques relates to a pattern inspection apparatus which compares images of regions, corresponding to each other, of patterns that are formed so as to be identical and judges that non-coincident portions of the image are defects. This aspect of the invention is intended to realize a defect inspection which can reduce brightness unevenness between comparison images due to differences in film thickness, differences in pattern thickness, or the like and can detect, keeping high processing speed and high sensitivity, defects desired by a user that are buried in noise or defects that need not be detected in such a manner as to flexibly accommodate even a case that the appearance varies depending on the defect type.

In a pattern inspection apparatus which compares images of regions, corresponding to each other, of patterns that are formed so as to be identical and judges that non-coincident portions of the image are defects, this aspect of the invention makes it possible to lower the influence of brightness unevenness between comparison images due to differences in film thickness, differences in pattern thickness, or the like and to enable a high-sensitivity defect inspection merely by simple parameter setting.

This aspect of the invention allows a defect inspection apparatus to perform a high-sensitivity defect inspection capable of accommodating a variety of defects by calculating feature quantities of pixels of comparison images and employing, as defect candidates, pixels having excessively deviated values in a feature space.

This aspect of the invention also makes it possible to increase the number of detectable defect types and detect various defects with high sensitivity by unifying, at each stage, pieces of information that are output from plural detection systems. With the above-described features, this aspect of the invention makes it possible to detect fatal defects with high sensitivity even in the case where the inspection subject is a semiconductor wafer and brightness differences occur between the same patterns of images due to differences in film thickness in a wafer.

Furthermore, this aspect of the invention enables high-speed, high-sensitivity defect inspection in which pieces of processing can be assigned to CPUs freely by employing, for a defect detection processing section, a system configuration comprising a parent CPU, plural child CPUs, and oppositely-directed data transfer buses.

On the other hand, Conventional techniques 1-8 have a problem that in an irregular circuit pattern portion a signal representing a defect is overlooked because of scattered light from the pattern and the sensitivity is thereby lowered.

Conventional technique 9 is intended to find the thickness and the properties of a thin film and does not directly contribute to increase of the sensitivity of defect detection.

The aspect of the invention for solving the above-described second problems of the conventional inspection techniques is intended to provide a defect inspection apparatus and method capable of detecting, at high speed with high accuracy, defects on an inspection subject substrate having patterns that emit scattered light that is approximately the same in intensity as emitted by defects.

This aspect of the invention relates to a defect inspection apparatus having an illumination optical system for guiding light emitted from a light source to a prescribed region on an inspection subject substrate in such a manner that the light is given a prescribed polarization state, a detection optical system for guiding reflection-scattered light coming from the prescribed region in a prescribed azimuth angle range and a prescribed elevation range to a photodetector and converting it into an electrical signal, and a defect judging section for extracting defect-indicative signals from the electrical signal. According to this aspect of the invention, the detection optical system has a polarization detecting means for detecting plural different polarization components independently and producing plural signals corresponding to the respective polarization components. The defect judging section extracts defect-indicative signals on the basis of a distribution of the terminal points of vectors corresponding to the above-mentioned plural signals in a space that is defined by axes that are represented by the above-mentioned respective polarization components or physical quantities calculated from them.

These and other objects, features, and advantages of the invention will be apparent from the following more particular description of preferred embodiments of the invention, as illustrated in the accompanying drawings.

BRIEF DESCRIPTION OF THE DRAWINGS

FIG. 2(a) is a plan view of a semiconductor wafer and an enlarged view of a chip row, and FIG. 2(b) is an enlarged view of a chip;

FIG. 3 is a flowchart showing the procedure of a defect candidate extraction process;

FIG. 7 shows a timing relationship of pieces of processing performed by respective CPUs in the case where the chip is inspected according to a further parallel process;

FIG. 16(b) is a scatter diagram formed from the entire subject image, FIG. 16(c) is a scatter diagram of the pixels contained in an upper-half area obtained by dividing the feature space of FIG. 16(a) at a threshold value 1602, FIG. 16(d) is a scatter diagram of the pixels contained in a lower-half area obtained by dividing the feature space of FIG. 16(a) at the threshold value 1602, and FIG. 16(e) is a scatter diagram showing pixel groups corresponding to areas obtained by subdividing the upper-half area obtained by dividing the feature space of FIG. 16(a) at the threshold value 1602;

FIGS. 22(a) and 22(b) show general configurations of polarization detecting sections according to the third embodiment which are implemented by the amplitude division method;

FIGS. 23(a) and 23(b) show a general configuration of a polarization detecting section using birefringent wedges according to the third embodiment;

FIGS. 27(a)-27(d) are conceptual diagrams showing a defect judging method based on two physical quantities calculated from plural different polarization component signals which is employed by the signal processing section according to the third embodiment;

FIG. 33 shows a general configuration of an optical system of a second modification of the defect inspection apparatus according to the third embodiment;

FIG. 34 shows a general configuration of an optical system of a third modification of the defect inspection apparatus according to the third embodiment;

FIG. 35 shows a general configuration of an illumination optical system used in the second, third, fourth, and fifth modifications of the defect inspection apparatus according to the third embodiment;

FIGS. 38(a) and 38(b) are conceptual diagrams showing rotation of a field of view and rotation of a detected polarization component with respect to an inspection subject substrate in the fourth and fifth modifications of the defect inspection apparatus according to the third embodiment;

FIG. 39 is a side view of a beam expanding optical system according to a fourth embodiment of the invention for solving the second problems;

DESCRIPTION OF THE PREFERRED EMBODIMENTS

Embodiments of the present invention for solving the first problems will be hereinafter described with reference to FIG. 1, FIG. 2(a), FIG. 2(b), FIG. 3, FIG. 4(a), FIG. 4(b), FIG. 4(c), FIG. 5(a), FIG. 5(b), FIG. 5(c), FIG. 6(a), FIG. 6(b), FIG. 6(c), FIG. 6(d), FIG. 7, FIG. 8(a), FIG. 8(b), FIG. 8(c), FIG. 9, FIG. 10(a), FIG. 10(b),FIG. 11, FIG. 12(a), FIG. 12(b), FIG. 13, FIG 14(a), FIG. 14(b), FIG. 15, FIG. 16(a), FIG. 16(b), FIG. 16(c), FIG. 16(d), FIG. 16(e), 17(a), FIG. 17(b), FIG. 18, FIG. 19(a) and FIG. 19(b).

Embodiment 1 of the Invention for Solving the First Problems

Figure 1:
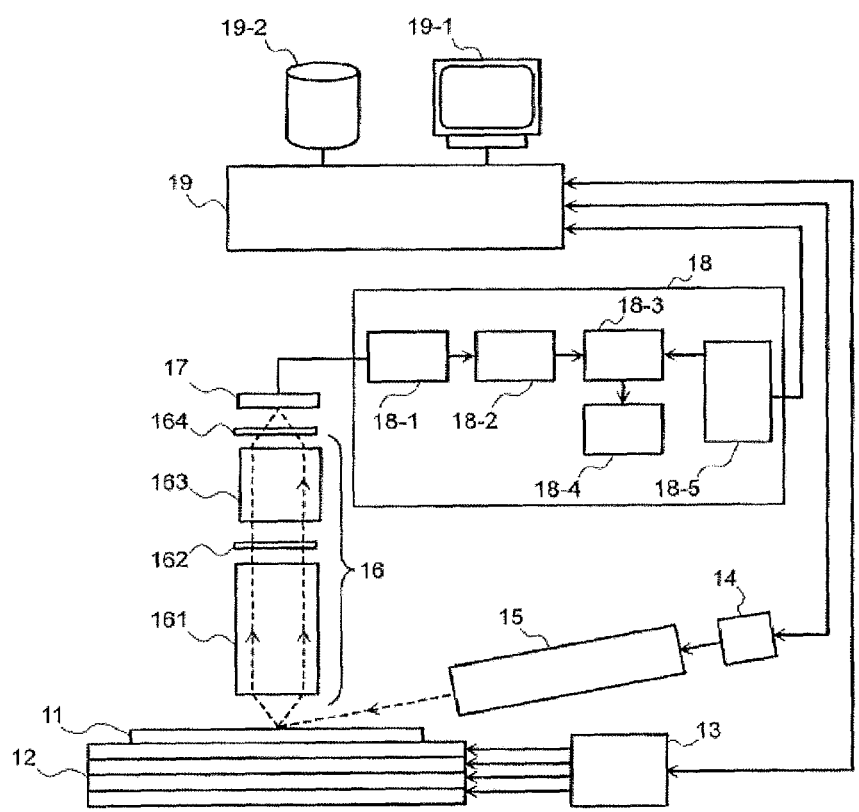
FIG. 1 is a front view showing a general configuration of an inspection apparatus according to a first embodiment of the invention for solving the first problems.

A first embodiment will be described below which is a defect inspection method employed by a defect inspection apparatus for semiconductor wafers which uses dark-field illumination. FIG. 1 shows the configuration of an exemplary defect inspection apparatus using dark-field illumination. Symbol 11 denotes a sample (an inspection subject such as a semiconductor wafer), symbol 12 denotes a stage capable of being moved and rotated in the XY-plane and being moved in the Z-direction (height direction) while being mounted with the sample 11, and symbol 13 denotes a mechanical controller for driving the stage 12. Symbol 14 denotes a light source for emitting laser light and symbol 15 denotes an illumination optical system. Laser light emitted from the light source 14 is applied to the sample 11 via the illumination optical system 15. Scattered light coming from the sample is 11 image-formed by an upper detection system 16, and a resulting optical image is received by and converted into an image signal by an image sensor 17. The sample 11 is mounted on the X-Y-Z-θ stage 12 and foreign-particle-scattered light is detected while the X-Y-Z-θ stage 12 is moved horizontally, whereby detection results can be obtained in the form of a two-dimensional image.

The upper detection system 16 is composed of an objective lens 161 for gathering scattered light coming from the sample 11, a spatial filter 162 for interrupting diffraction light patterns which are formed at a pupil position of the objective lens 161 or a position equivalent to it because of fine-pitch repetitive patterns formed on the sample 11, an image-forming lens 163 for forming an optical image of scattered light that originates from the sample 11 and passes through the spatial filter 162, and an optical filter 164 such as a polarizing filter or an ND filter.

Although in the example of FIG. 1 the light source 14 is a laser, ultraviolet light (UV light) may be used to increase the resolution of a detected image (i.e., to detect finer defects). Where a single-wavelength laser is used as the light source 14, the detection sensitivity can be increased by reducing noise in a detected image by inserting a means for lowering the coherence (not shown; a means for averaging, temporally and spatially, speckle noise occurring on the image detection surface when a short-wavelength laser is used, the means using optical filters having different optical path lengths as disclosed in JP-A-2000-193443, for example) inside the illumination optical system 15 or between the light source 14 and the illumination optical system 15.

The image sensor 17 is a one-dimensional sensor such as a CCD. Instead of a CCD, a time delay integration image sensor (TDI image sensor) may be used in which plural one-dimensional image sensors are arranged two-dimensionally. In this case, a two-dimensional image can be obtained with high sensitivity at a relatively high speed by transferring a signal detected by each one-dimensional image sensor to the next-stage one-dimensional image sensor in synchronism with movement of the stage 12 and conducting signal addition. Using a parallel-output-type sensor having plural output taps as the TDI image sensor makes it possible to process outputs of the sensor in parallel and thereby enables even higher detection. Furthermore, if a back-illumination-type sensor is used as the image sensor 17, the detection efficiency can be made higher than in the case where a front-illumination-type sensor is used.

Symbol 18 denotes an image comparison processing section for extracting defect candidates in the sample 11 (wafer), which is composed of a pre-processing section 18-1 for performing image corrections such as a shading correction and a dark level correction on a detected image signal, an image memory 18-2 for storing a digital signal of a corrected image, a defect detecting section 18-3 for extracting defect candidates by comparing images of corresponding regions stored in the image memory 18-2, a classifying section 18-4 for classifying detected defects into plural defect types, and a parameter setting section 18-5 for setting image processing parameters.

With the above configuration, first, digital signals of an image of an inspection subject region (hereinafter referred to as "detected image") and an image of a corresponding region (hereinafter referred to as "reference image") that have been corrected by the pre-processing section 18-1 and are stored in the image memory 18-2 are read out by the defect detecting section 18-3, which then calculates correction values for positioning. Then, the defect detecting section 18-3 positions the detected image and the reference image with respect to each other using the position correction values, and outputs, as detect candidates, pixels having excessively deviated values in a feature space using feature quantities of corresponding pairs of pixels. The parameter setting section 18-5 sets image processing parameters which are input externally such as feature quantity types and threshold values to be used in extracting defect candidates, and supplies those to the defect detecting section 18-3. The defect classifying section 18-4 extracts true defects on the basis of the feature quantities of respective defect candidates and classifies those.

Symbol 19 denotes a total control section which incorporates a CPU for performing various controls. The total control section 19 is connected to a user interface section 19-1 having a display means and an input means through which to receive, from a user, an instruction of alterations to inspection parameters (e.g., feature quantity types and threshold values which are used for extraction of excessively deviated values) and to display detected defect information and a storage device 19-2 for storing feature quantities of detected defect candidates, images, etc. The mechanical controller 13 drives the stage 12 according to a control command from the total control section 19. The image comparison processing section 18, the optical systems, etc. are also driven according to control commands from the total control section 19.

As shown in FIGS. 2(a) and 2(b), the semiconductor wafer 11 as an inspection subject is such that a number of chips 20 which have the same patterns and each of which consists of the memory mat portions 20-1 and the peripheral circuit portion 20-2 are arranged regularly. The total control section 19 moves the semiconductor wafer 11 (sample) continuously together with the stage 12 and, in synchronism with this, captures chip images sequentially from the image sensor 17. The total control section 19 compares a digital image signal of a detected image (e.g., an image of a region 23 in FIG. 2(a)) with that of a reference image (e.g., an image of one of region 21, 22, 24, and 25 located at the same position as the region 23 in the regularly arranged chips) according to the above-described procedure, and detects, as defect candidates, pixels that are judged statistically as having excessively deviated values.

FIG. 3 is a flowchart of an exemplary process which is executed by the defect detecting section 18-3 for an image of the region 23 of the inspection subject chip shown in FIG. 2(a). First, an image (detected image 31) of the region 23 of the inspection subject chip and a corresponding reference image 32 (assumed here to be an image of the region 22 of the adjacent chip shown in FIG. 2(a)) are read from the image memory 18-2, a positional deviation is detected, and positioning is performed (step 303).

At step 304, plural feature quantities are calculated for each pixel of the detected image 31 that has been subjected to the positioning and the corresponding pixel of the reference image 32. Each feature quantity may be a quantity representing a feature of each pixel. Exemplary feature quantities are (1) brightness, (2) contrast, (3) density difference, (4) brightness variance of nearby pixels, (5) correlation coefficient, (6) brightness increase or decrease from nearby pixels, and (7) second-order differential coefficient. Part of these feature quantities are given by the following equations, where $f(x, y)$ represents the brightness of each pixel of the detected image and $g(x, y)$ represents the brightness of the corresponding pixel of the reference image:

Brightness: $f(x, y)$ or $\{f(x, y)+g(x, y)\}/2$

Contrast: $\max\{f(x, y), f(x+1, y), f(x, y+1), f(x+1, y+1)\} - \min\{f(x, y), f(x+1, y), f(x, y+1), f(x+1, y+1)\}$ Density difference: $f(x, y)-g(x, y)$ Variance: $[\Sigma\{f(x+i, y+j)^2\}-\{\Sigma f(x+i, y+j)\}^2/M]/(M-1)$
$(i, j=-1, 0, 1; M=9)$ At step 305, a feature space is formed by plotting pixels in the space having, as axes, some or all of the feature quantities. At step 306, pixels that are located outside a major data distribution in the feature space, that is, pixels whose feature quantities are deviated excessively, are detected. At step 307, defect candidates are extracted.

Figure 4A:
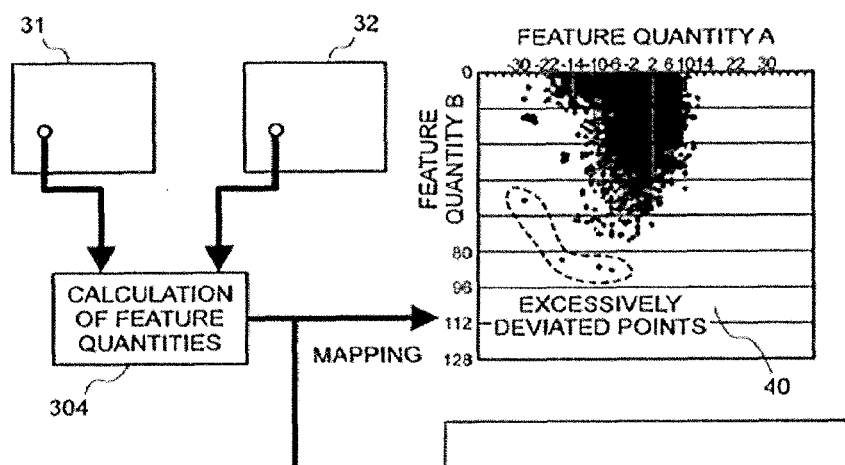
FIG. 4(a) shows a procedure of detection of excessively deviated pixels in a feature space.

In FIG. 4(a), symbol 40 denotes a feature space which is formed by calculating feature quantities from corresponding pairs of pixels of the detected image 31 and the reference image 32 and plotting the pixels in a two-dimensional space having, as axes, feature quantities A and B among those feature quantities. In the feature space 40, points enclosed by a broken line are located outside a dense data distribution and indicate pixels having excessively deviated values. In FIG. 4(a), symbol 41 denotes an imagery diagram of an N-dimensional feature space formed by calculating feature quantities from corresponding pairs of pixels of the detected image 31 and the reference image 32 and plotting the pixels in an N-dimensional space having, as axes, N feature quantities among those feature quantities. Detecting excessively deviated points in the N-dimensional feature space 41 makes it possible to detect defects from a variety of noises in a manner that more relies on the feature quantities.

Figure 4B:
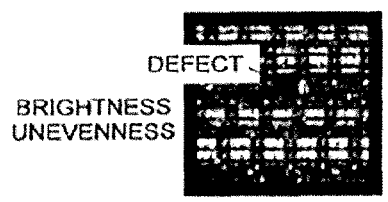
FIG. 4(b) shows an image having defects and brightness unevenness.
Figure 4C:
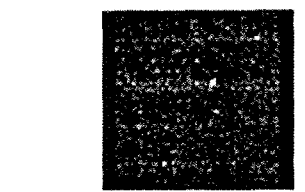
FIG. 4(c) shows an image in which defects are extracted.

FIG. 4(b) shows a difference image in which brightness differences between the detected image 31 and the reference image 32 are shown in a scale of values 0 to 255. The pixel is shown more brightly when the difference is larger. In FIG. 4(b), in addition to defects that are enclosed by white circles, normal patterns have large differences (i.e., the two images are different in brightness there) and are named "brightness unevenness" in FIG. 4(b). This kind of brightness unevenness is also detected together with real defects in the conventional method in which a portion where the brightness difference between the images is larger than a threshold value is detected as a defect. FIG. 4(c) shows an exemplary distance image in which distances from the center of the dense data distribution in the feature space 41 are shown in a scale of values 0 to 255. In FIG. 4(c), only defects having excessively deviated values (enclosed by white circles) are shown brightly, which indicates that the brightness unevenness is suppressed and only detects are detected. In this manner, detecting excessively deviated values of the feature quantities in a space defined by plural feature quantities makes it possible to suppress a variety of noises of normal patterns and detect only defects.

Although in the above-described example the reference image is the image of the adjacent chip (the image of the region 22 in FIG. 2(a)), it may be a composed image (average values, median values, or the like) that are calculated from images of plural chips (images of the regions 21, 22, 24, and 25 in FIG. 2(a) that are located at the corresponding positions).

Figure 5A:
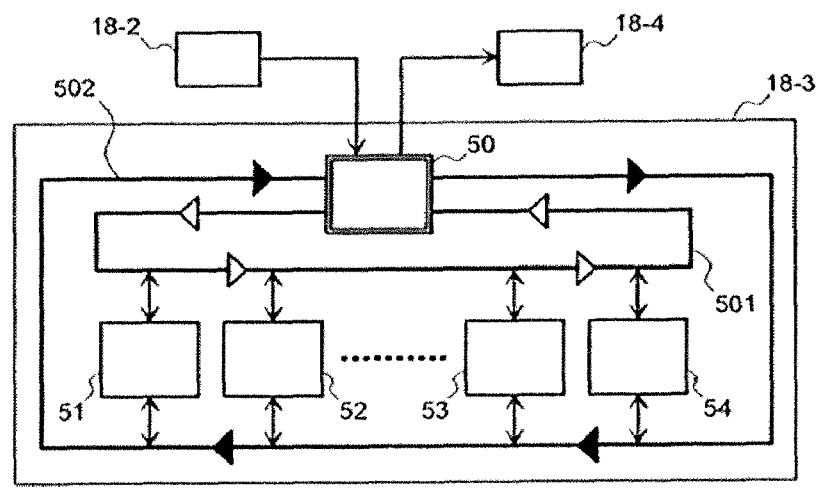
FIG. 5(a) is a block diagram showing a CPU arrangement according to the first embodiment for a defect detection process.

FIG. 5(a) shows the system configuration of the defect detecting section 18-3 of the image comparison processing section 18. As shown in FIG. 5(a), the image processing system which performs defect detection has plural computation CPUs 50-54. Among the computation CPUs 50-54, the computation CPU 50 is a CPU which performs the same or greater computations as or than the other computation CPUs 51-54 and also performs image data transfer to the other computation CPUs 51-54, commanding of execution of computations, data exchange with the outside, and other operations. The computation CPU 50 will be hereinafter referred to as "parent CPU 50." The other computation CPUs 51-54 (hereinafter referred to as "child CPUs 51-54") receive commands from the parent CPU 50 and perform computations, data exchange with themselves, and other operations. Buses for data communication from the parent CPU 50 to the child CPUs 51-54 are buses that allow bidirectional data flows, that is, one or more counterclockwise buses 501 (child CPU 51→52→ . . . →53→54) and one or more clockwise buses 502 (child CPU 54→53→ . . . →52→51). The child CPUs 51-54 can exchange data via either a clockwise or counterclockwise bus.

Figure 5B:
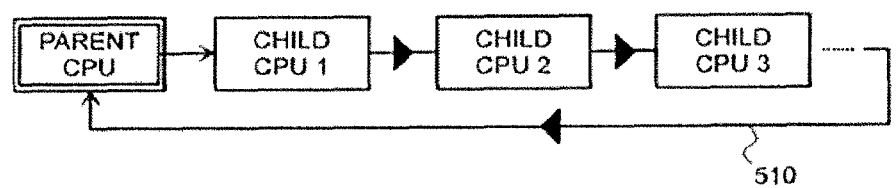
FIG. 5(b) is a block diagram showing a conventional CPU arrangement for a defect detection process.
Figure 5C:
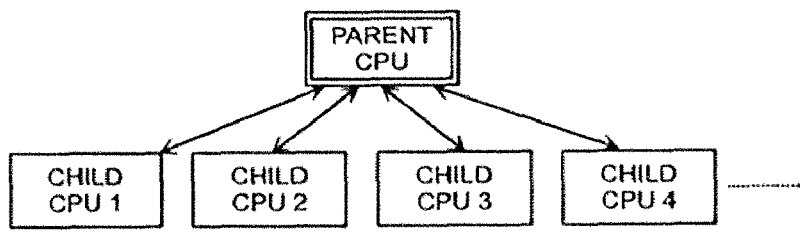
FIG. 5(c) is a block diagram showing another conventional CPU arrangement for a defect detection process.

Advantages of this configuration will be described below in comparison with conventional ones. FIG. 5(b) shows a typical conventional system configuration. A data communication bus 510 allows data to flow between child CPUs only in one direction. Therefore, a computation result of the child CPU 3 cannot be fed back to the child CPU 1. Furthermore, to pass data from the parent CPU to the child CPU, the data need to go through the child CPUs 1 and 2. Therefore, data exchange between the parent CPU and a child CPU that is distant from the parent CPU takes longer time as the number of child CPUs increases. FIG. 5(c) shows another typical conventional method. Each child CPU can exchange data directly with the parent CPU. However, data exchange between child CPUs takes time because it is performed via the parent CPU. In contrast, the configuration according to the embodiment shown in FIG. 5(a) enables fast data exchange both between the parent CPU and a child CPU and between child CPUs.

Figure 6A:
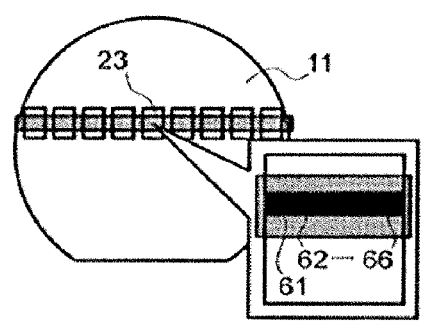
FIG. 6(a) is a plan view of a semiconductor wafer and an enlarged view of a chip.

Next, a process executed by the above system configuration will be described by using, as an example, the image comparison process of FIG. 3. FIG. 6(a) shows an example in which a chip 23 on a semiconductor wafer 11 is an inspection subject and images are input through a sensor. Six input images (inspection subject images) 61-66 are produced from the inspection subject chip 23.

Figure 6B:
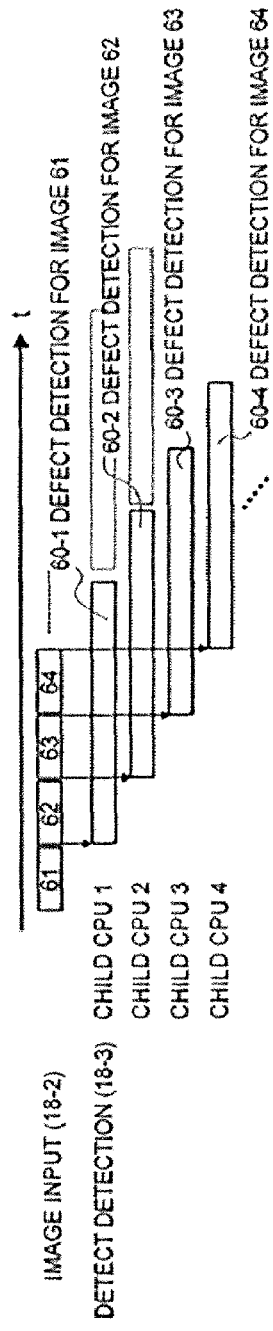
FIG. 6(b) shows a timing relationship of pieces of processing performed by respective CPUs in the case where the chip is inspected according to a general parallel process.

FIG. 6(b) shows a general parallel process which is executed after inspection subject images 61-64 and corresponding reference images are taken and input to the image memory 18-2. The horizontal axis t represents time. Symbols 60-1 to 60-4 denote processing periods during which the child CPUs 1-4 of the defect detecting section 18-3 operate on an image-by-image basis. In this manner, in the ordinary parallel process, upon input of images, the parent CPU assigns them to the child CPUs 1-4 and the child CPUs 1-4 perform the same kinds of processing in parallel. When each of the child CPUs 1-4 has finished a series of processing, the next image is input to it.

Figure 6C:
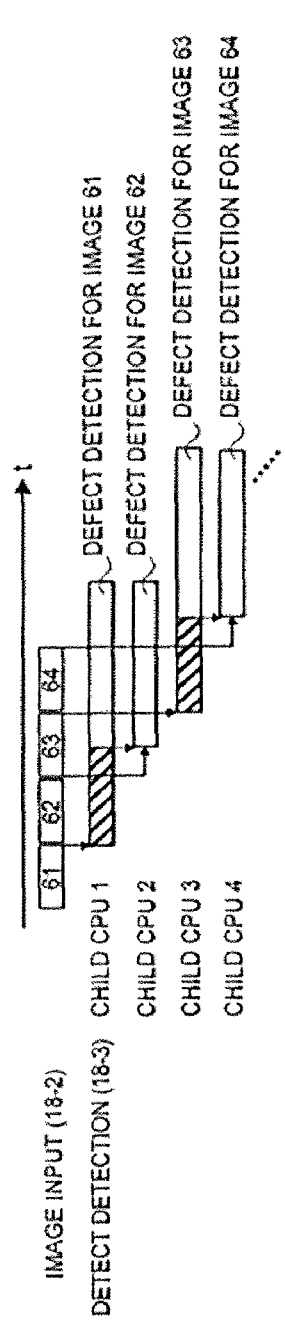
FIG. 6(c) shows a timing relationship of pieces of processing performed by respective CPUs in the case where the chip is inspected according to a parallel process.

FIG. 6(c) shows another exemplary parallel process. If it suffices to execute the first half (in the example of FIG. 3, the positional deviation detection etc. of step 303) of defect detection processing once per two images, as shown in FIG. 6(c) hatched processing portions are performed by the child CPUs 1 and 3 and calculated values (in the example of FIG. 3, positional deviations) are applied to the child CPUs 2 and 4. This makes it possible to increase the processing speed (the processing on the image 62 is finished at the same time as that on the image 61). However, where this process is executed by the conventional system configuration shown in FIG. 5(c), since data transfer from the child CPU 1 to the child CPU 2 is performed via the parent CPU, a communication standby time etc. occur and the processing speed is restricted. In contrast, where the above process is executed by the system configuration according to the embodiment which is shown in FIG. 5(a), since data exchange between child CPUs is performed via a data transfer bus that provides a shorter transfer distance, occurrence of a standby time can be prevented and high-speed processing is enabled.

Figure 6D:
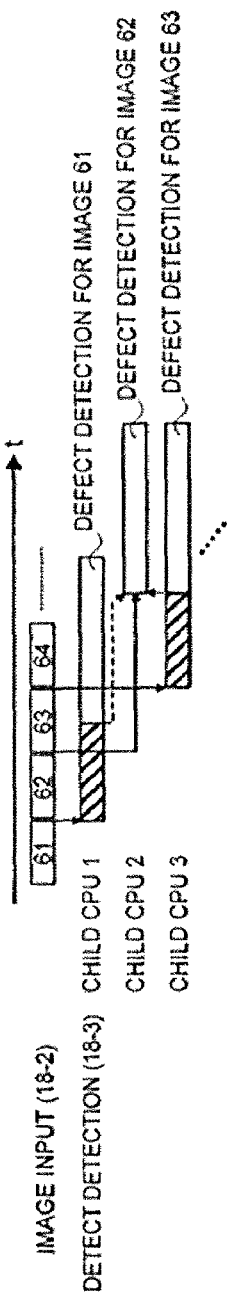
FIG. 6(d) shows a timing relationship of pieces of processing performed by respective CPUs in the case where the chip is inspected according to another parallel process.
Figure 8A:
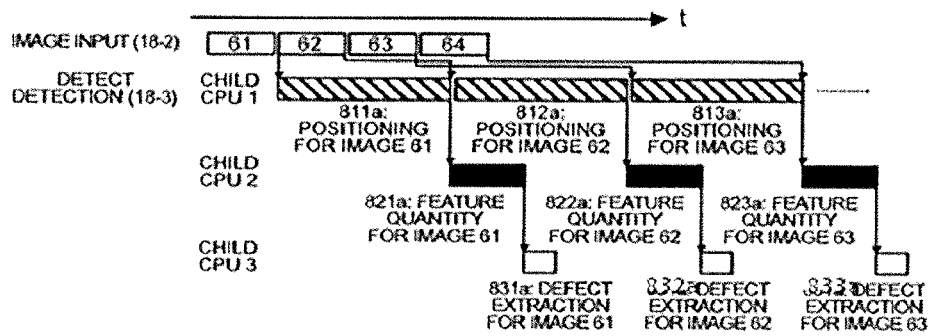
FIG. 8(a) shows a timing relationship of pieces of processing performed by the respective CPUs of the conventional CPU arrangement of FIG. 5(b)
Figure 8B:
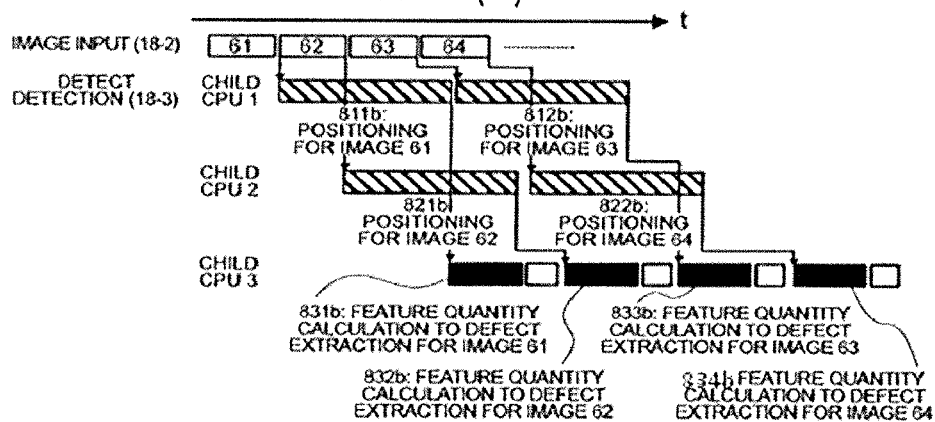
FIG. 8(b) shows a timing relationship of pieces of processing performed by the respective CPUs of the CPU arrangement of FIG. 5(a) according to the first embodiment.
Figure 8C:
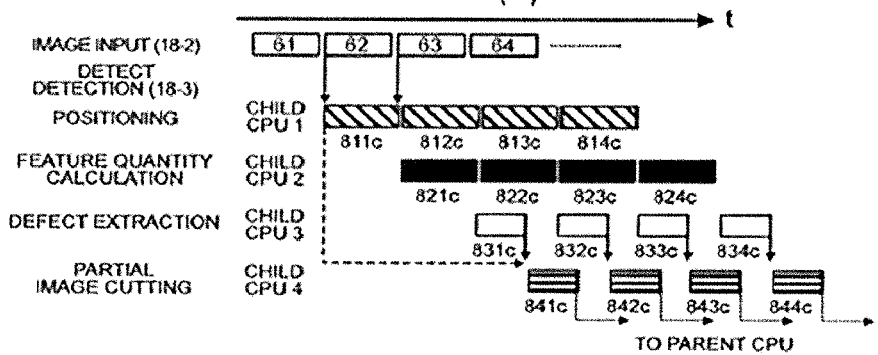
FIG. 8(c) shows a timing relationship of another parallel process which is executed by plural CPUs.

FIG. 6(d) shows still another exemplary parallel process. Interpolation values, average values, or the like of values calculated from the image 61 by the child CPU 1 and values calculated from the image 63 by the child CPU 3 are applied to the first half (corresponds to hatched portions of pieces of defect detection processing performed by the child CPUs 1 and 3) of defect detection processing to be performed on the image 62 by the child CPU 2. Also in this case, where this process is executed by the system configuration according to the embodiment which is shown in FIG. 5(a), since data transfer from the child CPU 1 to the child CPU 2 and data transfer from the child CPU 3 to the child CPU 2 are performed via oppositely directed data transfer buses, occurrence of a standby time can be prevented without requiring a timing control etc. and high-speed processing is enabled.

FIG. 7 shows a further exemplary parallel process. Positional deviation values calculated by the positional deviation detection (the first halves of pieces of defect detection processing; hatched portions) from plural images are collected, and highly reliable positional deviation values are calculated. The images 61-64 are positioned by using the same positional deviation values. Where this process is executed by the system configuration of the second conventional method shown in FIG. 5(*c*), positional deviation values calculated by the child CPUs 1-4 are transmitted to the parent CPU by one-to-one communications. And positional deviation values calculated by the parent CPU after collecting the received values are transmitted to each child CPU by a one-to-one communication. During that course, child CPUs other than one that is performing a communication with the parent CPU are rendered in a communication standby state and the processing speed is lowered by an amount corresponding to standby times. In contrast, where the above process is executed by the system configuration according to the embodiment which is shown in FIG. 5(*a*), the parent CPU sends out positional deviation values calculated after collecting received values via the data transfer buses 501 and 502 of both directions and each child CPU receives the information of the positional deviation values from a data transfer bus that makes the parent CPU closer to it or a free data transfer bus. As a result, almost no communication standby times occur and the parent CPU can exchange data with all the child CPUs simultaneously.

Next, advantages of the system configuration according to the embodiment will be described by using a pipeline process as an example. FIG. 8(*a*) shows an example in which a pipeline process is executed by the system configuration of the first conventional method shown in FIG. 5(*b*) in such a manner that the parent CPU sequentially reads images (in this example, images 61-64) that have been sequentially input to the image memory 18-2 and sends out those to the child CPU 1. In FIG. 8(*a*), pieces of positional deviation detection and positioning processing (step 303) of the defect detection process of FIG. 3 are hatched as pieces of processing 811*a*-813*a* (lengths correspond to processing periods), feature quantity calculations (step 304) and pieces of feature space formation processing (step 305) are shown in black as pieces of processing 821*a*-823*a* (lengths correspond to processing periods), and pieces of defect candidate extraction processing (step 306) are shown in white as pieces of processing 831*a*-833*a* (lengths correspond to processing periods). Pieces of processing of the same kind are assigned to the dedicated one of the child CPUs 1-3, and each of the child CPUs 1-3 performs assigned, same kind of pieces of processing repeatedly. In the conventional method, data is transmitted downstream after being processed by upstream child CPUs and hence does not reach a child CPU concerned unless the data is processed by the child CPUs upstream of it. Therefore, if the pieces of positioning processing 811*a*-813*a* performed by the child CPU 1 (hatched in FIG. 8(*a*)) are extremely long, the subsequent pieces of processing 821*a*-823*a* and 831*a*-833*a* (performed by the child CPUs 2 and 3) require long data reception standby times and hence the total processing speed is low.

In contrast, where the defect detection process is executed by the system configuration according to the embodiment shown in FIG. 5(*a*), as shown in FIG. 8(*b*), pieces of positional deviation detection and positioning processing (step 303) can be performed by two child CPUs as one group of pieces of processing 811*b*, 812*b*, 821*b*, and 822*b* and feature quantity calculations (step 304), pieces of feature space formation processing (step 305), and pieces of defect candidate extraction processing (step 306) can be performed as another group of pieces of processing 831*b*-834*b* according to the processing times of the respective pieces of processing. The number of child CPUs in charge of each kind of processing can be changed freely so that the child CPUs 1-3 bear uniform computation loads. In this example, since the computation load of the hatched pieces of positioning processing 811*b*, 812*b*, 821*b*, and 822*b* is approximately two times that of the other pieces of processing, the pieces of positioning processing are performed by the two child CPUs 1 and 2. To avoid occurrence of standby times, this is done in such a manner that the images 61-64 which are input continuously are processed alternately by the child CPUs 1 and 2. Furthermore, the feature quantity calculations to the pieces of defect candidate extraction processing (pieces of processing 831*b*-834*b*) whose computation loads are light are processed by the single child CPU 3. In this manner, the process can be executed at a higher speed than in the case of FIG. 8(*a*) with the same number of CPUs as in the case of FIG. 8(*a*).

FIG. 8(*c*) shows another exemplary process. After defect candidates have been extracted as in the case of FIG. 8(*a*), which pieces of positional deviation detection and positioning processing can be performed as one group of pieces of processing 811*c*-814*c*, pieces of feature space information processing can be performed as other group of pieces of processing 821*c*-824*c* and pieces of defect candidate extraction processing can be performed as other group of pieces of processing 831*c*-834*c*, pieces of processing (indicated by horizontal stripes) of cutting out partial images around the defect candidates and corresponding partial images from the reference images are performed as other group of pieces of processing 841*c*-844*c*. Now assume that partial images are cut out of original images. Then, in the conventional system configurations of FIGS. 5(*b*) and 5(*c*), when defect candidates have been extracted and defect positions have been determined by the child CPUs 1-3, the child CPU 4 receives position coordinates of the defects, reads the original images held by the parent CPU, and cuts out images around the defect coordinates. In contrast, in the system configuration of FIG. 5(*a*) according to the embodiment, the child CPUs 1-3 operate with data transfer via the counterclockwise data communication bus 501 and, in parallel with this processing, the original images are transmitted to the child CPU 4 via the clockwise data communication bus 502. The child CPU 4 holds the received original images in a memory, cuts out partial images upon reception of defect coordinates, and sends out the cut-out partial images sequentially to the parent CPU via the clockwise data communication bus 502. This enables high-speed data exchange without causing standby times of a communication timing control. Having a dedicated memory, each CPU can hold original images in advance like the child CPU 4 does in the above example.

As described above, the defect detection process is executed by the configuration in which the parent CPU and the plural child CPUs are linked to each other via at least one pair of oppositely directed data communication buses and the CPUs can exchange data freely. A high-speed defect inspection can be realized in which the assignment of pieces of processing and the data flows can be changed flexibly and no inter-CPU communication control etc. are necessary.

Such a system may be implemented by CPUs of any kind. Providing plural systems (boards) having such a configuration enables inspection processing of an even higher speed which is enhanced in parallelism. FIGS. 19(*a*) and 19(*b*) show an example of such a system. FIG. 19(*a*) shows that the input image 61 of the inspection subject chip 23 shown in FIG. 6(*a*) is equally divided into eight images 61-1 to 61-8 in the direction parallel with the stage movement direction. The divisional images 61-1 to 61-8 are input to dedicated memories 18-2-1 to 18-2-8 shown in FIG. 19(*b*), and pieces of defect detection processing are performed in parallel by plural systems (boards) having the configuration of FIG. 5(a) (in this example, eight systems 18-3-1 to 18-3-8 which are the same in number as the divisional images). The sequentially input images 62-66 are processed in similar manners.

Embodiment 2 of the Invention for Solving the First Problems

Figure 9:
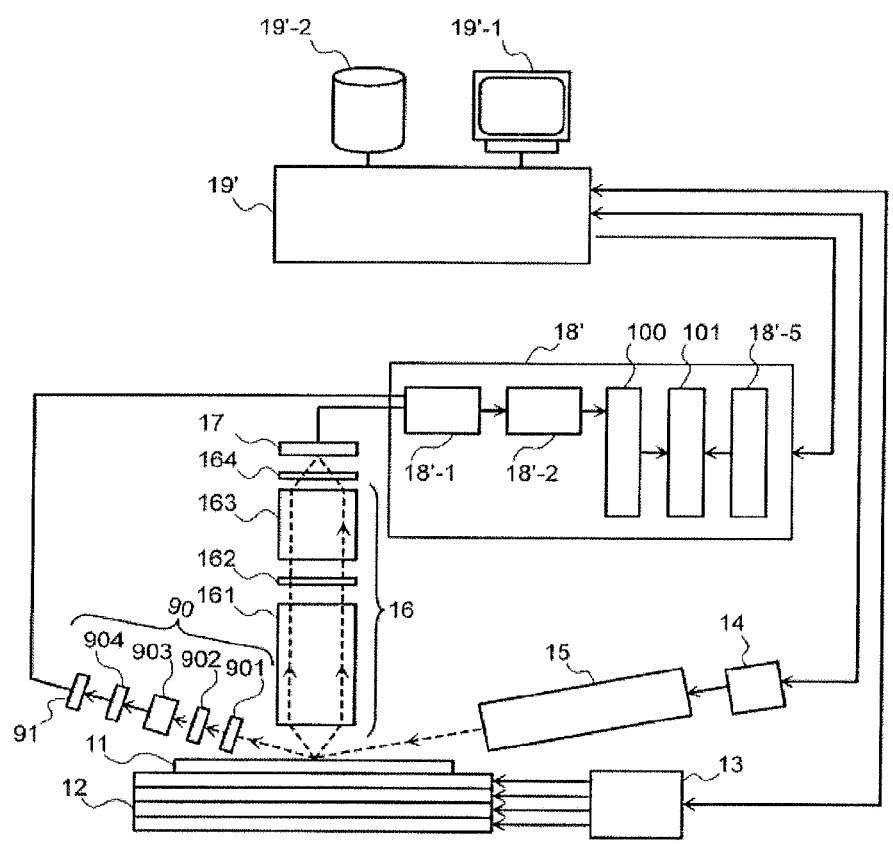
FIG. 9 shows the configuration of an inspection apparatus according to a second embodiment which is equipped with plural detection optical systems.

A second embodiment is directed to another defect inspection method in which the image processing system having the system configuration described in the first embodiment is employed and plural detection optical systems for detecting images are provided. The inspection apparatus of FIG. 9 is configured in such a manner that an oblique detection optical system 90 is added to the defect inspection apparatus of FIG. 1 which uses dark-field illumination (i.e., two detection optical systems are provided). Like the upper detection system 16, the oblique detection optical system 90 is composed of an objective lens 901, a spatial filter 902, an image-forming lens 903, and an optical filter 904. Scattered light coming from a sample 11 is image-formed via the objective lens 901, the spatial filter 902, the image-forming lens 903, and the optical filter 904, and a resulting optical image is detected by an image sensor 91 and thereby converted into an image signal. The thus-obtained image signal is input to an image comparison processing section 18' which is shared with the upper detection system 16, and processed there Images taken by the two different detection systems are naturally different in image quality, and different types of defects are detected by the two detection systems as well as common types. Therefore, a wider variety of defects can be detected by detecting defects by unifying pieces of information obtained by the two detection systems 16 and 90.

Similar to FIG. 1, symbol 19' denotes a total control section which incorporates a CPU for performing various controls. The total control section 19 is connected to a user interface section 19'-1 having a display means and an input means through which to receive, from a user, an instruction of alterations to inspection parameters (e.g., feature quantity types and threshold values which are used for extraction of excessively deviated values) and to display detected defect information and a storage device 19'-2 for storing feature quantities of detected defect candidates, images, etc. The total control section 19' also controls operation of the mechanical controller 13, the image comparison processing section 18, and the optical systems, etc.

Figure 10A:
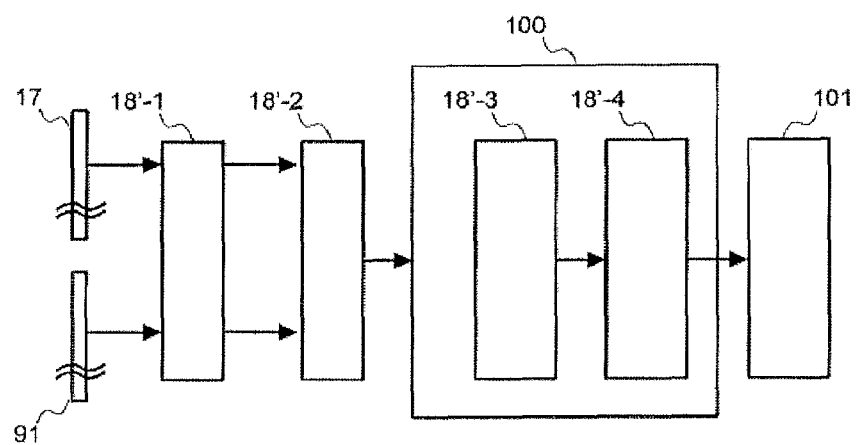
FIG. 10(a) is a block diagram showing the configuration of a defect detection system according to the second embodiment.

FIG. 10(a) shows an exemplary configuration for unifying pieces of information obtained by the plural detection systems. In this example, image signals of the respective detection systems that have been corrected by a pre-processing section 18'-1 and input to an image memory 18'-2 are processed sequentially by a defect detecting section 18'-3 and a defect classifying section 18'-4 of an image processing section 100. In a defect information unification processing section 101, sets of defects extracted via the detection systems are collated with each other on the basis of their coordinates on the semiconductor wafer and results are unified by taking the AND (defects that are extracted by all of the different detection systems) or OR (defects that are extracted by all or one of the different detection systems). Unified results are displayed on a user interface section 19'-1. Another procedure is possible in which processing results of the image processing section 100 are not unified by the defect information unification processing section 101 and sets of results corresponding to the respective detection systems are displayed individually on the user interface section 19'-1.

Figure 10B:
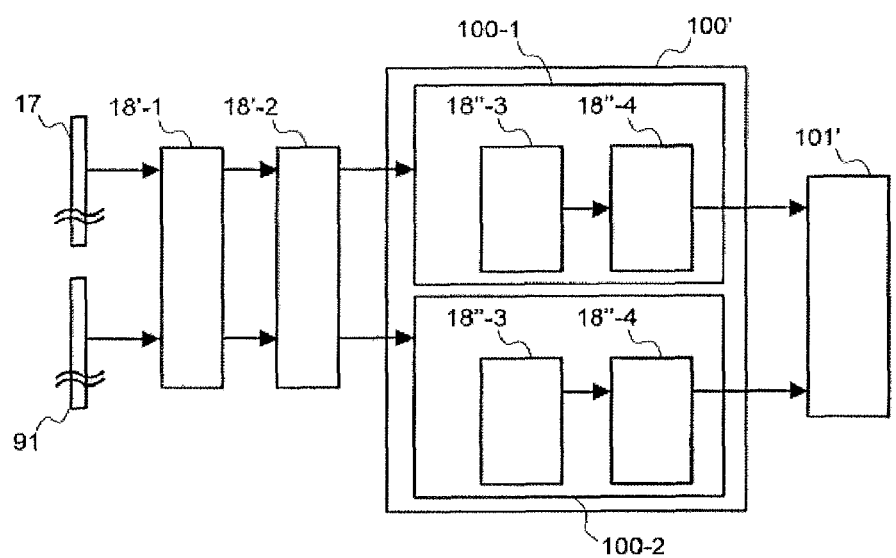
FIG. 10(b) is a block diagram showing the configuration of another defect detection system according to the second embodiment.

On the other hand, FIG. 10(b) shows a configuration in which an image processing section 100' is composed of a first image processing section 100-1 and a second image processing section 100-2. Image signals corresponding to the respective detection systems are processed in parallel by the first image processing section 100-1 and the second image processing section 100-2 each of which is equipped with a defect detecting section 18'''-3 and a defect classifying section 18'''-4, and final results are unified by a defect information unification processing section 101'. Unified results are displayed on the user interface section 19'-1.

Instead of merely unifying and displaying results extracted via the plural detection optical systems (in the configuration of FIG. 9, the two systems, that is, the upper detection system 16 and the oblique detection system 90), it is also possible to detect and display defects by unifying feature quantities of defect candidates obtained via the detection systems.

Figure 11:
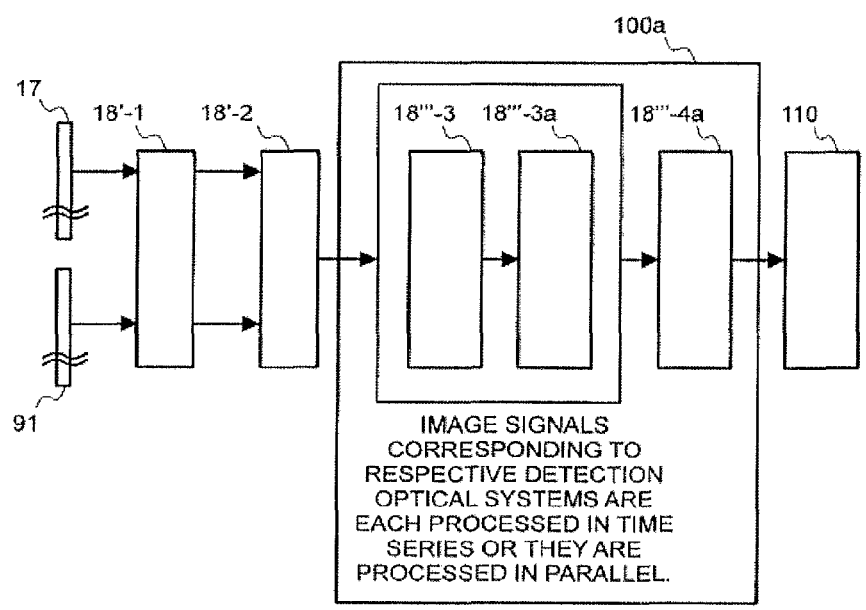
FIG. 11 is a block diagram showing the configuration of another defect detection system according to the second embodiment.

FIG. 11 shows such an example. First, image signals that have been detected by the image sensors 17 and 19, corrected by the pre-processing section 18'-1, and stored in the memory 18'-2 are called sequentially by an image processing section 100a. And the image signals corresponding to the respective detection optical systems are each processed in time-series or they are processed in parallel (section 18'''-3), whereby defect candidates are extracted. As described above with reference to FIG. 8(c), a defect image cutting section 18'''-3a cuts out, as partial images, images (hereinafter referred to as "defect images") of local regions including the defect candidates and corresponding reference images. When defect images corresponding to all the detection systems have been obtained, a defect classifying section 18'''-4a extracts feature quantities for classification from each of sets of defect images corresponding to the respective detection systems and having the same coordinates or from pixels, corresponding to each other, of sets of defect images corresponding to the respective detection systems, makes classification into false judgment points and defects and classification by defect types, and displays results on a section 110 (corresponds to the section 19'-1 shown in FIG. 9). Calculating feature quantities of defect portions from images acquired by the plural detection optical systems, unifying those, and makes classification in the above manner makes it possible to perform defect detection and classification with even higher accuracy. Performed on the basis of coordinate information on a wafer of detected defects, the above information unification can be realized even if images of the same region on the wafer are taken by the respective detection optical systems with different timings or at different magnifications.

Figure 12A:
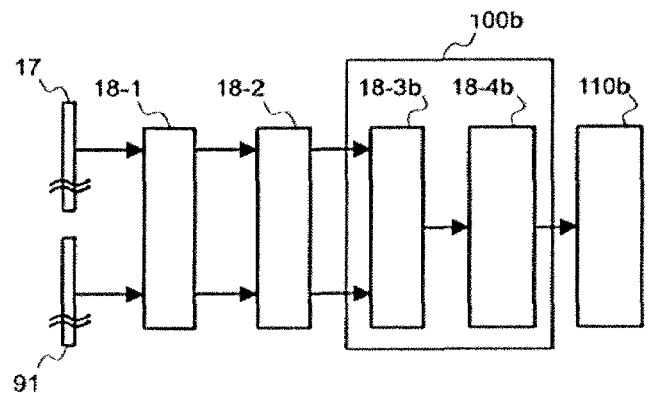
FIG. 12(a) is a block diagram showing the configuration of still another defect detection system according to the second embodiment.

Another form of inspection with information unification will be described below in which the imaging magnifications of respective detection optical systems are the same. FIG. 12(a) shows an example in which images are taken by two detection optical systems simultaneously at the same magnification. Images acquired by the two image sensors 17 and 91 with the same timing are corrected by a pre-processing section 18"-1 in the same manner as in the first embodiment (see FIG. 1), and corrected images are input to an image memory 18"-2. An image processing section 100b cells the image signals stored in the image memory 18"-2, and a section 18-3b extracts defect candidates using sets of an inspection subject image and a reference image taken by the two different detection systems. A section 18-4b makes classification and a section 110b (corresponds to the section 19'-1 shown in FIG. 9) displays results.

Figure 12B:
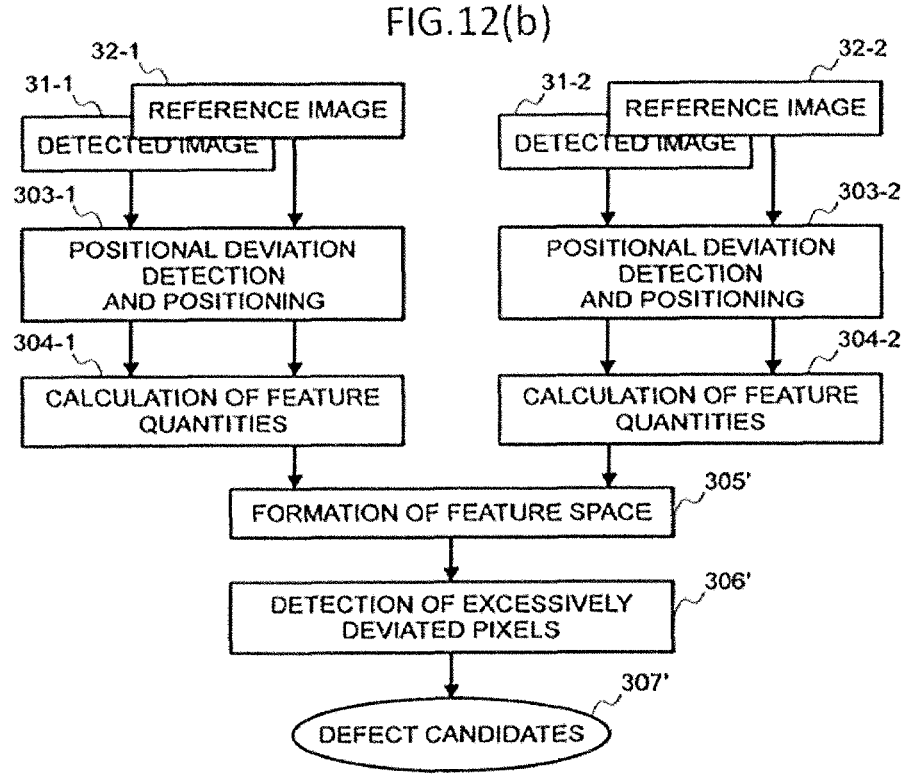
FIG. 12(b) is a flowchart of a defect detection process which is executed by the defect detection system of FIG. 12(a)

FIG. 12(b) shows an exemplary defect candidate extraction process which is executed by the section 18-3b. First, a detected image 31-1 obtained by one detection system (in this example, the upper detection system 16) and a corresponding reference image 32-1 are read from the image memory 18"-2 and positional deviations are detected and positioning is performed (step 303-1). Then, feature quantities are calculated from each pixel of the thus-positioned detected image 31-1 and a corresponding pixel of the reference image 32-1 (step 304-1). Likewise, a detected image 31-2 obtained by the other detection system (in this example, the oblique detection system 90) and a corresponding reference image 32-2 are read from the image memory 18"-2 and positioning (step 303-2) and feature quantity calculation (step 304-2) are performed. Then, all or some of pairs of feature quantities determined by the feature quantity calculation (steps 304-1 and 304-2) are selected and a feature space is formed (step 305'), whereby the pieces of information of the images obtained by the different detection systems are unified. Excessively deviated pixels are detected from the thus-formed feature space (step 306'), whereby defect candidates are extracted (step 307').

As described above, (1) brightness, (2) contrast, (3) density difference, (4) brightness variance of nearby pixels, (5) correlation coefficient, (6) brightness increase or decrease from nearby pixels, (7) second-order differential coefficient, etc. are calculated as feature quantities from each set of images. Brightness values themselves of the respective images 31-1, 32-1, 31-2, and 32-2 are also employed as feature quantities. Alternatively, feature quantities (1)-(7) may be calculated after unifying the images obtained by the respective detection systems, for example, from average values of the images 31-1, 32-1, 31-2, and 32-2.

To unify information on a feature space, it is necessary that correspondence between pattern positions of images obtained by the different detection systems be taken. Correspondence between pattern positions may be taken in advance by calibration or taken through calculation using obtained images. Although the process of FIG. 12(*b*) is such that positional deviation detection and positioning are performed on each set of images (steps 303-1 and 303-2), if the two detection systems acquire images with the same timing it is possible to detect positional deviations using either set of images and perform positioning on the other set of images using the thus-calculated positional deviations. This makes it possible to reduce the system scale and to increase the processing speed.

Figure 13:
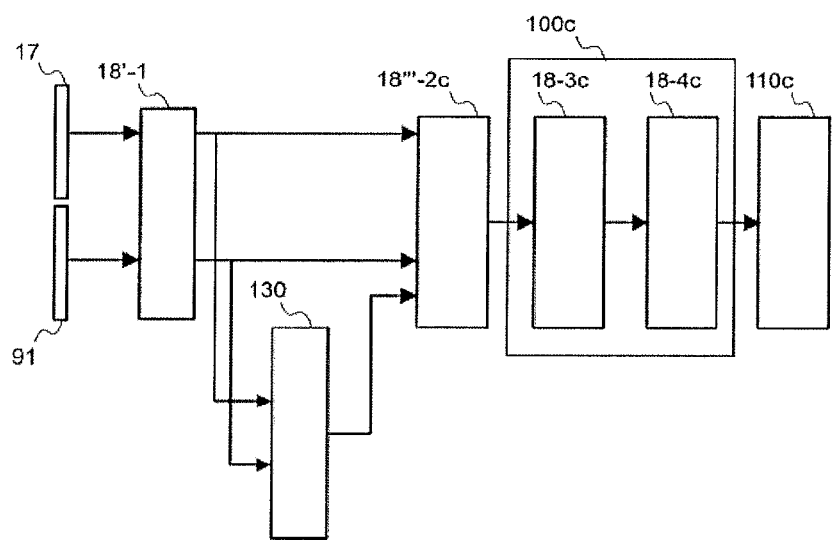
FIG. 13 is a block diagram showing the configuration of yet another defect detection system according to the second embodiment.

FIG. 13 shows another example in which images are taken by the two detection optical systems simultaneously at the same magnification. In this example, images are first combined with each other and then subjected to a defect detection process. A pre-processing section 18'-1 corrects images received from the respective image sensors, and writes corrected images to an image memory 18-2*c*. At the same time, an image combining section 130 combines the two corrected images (in this example, images corresponding to the upper detection system 16 and the oblique detection system 90), and inputs a composed image to the image memory 18-2*c*. In the image combining, various kinds of values such as average values, maximum values, and minimum values may be calculated. In an image processing section 100*c*, a section 18-3*c* extracts defect candidates using not only the images corresponding to the respective detection systems but also the composed image produced by the image combining section 130. A section 18-4*c* makes defect classification. In the defect candidate extraction processing of the section 18-3*c*, not only the detected images 31-1 and 31-2 but also the composed image is subjected to positional deviation detection and positioning and results are plotted in a feature space. The positional deviation detection and positioning on the detected images and the composed image to the plotting in the feature space are performed according to the same procedure as shown in FIG. 12(*b*). Alternatively, the defect candidate extraction processing to the classification processing may be performed on only the composed image.

As described above, in this embodiment, pieces of information obtained by the plural detection optical systems can be unified at each of the following various stages:

(1) Unification of defect detection results (2) Unification of feature quantities (pieces of defect information) of defect candidates (3) Unification of feature quantities of images (4) Unification of images Unification can be performed for two or more detection systems.

In this manner, it becomes possible to detect a variety of defects with high sensitivity.

Figure 14:
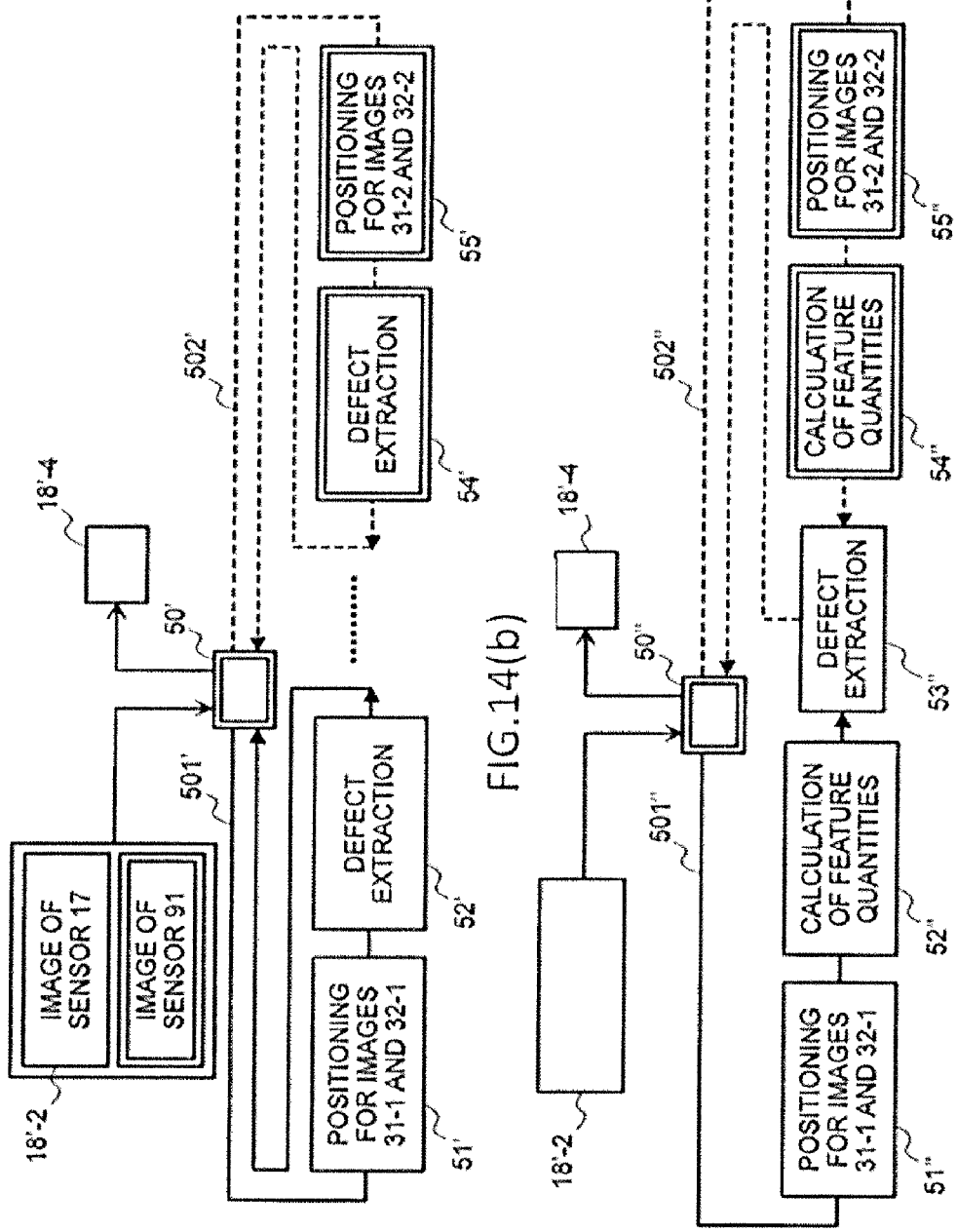
FIG. 14(a) is a block diagram showing a CPU arrangement for a defect detection process according to the second embodiment.
FIG. 14(b) is a block diagram showing a CPU arrangement for unification of image feature quantities in a defect detection process according to the second embodiment.

FIGS. 14(*a*) and 14(*b*) show other implementation forms of systems which unify pieces of information obtained by plural detection systems and which employs the inspection system of FIG. 9 and the configuration of FIG. 5(*a*). In these examples, there are two detection systems and two sets of images are input from the sensors 17 and 91 to the image memory. In the example of FIG. 14(*a*), a parent CPU 50' reads two sets of images and transmits a detection image 31-1 and a reference image 32-1 acquired from the sensor 17 via a counterclockwise data communication bus 501'. Positioning is performed by a child CPU 51' and defect extraction is performed by a child CPU 52'. Results are returned to the parent CPU 50' via a clockwise data communication bus 502'. On the other hand, the parent CPU 50' transmits a detection image 31-2 and a reference image 32-2 acquired from the sensor 91 via the clockwise data communication bus 502'. Positioning is performed by a child CPU 55' and defect extraction is performed by a child CPU 54'. Results are returned to the parent CPU 50' via the counterclockwise data communication bus 501'. The parent CPU 50' unifies the pieces of information returned from the two sets of child CPUs, and a section 18'-4 makes defect classification on the basis of unification results. In this manner, a high-speed, parallel comparison processing with almost no communication standby times of image transfer can be realized in the form of a single image processing system. FIG. 14(*b*) shows another implementation form of a process for unifying feature quantities of images. As in the case of FIG. 14(*a*), respective sets of images are transmitted via oppositely directed data communication buses 501" and 502" and subjected to positioning by a child CPU 51" and a child CPU 55" and feature quantity calculation by a child CPU 52" and a child CPU 54". Data are transmitted to a child CPU 53" from both sides, and the child CPU 53" forms a feature space and extracts defect candidates. Results are transmitted to a parent CPU 50" via a bus that makes the child CPU 53" closer to the parent CPU 50". The combination of the process flow, the data communication direction, the manner of assignment of individual computations to CPUs, etc. is not limited to the ones of the examples of FIGS. 14(*a*) and 14(*b*) and may be in other forms.

As described above, a detect detection process implemented by a system configuration which is composed of plural computation CPUs and a parent CPU organizing them and in which each CPU is connected to one or more sets of oppositely directed data communication buses can be executed at high speed in any of various forms such as a parallel process and a pipeline process. Furthermore, the configuration can be changed flexibly according to the load. The typical number of child CPUs for one parent CPU is eight, and plural computation systems each having this configuration may be combined so as to operate in parallel depending on the scale of images to be handled and the computation load.

Figure 15:
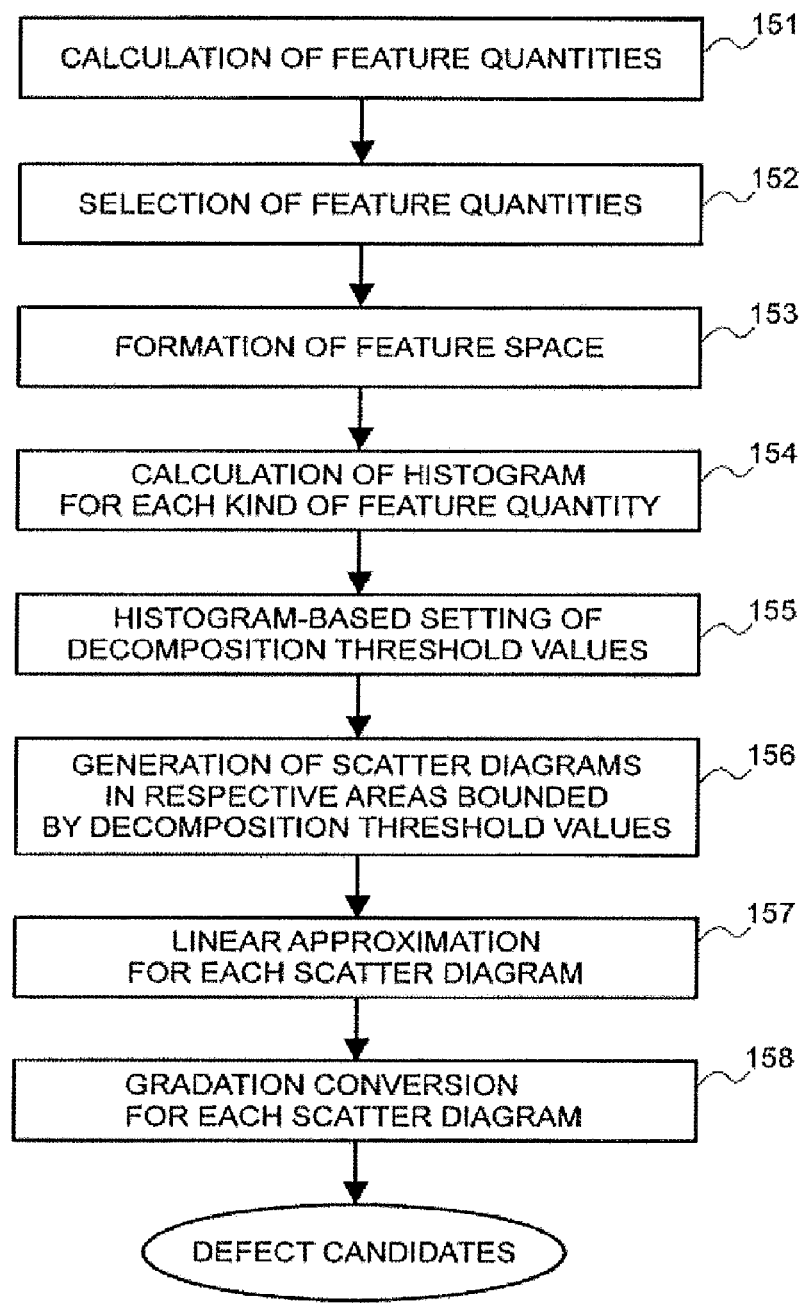
FIG. 15 is a flowchart showing the procedure of a process for detecting excessively deviated values using feature quantities.

Next, a detailed version of the defect candidate extraction process of FIG. 3 in which excessively deviated values are detected in a feature space will be described with reference to FIG. 15. A semiconductor wafer as an inspection subject bears multilayer films, and the degree of brightness variation (i.e., noise intensity) between a detected image and a reference image due to interference between thin films, pattern edge roughness, etc. depends on the layer. Therefore, if defect detection is performed with the same sensitivity over the entire area of the inspection subject, it is necessarily performed with low sensitivity which is suitable for areas with high noise, resulting in missing of defects. In view of this, in this embodiment, defects are detected in such a manner that an image is decomposed into several categories on the basis of feature quantities of individual pixels and processing is performed on a category-by-category basis. An example of the category-by-category process is such that a brightness variation (e.g., variance) of pixels belonging to a certain category is calculated and the sensitivity is set automatically according to the variation (e.g., variance) which is considered a noise level. This is equivalent, in effect, to a procedure that an image is divided into areas (layers) with high noise and areas (layers) with low noise and defects are detected with low sensitivity in the high-noise areas and with high sensitivity in the low-noise areas. This is a concept which is called sorting in statistics. First, at step 151, feature quantities are calculated for each pair of corresponding pixels of a detected image and a reference image. As described above, there are various kinds of feature quantities. At step 152, plural feature quantities that are most suitable for image classification by the pattern or the noise level are selected from those various kinds of feature quantities. Feature quantities may be selected according to a user's experiences, selected manually while typical values of an area or pattern to be separated are checked, or selected by checking the degree of separation while selecting feature quantities in a narrow region on a trial basis. Another procedure is possible that a user points out an area or pattern to be separated and feature quantities are selected automatically so that its degree of separation from the other areas becomes highest.

Figure 16A:
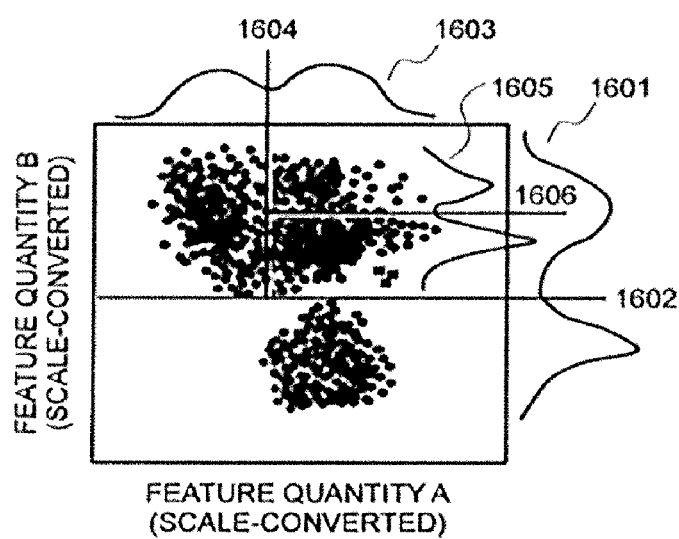
FIG. 16(a) is a graph obtained by plotting pixels of an image in a two-dimensional feature space.

Exemplary methods for evaluating the degree of separation are a method of selecting feature quantities so that the variance becomes small in each area to be separated and the inter-area variances become large and a method based on a discrimination analysis. In measuring the degree of separation, the conversion of the feature quantity axes and their scale conversion are performed so that the degree of separation becomes higher. At step 153, a feature space is formed by plotting pixels in a feature space having one or more selected feature quantities as axes. At step 154, a histogram is calculated for each kind of feature quantity on the feature space. At step 155, threshold values for area division are calculated on a histogram basis. FIGS. 16(a)-16(e) show a histogram-based area dividing method. FIG. 16(a) shows an example in which pixels of an image are plotted in a feature space defined by two selected feature quantities A and B. First, a histogram is generated for each of the selected feature quantities A and B. A histogram having clearest peaks and valleys is chosen from the histograms for the respective feature quantities, and a most valley-like portion in the thus-chosen histogram is made a first threshold value. Peak-likelihood and valley-likelihood are calculated by differentiating a histogram.

In FIG. 16(a), a histogram 1601 corresponding to the feature quantity B is chosen and a threshold value 1602 is set. Then, the feature space is divided at the thus-set threshold value 1602. Then, histograms are formed for the respective feature quantities in each divisional (partial) feature space. A histogram having clearest peaks and valleys is chosen, and a most valley-like portion in the thus-chosen histogram is made the next threshold value. In FIG. 16(a), a threshold value 1604 is set from a histogram 1603. This operation is repeated until each histogram does not have a valley. Whether or not a histogram has a valley is determined by setting a judgment threshold value for differential coefficients. In FIG. 16(a), this operation is finished when a threshold value 1606 is set from a histogram 1605. In this manner, the feature space is divided while threshold values are calculated, and defects are detected in each divisional (partial) feature space by using the pixels contained therein. An example in which defects are detected on the basis of a scatter diagram will be described below. First, a scatter diagram is formed for each divisional (partial) feature space by using pixels contained therein (step 156 in FIG. 15). Each scatter diagram is such that pixels are plotted in a two-dimensional space that is defined by the brightness of the pixel of the inspection subject image (horizontal axis) and the brightness of the corresponding pixel of the reference image (vertical axis). FIG. 16(b) is a scatter diagram formed from the entire inspection image. FIG. 16(c) is a scatter diagram formed from the pixels contained in the upper-half divisional area obtained by the threshold value 1602 that is set first in the feature space of FIG. 16(a), and FIG. 16(d) is a scatter diagram formed from the pixels contained in the lower-half divisional area. In FIG. 16(e), data of pixel sets contained in the respective areas formed by dividing the area corresponding to FIG. 16(c) at the threshold values 1604 and 1606 are enclosed by ellipses. In this manner, the scatter diagram of FIG. 16(b) is decomposed by forming scatter diagrams for respective divisional (partial) feature spaces. This means dividing the subject image according to the feature quantities. If feature quantities are selected so as to reflect noise intensity, high-noise regions and low-noise regions can be separated from each other. As a result, in low-noise regions, influence of high-noise regions can be eliminated. Then, at step 157, a slope (gain) and a Y-intercept (offset) are calculated by performing straight-line approximation on the data of each decomposition scatter diagram. At step 158, a gradation conversion is performed on the pixels contained in each area by using "gain" and "offset" according to the following equation:

$$f'(x, y) = \text{gain} \cdot f(f, y) + \text{offset}$$

where $f(x, y)$ is the brightness of the detected image before the gradation conversion and $f'(x, y)$ is the brightness after the gradation conversion. The gradation conversion is nothing other than adjusting the brightness of each pixel of the detected image to that of the reference image. Defect candidates are extracted by comparing differences between the detected image and the reference image after the gradation conversion and a threshold value that is set by a user.

Figure 17A:
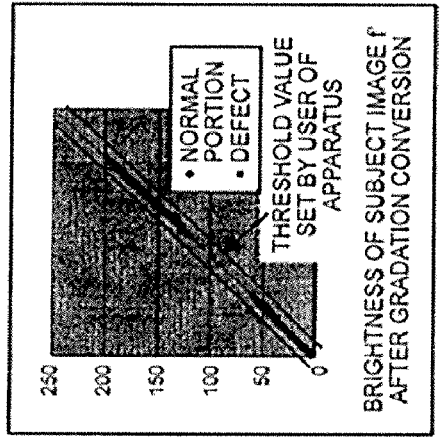
FIG. 17(a) is a hierarchy diagram showing how a feature space is decomposed on a histogram basis.

In this exemplary method, as shown in FIG. 17(a), the feature space is decomposed on a histogram basis (in this example, into areas A-D) and gradation conversion coefficients "gain" and "offset" are obtained as output values by straight-line approximation in each area. Variations, variances, or the like of groups of data belonging to the respective areas are also output as feature quantities, which serve as evaluation values indicating whether the decomposition has been made successfully. When histograms are no longer divided or the variations are smaller than a predetermined threshold value, the decomposition is finished. The variation may be evaluated by using the variance of a scatter diagram or on the basis of the magnitude of a slope that is obtained by sampling two proper data. The number of data (frequency) in each divisional area can also be used.

Figure 17B:
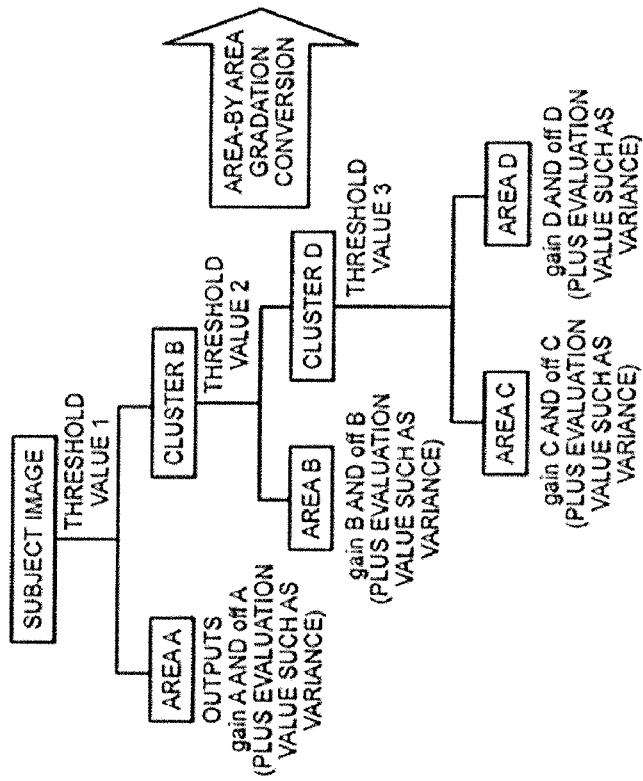
FIG. 17(b) is a scatter diagram of the entire subject image which is obtained after the brightness of each pixel is adjusted by using gradation conversion coefficients calculated for each area.

FIG. 17(b) is a scatter diagram of the entire subject image which is obtained after the brightness of each pixel is adjusted by using gradation conversion coefficients calculated for each area. FIG. 17(b) shows that the data distributions are made slim and hence a smaller threshold value can be set. Since as described above gradation conversion is performed for each area, a user of the apparatus need not make complicated sensitivity setting and excessively deviated values in each divisional area can easily be detected as defects by using a single sensitivity parameter. Naturally, sensitivity setting can be made for each divisional area instead of performing gradation conversion. In this case, a user may adjust the sensitivity manually for each area or sensitivity may be calculated according to a variance which is an evaluation value for each area shown in FIG. 17(a). For example, if the variance $\sigma$ is large, it is judged that the brightness has a large variation (i.e., the area has high noise) and the threshold value TH is set large. If the variance $\sigma$ is small, it is judged that the area has low noise and the threshold value TH is set small. The threshold value TH may be calculated in the following manner according to the variance $\sigma$:

$$TH = K\sigma$$

where K is the parameter which is set by a user.

The method for dividing an image is not limited to the feature-quantity-histogram-based method, and other methods can be used in which a threshold value is determined taking post-decomposition variations into consideration by using a linear regression tree or a determination tree. That is, it is possible to divide a histogram so that variances become smaller than a certain value. Instead of decomposing a feature space, segmentation may be performed directly from spatial information of an image itself. Defects are detected on a segment-by-segment basis.

As described above, in the inspection apparatus according to each embodiment of the invention, the system configuration of the image processing section includes the parent CPU, the plural child CPU, and the oppositely directed data transfer buses. This makes it possible to provide a high-speed defect detection method and apparatus in which pieces of processing can be assigned to CPUs freely. Detecting excessively deviated values in a feature space makes it possible to detect defects buried in noise with high sensitivity merely by simple parameter setting Furthermore, since pieces of information of images detected by the plural detection optical systems are unified and then subjected to defect detection processing, a variety of defects can be detected with high sensitivity.

In the above examples, a comparative inspection is performed by using an image of an adjacent chip (the region 22 shown in FIG. 2(a)) as a reference image. However, this aspect of the invention encompasses a method in which one reference image is generated from average values or the like of plural chips (the regions 21, 22, 24, and 25 shown in FIG. 2(a)) and a method in which one-to-one comparison is performed for plural regions (e.g., combinations of the regions 23 and 21, regions 23 and 22, . . . , 23 and 25) and defects are detected by processing all comparison results statistically.

The above embodiments are directed to the comparative processing on chips. However, the invention encompasses cell comparison which is performed on each memory mat portion in the case where memory mat portions and a peripheral circuit portion exist in mixed form in an inspection subject chip as shown in FIG. 2(b).

The invention enables detection of defects of 20 to 90 nm in size even if subtle differences exist in film thickness between patterns after execution of a planarization process such as CMP or large differences exist in brightness between chips for comparison due to shortening of the wavelength of illumination light.

Furthermore, the invention enables detection of defects of 20 to 90 nm in size even if local brightness differences occur due to a variation of an in-film refractive index distribution in inspection of a low-k film as exemplified by inorganic insulating films such as an $SiO_2$ film, an SiOF film, a BSG film, an SiOB film, and a porous silia film and organic insulating films such as a methyl-group-containing $SiO_2$ film, an MSQ film, a polyimide film, a parylene film, a Teflon (registered trademark) film, and an amorphous carbon film.

Figure 18:
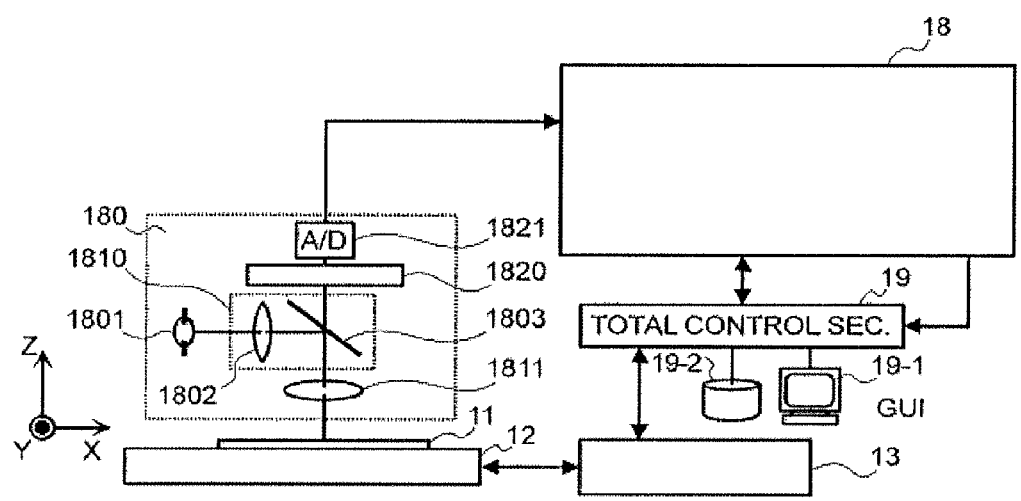
FIG. 18 is a front view of a bright-field inspection apparatus which is an application example of the first embodiment.
Figure 19A:
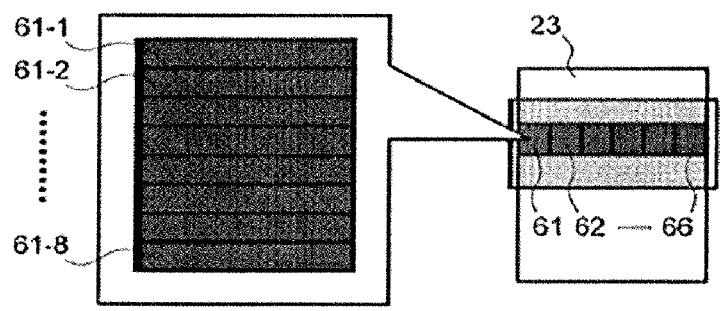
FIG. 19(a) is an enlarged plan view of a chip on a semiconductor wafer.
Figure 19B:
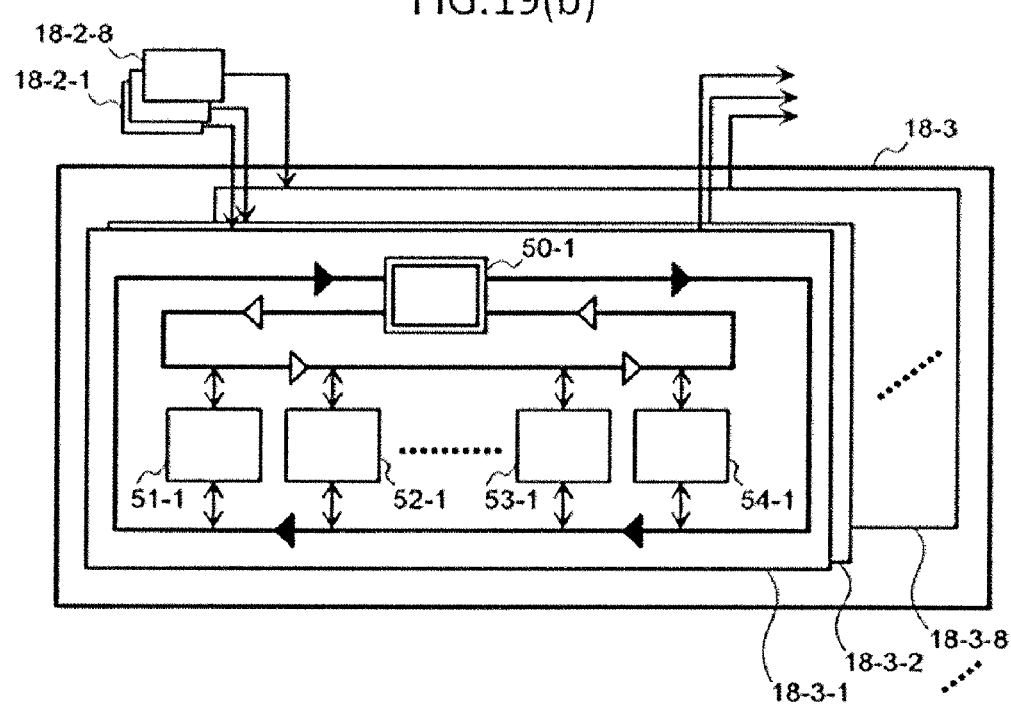
FIG. 19(b) is a block diagram of a CPU arrangement for a defect detection process in which the parallelism is enhanced further.

Each of the embodiments of the invention for solving the first problems has been described above by using, as an example, a comparative inspection image in a dark-field inspection apparatus for semiconductor wafers. However, the invention can also be applied to a comparative inspection image in an electron beam pattern inspection as well as a pattern inspection apparatus with bright-field illumination. FIG. 18 shows the configuration of an exemplary defect inspection apparatus with bright-field illumination. Symbol 180 denotes a detecting section, which is composed of a light source 1801 for illuminating a sample 11, an illumination optical system 1810 having a lens system 1802 for gathering light emitted from the light source 1801 and a beam splitter 1803 for converting the optical path, an objective lens 1811 for illuminating the sample 11 with the illumination light gathered by the illumination optical system 1810 and for forming an optical image of reflection light from the sample 11, an image sensor 1820 for detecting the optical image and converting it into an image signal according to its brightness, and an AD conversion section 1821 for converting the input signal from the image sensor 1820 into a digital signal.

The inspection subject is not limited to a semiconductor wafer and may be a TFT substrate, a photomask, a printed circuit board, or the like as long as it is subjected to defect detection by image comparison.

As described above, the invention makes it possible to detect defects with high sensitivity from noise by automatically selecting, from plural feature quantities, in an interactive and statistical manner, feature quantities that are most suitable for detection of defects buried in noise.

Furthermore, since an inspection subject image is divided into areas according to feature quantities and sensitivity is set automatically for each divisional area, a high-sensitivity inspection is enabled merely by simple parameter setting.

Still further, since pieces of information obtained by plural optical systems can be unified at a desired process stage, it becomes possible to detect a variety of defects with high sensitivity. In addition, such a high-sensitivity inspection can be performed at high speed.

Next, a third embodiment of the invention for solving the second problems will be described with reference to FIG. 20, FIG. 21(a), FIG. 21(b), FIG. 21(c), FIG. 21(d), FIG. 22(a), FIG. 22(b), FIG. 23(a), FIG. 23(b), FIG. 24(a), FIG. 24(b), FIG. 25(a), FIG. 25(b), FIG. 26(a), FIG. 26(a-1), FIG. 26(a-2), FIG. 26(a-3), FIG. 26(b), FIG. 26(c), FIG. 27(a), FIG.

27(b), FIG. 27(c), FIG. 27(d), FIG. 28(a), FIG. 28(b), and FIG. 28(c) by using, as an example, a defect inspection of a semiconductor wafer.

Embodiment 3 of the Invention for Solving the Second Problems

Figure 20:
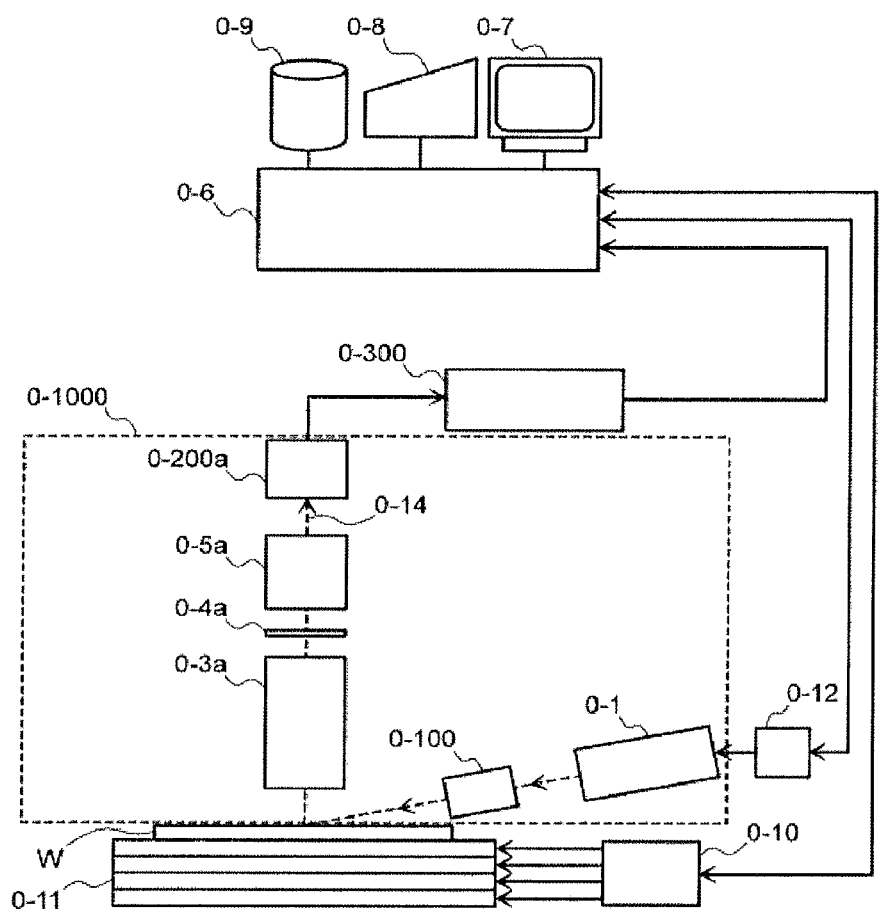
FIG. 20 shows a general configuration of a defect inspection apparatus according to a third embodiment of the invention for solving the second problems.

FIG. 20 shows the configuration of a defect inspection apparatus according to the third embodiment. This defect inspection apparatus is composed of a light source 0-1, an illumination optical system 0-100, an inspection subject substrate W, an objective lens 0-3a, a spatial filter 0-4a, an image-forming lens 0-5a, a polarization detecting section 0-200a, a signal processing section 0-300, a total control section 0-6, a display section 0-7, a computing section 0-8, a storage section 0-9, an X-Y-Z-θ stage driver 0-10, an X-Y-Z-θ stage 0-11, and a light source driver 0-12. The light source 0-1, the illumination optical system 0-100, the objective lens 0-3a, the spatial filter 0-4a, the image-forming lens 0-5a, and the polarization detecting section 0-200a constitute an optical system 0-1000.

The operation will be outlined below. Light emitted from the light source 0-1 is applied to the inspection subject substrate W via the illumination optical system 0-100. Reflection-scattered light from the inspection subject substrate W is gathered by the objective lens 0-3a, passes along a detection system optical path 0-14 after passing through the spatial filter 0-4a and the image-forming lens 0-5a, and is converted into an electrical signal by the polarization detecting section 0-200a. The signal processing section 0-300 makes a judgment on defects on the inspection subject substrate W. Judgment results are stored in the storage section 0-9 and displayed on the display section 0-7 by the total control section 0-6.

The spatial filter 0-4a is disposed at an exit pupil position of the objective lens 0-3a or its conjugate position, and serves to interrupt diffraction light pattern that are generated when fine-pitch repetitive patterns formed on the inspection subject substrate W. For example, the spatial filter 0-4a is provided with plural straight light shield patterns having variable pitches as disclosed in JP-A-2000-105203.

To illuminate the inspection subject substrate W with high illuminance, it is appropriate that the light source 0-1 be a laser light source. To increase the scattering efficiency of minute defects, the use of a short-wavelength light source such as a deep ultraviolet (DUV) laser, a vacuum ultraviolet laser, a YAG laser (third or fourth harmonic), a mercury lamp, or a xenon lamp is suitable. To attain the above purpose while reducing the costs of the components of the optical system and the maintenance cost, the use of a visible-wavelength light source such as a YAG laser (second harmonic), a halogen lamp, a mercury lamp, or a xenon lamp is suitable. To generate illumination light having a particular polarization state with high efficiency, the user of a laser light source capable of providing a high degree of polarization is suitable.

Figure 21A:
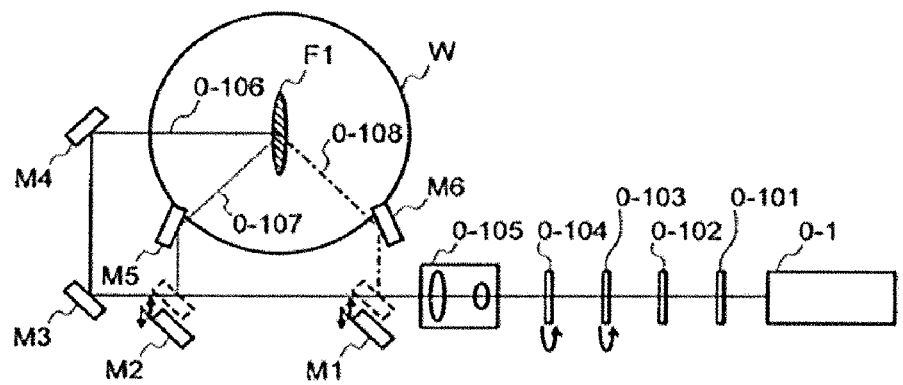
FIG. 21(a)-21(d) show a general configuration of an illumination optical system according to the third embodiment.

FIG. 21(a) shows the configuration of the illumination optical system 0-100. Illumination light emitted from the light source 0-1 is controlled in intensity by an attenuator 0-101. A polarizing plate 0-102, which is provided when necessary, converts the illumination light which originates from the light source 0-1 into linearly polarized light. Phase shifters 0-103 and 0-104 set the polarization state of the illumination light arbitrarily. Each of the phase shifters 0-103 and 0-104 is a λ/2 plate or a λ/4 plate which can be rotated about the optical axis or a phase shifter capable of controlling a phase shift. After passing through the phase shifters 0-103 and 0-104, the illumination light is increased in beam diameter by a beam expander 0-105. The illumination light whose beam diameter has been increased by the beam expander 0-105 is guided onto the inspection subject substrate W by mirrors M1-M9 and cylindrical lenses 0-109, 0-110, and 0-111. In FIG. 21(a), the cylindrical lens 0-109 and the mirror M7 are omitted because they are located at the same position as the mirror M4 in FIG. 21(a). The cylindrical lenses 0-110 and 0-111 and the mirrors M8 and M9 are also omitted in FIG. 21(a) because the relationship between the mirror M5, the cylindrical lens 0-110, and the mirror M8 and the relationship between the mirror M6, the cylindrical lens 0-111, and the mirror M9 are the same as the relationship between the mirror M4, the cylindrical lens 0-109, and the mirror M7.

Figure 21B:
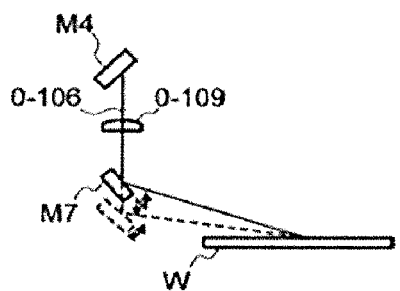
Figure 21C:
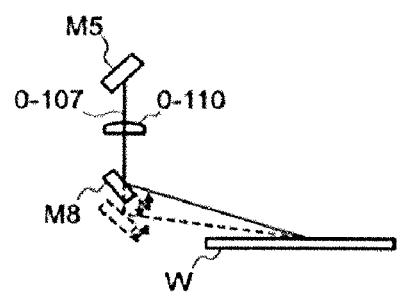
Figure 21D:
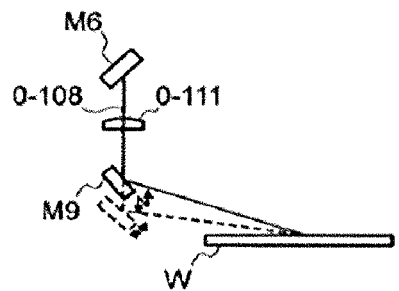
Figure 24A:
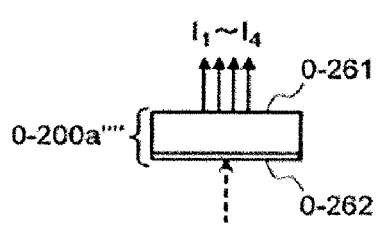
FIGS. 24(a) and 24(b) show a general configuration of a polarization detecting section using a polarizing optical element array according to the third embodiment.
Figure 24B:
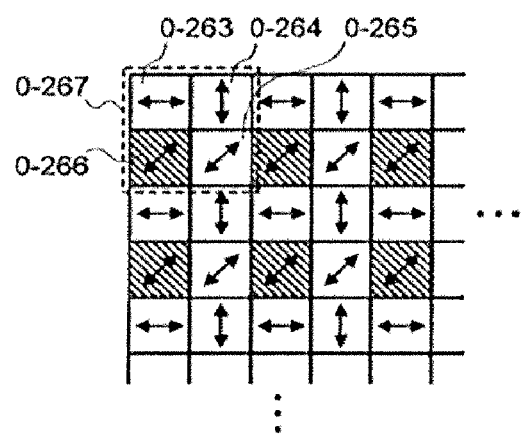

A case that an optical path 0-106 is taken will be described below. The mirrors M1 and M2 are retreated from the optical path, whereby the illumination light is reflected by the mirrors M3 and M4 and takes the optical path 0-106. FIG. 21(b) is a side view showing the structure from the mirror M4 to the inspection subject substrate W. The illumination light is focused by the cylindrical lens 0-109 so as to form an image in an elliptical or line-shaped region F1 on the inspection subject substrate W. The angle formed by the optical path and the surface of the inspection subject substrate W (i.e., the incident angle (elevation) of the illumination light to the inspection subject substrate W) can be changed by moving and rotating the mirror M7 in the directions indicated by arrows.

Likewise, as for the optical path 0-107, the mirror M8 and the cylindrical lens 0-110 are disposed between the mirror M5 and the inspection subject substrate W. As for the optical path 0-108, the mirror M9 and the cylindrical lens 0-111 are disposed between the mirror M6 and the inspection subject substrate W. Each of the cylindrical lenses 0-110 and 0-111 is inclined and rotated about the optical axis so that the illumination light that has passed through the cylindrical lens 0-110 or 0-111 forms, on the inspection subject substrate W, an image in a region whose center and the longitudinal direction coincide with those of the region F1 corresponding to the cylindrical lens 0-109. With the above configuration, the same region on the inspection subject substrate W can be illuminated selectively with illumination light that comes from one of the plural directions and has one of plural elevations. Furthermore, if the mirror M1 and/or the mirror M2 is a half mirror, the region F1 on the inspection subject substrate W can be illuminated simultaneously at plural elevations from plural directions.

The number of kinds of detectable defects and the inspection S/N ratio can be increased by providing a means for varying an optical condition of illumination light at high speed in the optical path of the illumination optical system 0-100, varying the optical condition of illumination light in a shorter time than a storage time of a photodetector of the polarization detecting section 0-200a (described later), and causing the photodetector to store signals obtained under varied illumination conditions. Examples of the means for varying an optical condition of illumination light at high speed are a means for scanning positions in a light beam at a pupil (disclosed in JP-A-2000-193443) and a means for rotating a diffusion plate (disclosed in JP-A-2003-177102).

The objective lens 0-3a and the image-forming lens 0-5a form an enlarged image of the illumination region F1 on the surface of the inspection subject substrate W. Diffraction light from periodic patterns formed on the inspection subject substrate W is gathered at the position that is conjugate with the pupil position of the objective lens 0-3a. Therefore, images of the periodic patterns can be eliminated by interrupting this diffraction light by the spatial filter 0-4a.

The polarization detecting section 0-200a will be described below with reference to FIGS. 22(a) and 22(b) to FIGS. 24(a) and 24(b).

FIG. 22(a) shows the configuration of a polarization detecting section 0-200a' which detects two different polarization components and which is an implementation example of the polarization detecting section 0-200a by use of the amplitude division method. The polarization detecting section 0-200a' is composed of a non-polarizing beam splitter (half mirror) 201, polarization selecting means 0-210 and 0-211 each of which is a polarizing plate or a combination of phase plates and can adjust the polarization state of light passing through it, and photodetectors 0-220 and 0-221. Each of the photodetectors 0-220 and 0-221 is disposed so as to detect an enlarged image of a portion of the surface of the inspection subject substrate W which is formed by the objective lens 0-3a and the image-forming lens 0-5a. Image surface conjugate positions, with the surface of the inspection subject substrate W, of the objective lens 0-3a and the image-forming lens 0-5a are indicated by chain lines as image surfaces 0-230 (the front surfaces of the photodetectors 0-220 and 0-221). Area sensors, linear sensors, or TDI (time delay integration) sensors are used as the photodetectors 0-220 and 0-221, whereby images corresponding to the respective polarization components are obtained.

Scattered light beams corresponding to illumination light beams produced under plural optical conditions can be detected together through integration by using time-integration-type (CCD or CMOS) photodetectors as area sensors, linear sensors, or TDI sensors and changing the optical condition at high speed in the illumination optical system 0-100 in a shorter time than the integration time of the photodetectors 0-220 and 0-221.

High-sensitivity detection can be attained by employing photomultiplier tubes as the photodetectors 0-220 and 0-221.

The following description will be directed to a case that the photodetector 0-220 detects a linearly polarized component whose polarization is parallel with major wiring patterns on the inspection subject substrate W and the photodetector 0-221 detects a linearly polarized component whose polarization is perpendicular to those.

Of light components that have passed through the non-polarizing beam splitter 0-201, a light component that has passed through the polarization selecting means 0-210 which is a polarizing plate that transmits a linearly polarized component whose polarization is parallel with the major wiring patterns on the inspection subject substrate W is detected by the photodetector 0-220. On the other hand, a light component that has passed through the polarization selecting means 0-211 which is a polarizing plate that transmits a linearly polarized component whose polarization is perpendicular to the major wiring patterns on the inspection subject substrate W is detected by the photodetector 0-221.

Another configuration which realizes the equivalent function is as follows. A polarizing beam splitter which transmits a linearly polarized component whose polarization is parallel with the major wiring patterns on the inspection subject substrate W is disposed in place of the non-polarizing beam splitter 0-201, and a polarizing plate which transmits a linearly polarized component whose polarization is perpendicular to the major wiring patterns on the inspection subject substrate W is disposed as the polarization selecting means 0-211. The former configuration has a merit that the polarization directions of polarized light beams to be detected can be changed merely by changing the polarization selecting means 0-210 and 0-211. The latter configuration has merits that it is not necessary to consider a polarizing characteristic remaining in the non-polarizing beam splitter 0-201 and that a more accurate polarization measurement can be performed than in the former configuration. Detecting linearly polarized components having orthogonal linear polarization directions in the above-described manner makes it possible to calculate, through computations on obtained measurement values, polarization-related physical quantities such as total intensity of light which is independent of the polarization components, the degree of linear polarization in the direction parallel with the major wiring patterns on the inspection subject substrate W, and a longer-axis azimuth angle of (elliptically) polarized light.

FIG. 22(b) shows the configuration of a polarization detecting section 0-200a' which detects four different polarization components and which is another implementation example of the polarization detecting section 0-200a by use of the amplitude division method. The polarization detecting section 0-200a' is composed of non-polarizing beam splitters 0-202 to 0-204, polarization selecting means 0-212 to 0-215, and photodetectors 0-222 to 0-225. Light shining on the polarization detecting section 0-200a' along the detection system optical path 0-14 is split by the non-polarizing beam splitters 0-202 to 0-204, and resulting light beams enter the different photodetectors 0-222 to 0-225. The polarization selecting means 0-212 to 0-215, each of which is a polarizing plate or a combination of phase plates, are set so as to be able to independently adjust the polarization states of light beams passing through them.

Each of the photodetectors 0-222 to 0-225 is disposed so as to detect an enlarged image of a portion of the surface of the inspection subject substrate W which is formed by the objective lens 0-3a and the image-forming lens 0-5a. As in the case of FIG. 22(a), the chain line on the front surface of each of the photodetectors 0-222 to 0-225 indicates an image surface conjugate position, with the surface of the inspection subject substrate W, of the objective lens 0-3a and the image-forming lens 0-5a. Area sensors, linear sensors, or TDI (time delay integration) sensors are used as the photodetectors 0-222 and 0-225, whereby images corresponding to the respective polarization components are obtained.

Scattered light beams corresponding to illumination light beams produced under plural optical conditions can be detected together through integration by using time-integration-type (CCD or CMOS) photodetectors as area sensors, linear sensors, or TDI sensors and changing the optical condition at high speed in the illumination optical system 0-100 in a shorter time than the integration time of the photodetectors 0-222 to 0-225.

High-sensitivity detection can be attained by employing photomultiplier tubes as the photodetectors 0-222 to 0-225.

A description will be made of a case that the photodetector 0-222 detects a linearly polarized component whose polarization has a prescribed azimuth angle (represented by $\alpha$) around the detection system optical path 0-14, the photodetector 0-223 detects a linearly polarized component whose polarization has a prescribed azimuth angle $\alpha+90°$, the photodetector 0-224 detects a linearly polarized component whose polarization has a prescribed azimuth angle $\alpha+45°$, and the photodetector 0-225 detects a left-handed circularly polarized component.

A light component that has passed through the non-polarizing beam splitter 0-202 is further split by the non-polarizing beam splitter 0-203. A light component reflected by the non-polarizing beam splitter 0-203 passes through the polarization selecting means 0-212 which is a polarizing plate that transits a linearly polarized component whose polarization has the prescribed azimuth angle $\alpha$, and is detected by the photodetector 0-222. A light component that has passed through the non-polarizing beam splitter 0-203 passes through the polarization selecting means 0-213 which is a polarizing plate that transits a linearly polarized component whose polarization has the azimuth angle α+90°, and is detected by the photodetector 0-223. A light component reflected by the non-polarizing beam splitter 0-202 is further split by the non-polarizing beam splitter 0-204. A light component that has passed through the non-polarizing beam splitter 0-204 passes through the polarization selecting means 0-214 which is a polarizing plate that transits a linearly polarized component whose polarization has the prescribed azimuth angle α+45°, and is detected by the photodetector 0-224. A light component reflected by the non-polarizing beam splitter 0-204 passes through the polarization selecting means 0-215 which is composed of a λ/4 plate whose azimuth angle is set at 0° and a polarizing plate that transits a linearly polarized component whose polarization has the azimuth angle α+45°, and is detected by the photodetector 0-225.

Assume that the intensities of light components detected by the photodetectors 0-222 to 0-225 are represented by I1-I4, respectively. Then, Stokes parameters S0-S3 which present polarization states of light components incident on the polarization detecting section 0-200a can be obtained according to the following equations and the polarization states can thus be determined completely. In addition to the above-mentioned polarization-related physical quantities, the degree of polarization, the ellipticity, etc. can be calculated on the basis of the Stokes parameters S0-S3.

$$S0=I1+I2$$

$$S1=I1-I2$$

$$S2=2\times I3-(I1+I2)$$

$$S3=2\times I4-(I1+I2)$$

A configuration for detecting three different polarization components can easily be conceived from FIGS. 22(*a*) and 22(*b*). Polarization states of light components incident on the polarization detecting section 0-200a can be determined by detecting, as three different linearly polarized components, a linearly polarized component whose polarization has a prescribed azimuth angle α around the detection system optical axis 0-14, a linearly polarized component whose polarization has a prescribed azimuth angle α+45°, and a left-handed circularly polarized component and assuming that the light components incident on the polarization detecting section 0-200a are completely polarized light.

FIGS. 23(*a*) and 23(*b*) and FIGS. 24(*a*) and 24(*b*) show other exemplary configurations, different from the configurations of FIGS. 22(*a*) and 22(*b*), of the polarization detecting section 0-200a.

FIG. 23(*a*) shows the configuration of a polarization detecting section 0-200a''' which employs birefringent wedges. The polarization detecting section 0-200a''' is composed of a frequency modulation image acquiring section 0-250 and a Fourier analyzing section 0-255. FIG. 23(*b*) shows the configuration of the frequency modulation image acquiring section 0-250. The frequency modulation image acquiring section 0-250 is composed of a prism element 0-251 in which the advanced phase axis is at a prescribed azimuth angle (assumed to be 0°) around the detection optical axis 0-14, the delayed phase axis is at an azimuth angle 90°, and the phase shift varies linearly toward the azimuth angle 90°, a prism element 0-252 in which the advanced phase axis is at an azimuth angle 45°, the delayed phase axis is at an azimuth angle 135°, and the phase shift varies linearly toward the azimuth angle 0°, a polarizing plate 253 which transmits a linearly polarized component whose polarization direction is at the azimuth angle 0°, and an image sensor 0-254. The image sensor 0-254 is disposed so as to detect an enlarged image formed by the objective lens 0-3a and the image-forming lens 0-5a after passage through the prism elements 0-251 and 0-252 and the polarizing plate 0-253. With the above configuration, an image signal of light in which respective polarization components are modulated spatially at different frequencies is output from the image sensor 0-254. The output image signal is subjected to a frequency analysis through FFT in the frequency analyzing section 0-255, whereby plural parameters corresponding to polarization states are obtained for each position in the image.

FIG. 24(*a*) shows the configuration of a polarization detecting section 0-200a'''' which employs a minute polarizing element array. The polarization detecting section 0-200a'''' is composed of an image sensor 0-261 and a minute polarizing element array 0-262 which is placed on the photodetecting surface of the image sensor 0-261. FIG. 24(*b*) shows the structure of the minute polarizing element array 0-262 in which the respective pixels transmit different polarization components. In the example of FIG. 24(*b*), one polarization state is obtained by one unit 0-267 which consists of four pixels, that is, a pixel 0-263 that transmits linearly polarized light whose polarization (azimuth angle: 0°) is parallel with the horizontal direction of the pixel arrangement of the image sensor 0-261, a pixel 0-264 that transmits linearly polarized light whose polarization (azimuth angle: 90°) is parallel with the vertical direction of the pixel arrangement of the image sensor 0-261, a pixel 0-265 that transmits linearly polarized light whose polarization has an azimuth angle 45°, and a pixel 0-266 that transmits linearly polarized light whose polarization has the azimuth angle 45° while giving a phase delay of 90° to linearly polarized light whose polarization has the azimuth angle 0°.

One method for producing such a minute polarizing element array 0-262 is as follows. A thin-film polarizing plate whose thickness is on the order of microns to submicrons is placed on an imaging device or a substrate, and unnecessary portions are etched away according to the pixel size. Then, patterning is repeated in a similar manner while thin-film polarizing plates or wavelength plates having different major-axis directions are placed one on another. According to another method, a fine lattice whose pitch is shorter than the wavelength of light used is formed by patterning, whereby optical anisotropy is provided on a pixel-by-pixel basis. If the optical resolution (i.e., the diameter of a circle of confusion) which is determined by the image-forming performance of the objective lens 0-3a and the image-forming lens 0-5a is made equivalent to or higher than a value corresponding to the total width of four pixels (one unit) which determine a polarization state, the influence of image surface intensity variations between the four pixels can be reduced and highly accurate polarization measurement can thus be enabled.

A field of view on the inspection subject substrate W which is determined by the objective lens 0-3a, the image-forming lens 0-5a, and the polarization detecting section 0-200a'''' is moved relative to the inspection subject substrate W by moving the X-Y-Z-θ stage 0-11 in the X-direction and the Y-direction. Polarization component detection signals can be obtained from all or part of the surface of the inspection subject substrate W by sequentially moving the X-Y-Z-θ stage 0-11 in the X-direction and the Y-direction.

FIGS. 25(*a*) and 25(*b*) show the configurations of examples of the signal processing section 0-300. FIG. 25(*a*)

shows a signal processing section 0-300' which is an implementation example of a method of performing defect judgment on the basis of differences between output signals of the polarization detecting section 0-200a' (see FIG. 22(a)) which correspond to adjoining chips, bearing the same patterns in design, on the inspection subject substrate W.

Figure 25A:
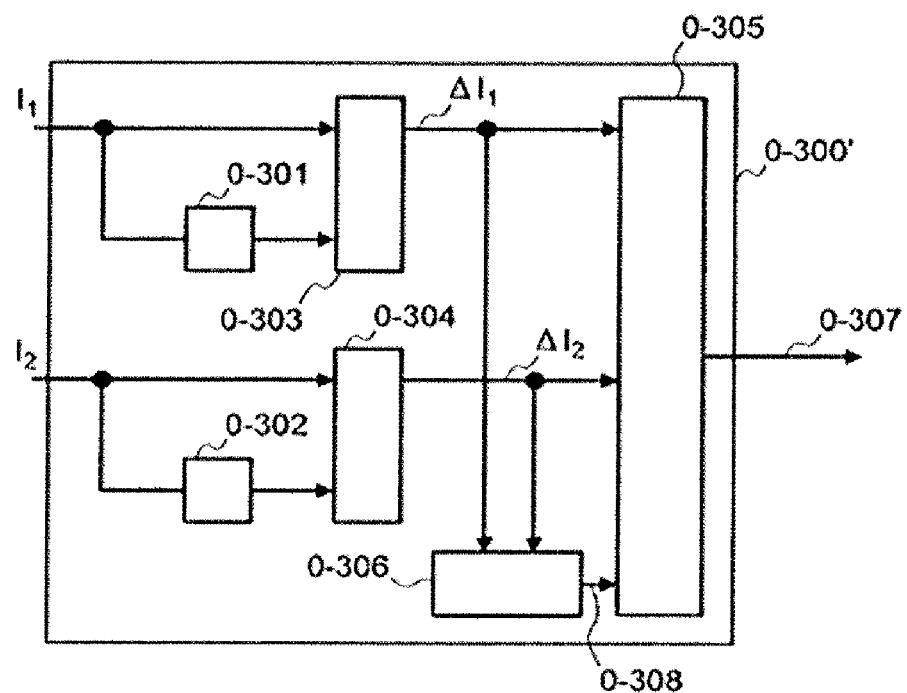
FIGS. 25(a) and 25(b) show general configurations of signal processing sections according to the third embodiment.
Figure 26A:
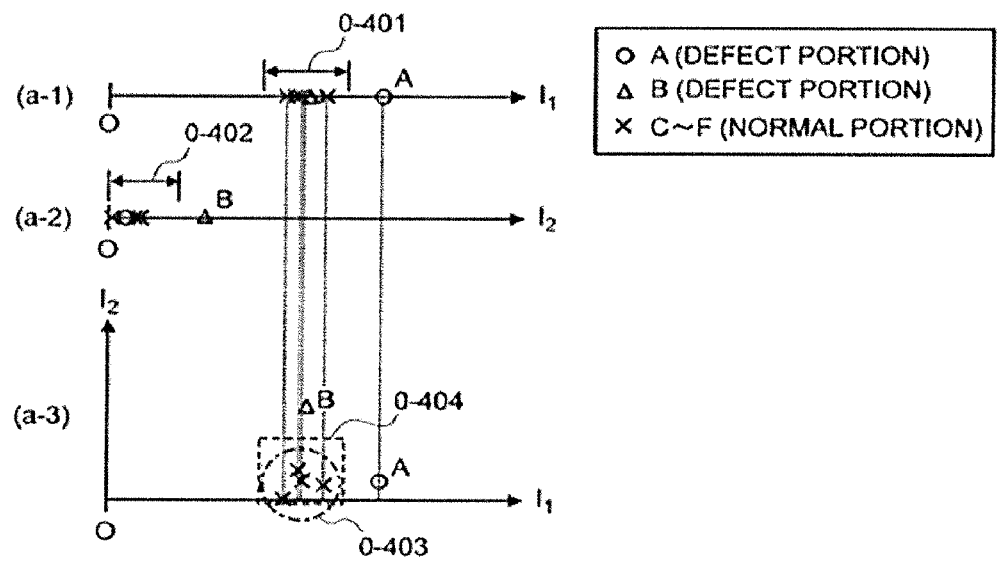
FIG. 26(a), which comprises FIGS. 26(a-1), 26(a-2), 26(a-3)
Figure 26B:
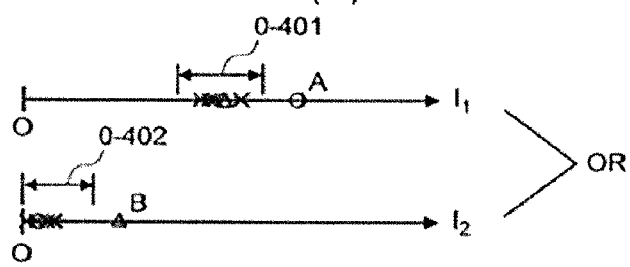
FIGS. 26(b) and 26(c) are conceptual diagrams showing a defect judging method based on two different polarization component signals which is employed by the signal processing section according to the third embodiment.
Figure 26C:

The signal processing section 0-300' of FIG. 25(a) is composed of delay memories 0-301 and 0-302, difference calculating sections 0-303 and 0-304, a defect judging section 0-305, and a defect judgment criterion calculating section 0-306. The signal processing section 0-300' outputs defect information 0-307 in response to signals $I_k$ (in FIG. 25(a), signals $I_1$ and $I_2$ corresponding to two polarization components) which are output from the polarization detecting section 0-200a'. Next, the operation will be described. The signal $I_1$ is input to the difference calculating section 0-303 and the delay memory 0-301. The delay memory 0-301 stores the signal $I_1$ and outputs it after delaying it by a one-chip processing time. The difference calculating section 0-303 receives the signal $I_1$ and the signal that is output from the delay memory 0-301 and corresponds to the adjacent chip, and outputs a difference signal $\Delta I_1$ between those signals. The thus-obtained difference signal $\Delta I_1$ is input to the defect judging section 0-305 and the defect judgment criterion calculating section 0-306. Likewise, a difference signal $\Delta I_2$ is obtained between the signal $I_2$ corresponding to a polarization component that is different from the polarization component corresponding to the signal $I_1$ and a signal corresponding to the adjacent chip, and is input to the defect judging section 0-305 and the defect judgment criterion calculating section 0-306. The defect judgment criterion calculating section 0-306 produces a defect judgment criterion 0-308 on the basis of the adjoining chips difference signals $\Delta I_1$ and $\Delta I_2$. The defect judging section 0-305 performs defect judgment on the basis of the received adjoining chips difference signals $\Delta I_1$ and $\Delta I_2$ according to the defect judgment criterion 0-308, and outputs defect information 0-307.

Figure 25B:
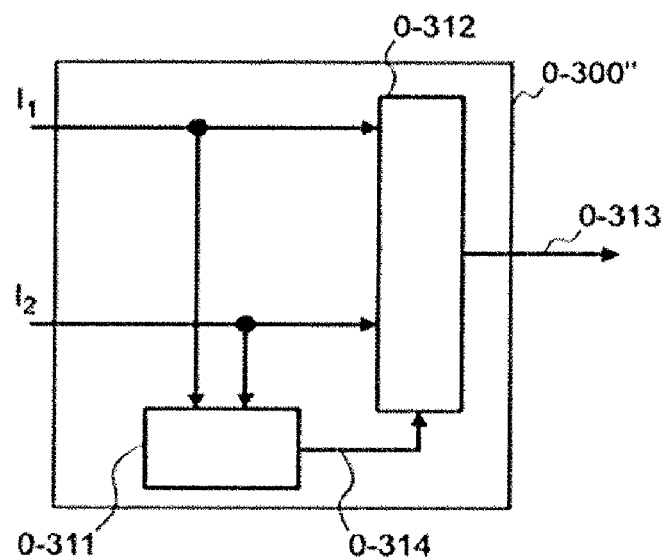

FIG. 25(b) shows the configuration of a signal processing section 0-300" which is an implementation example of a method of performing defect judgment on the basis of a series of signals (image signals) that are output from the polarization detecting section 0-200a' (see FIG. 22(a)) and correspond to a prescribed region on the inspection subject substrate W. An image signal $I_1$ that is output from the polarization detecting section 0-200a' corresponds to a signal obtained by detecting a prescribed polarization component for each position in a prescribed region on the inspection subject substrate W. Likewise, an image signal $I_2$ that is output from the polarization detecting section 0-200a' corresponds to a signal obtained by detecting a prescribed polarization component (different than in the image signal $I_1$) for each position in the prescribed region on the inspection subject substrate W. The image signals $I_1$ and $I_2$ are input to a defect judgment criterion calculating section 0-311 and a defect judging section 0-312. The defect judgment criterion calculating section 0-311 produces a defect judgment criterion 0-314 on the basis of the image signals $I_1$ and $I_2$. The defect judging section 0-312 performs defect judgment on the basis of the image signals $I_1$ and $I_2$ according to the defect judgment criterion 0-314, and outputs defect information 0-313.

A modification is possible in which the defect judgment criterion calculating section 0-306 or 0-311 is equipped with a memory and calculates defect judgment criterion 0-308 or 0-314 on the basis of previously detected polarization component detection signals obtained from positions, corresponding to each other, of plural chips. The defect information 0-307 or 0-313 which is output from the signal processing section 0-300' or 0-300" includes defect positions, a defect portion difference image, defect portion difference images of respective polarization components, defect feature quantities calculated from a defect portion difference image, defect classification results, etc. The defect classification may be made in the defect judging section 0-305 or 0-312 or made on the basis of the defect information 0-307 or 0-313 in the computing section 0-8.

The configuration of each of the signal processing sections 0-300' and 0-300" has been described above in the case of processing signals $I_1$ and $I_2$ corresponding to two polarization components that are output from the polarization detecting section 0-200a' of FIG. 22(a). However, the configuration of FIG. 25(a) or 25(b) can also be applied to the case of detecting signals corresponding to four polarization components that are output from the polarization detecting section 0-200a" of FIG. 22(b), the polarization detecting section 0-200a''' of FIGS. 23(a) and 23(b) or the polarization detecting section 0-200a'''' of FIGS. 24 (a) and 24(b). That is, a configuration for processing image signals $I_1$-$I_4$ corresponding to four polarization components can easily be realized by modifying the circuit configuration for processing image signals $I_1$ and $I_2$ (see FIG. 25(a) and 25(b)) to enable processing on four input signals.

Figure 28A:
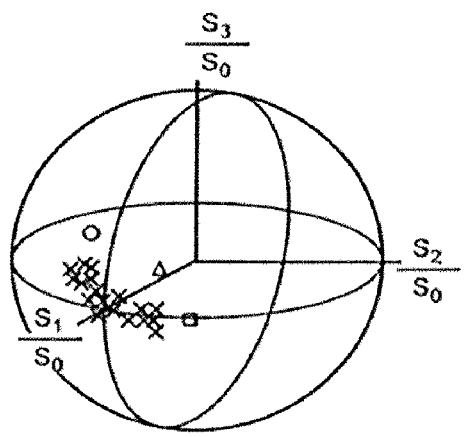
FIGS. 28(a)-28(c) are conceptual diagrams showing a defect judging method based on three physical quantities calculated from plural different polarization component signals which is employed by the signal processing section according to the third embodiment.
Figure 28B:
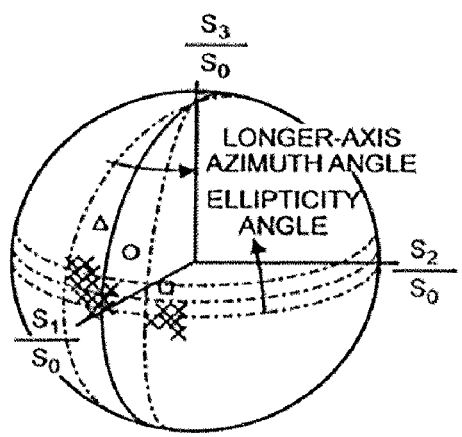
Figure 28C:
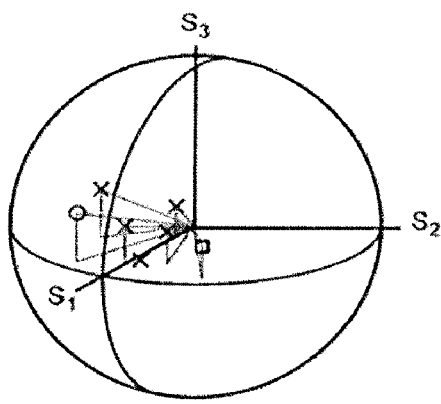

A defect judgment criterion calculating method of each of the defect judgment criterion calculating sections 0-306 and 0-311 (these symbols will be omitted below) and a defect judging method of each of the defect judging sections 0-305 and 0-312 (these symbols will be omitted below will be described below with reference to FIGS. 26(a), 26(a-1), 26(a-2), 26(a-3), 26(b) and 26(c) to FIGS. 28(a)-28(c).

First, a method for performing defect judgment using signals obtained by detecting two different polarization components will be described with reference to FIGS. 26(a), 26(a-1), 26(a-2), 26(a-3), 26(b) and 26(c).

FIGS. 26(a-1) and 26(a-2) show a conventional technique for performing defect judgment using only a single polarization component. FIG. 26(a-1) shows a distribution of polarization component signals $I_1$. Symbols A-F denote polarization component signals $I_1$ corresponding to respective chips which are stored in the defect judgment criterion calculating section. It is seen from the distribution of symbols A-F corresponding to individual plotted marks "◯," "△", and "x" that many signals are included in an $I_1$ value range 0-401 and only one signal A is located outside the range 0-401. The range 0-401 corresponds to a defect judgment criterion which is calculated from statistical values such as a average value and a standard deviation of the distribution of the plotted marks. If a signal located inside the range 0-401 is judged as corresponding to a normal portion and a signal located outside the range 0-401 is judged as corresponding to a defect portion, it is judged correctly that the signal A corresponds to a defect portion and signals C-F correspond to normal portions. However, the signal B is judged erroneously as corresponding to a normal portion.

On the other hand, FIG. 26(a-2) shows a distribution of polarization component signals $I_2$. If defect judgment is performed by calculating a range 0-402 (defect judgment criterion) in the same manner as in the case of FIG. 26(a-1), it is judged correctly that the signal B corresponds to a defect portion and signals C-F correspond to normal portions. However, it is judged erroneously that the signal A corresponds to a normal portion.

FIG. 26(a-3) illustrates a method for performing defect judgment using two different polarization components according to the third embodiment. In FIG. 26(a-3), the horizontal axis and the vertical axis represents the polarization component signals $I_1$ and $I_2$, respectively, and polarization component signals ($I_1$, $I_2$) are plotted which are stored in the defect judgment criterion calculating section as signals corresponding to plural chips. A rectangular region 0-404 which includes many of plotted points is calculated as a defect judgment criterion using average values and standard deviations of the distribution of the plotted points. The defect judging section judges that a signal located inside the rectangular region 0-404 corresponds to a normal portion and a signal located outside the rectangular region 0-404 (i.e., located in an excessively deviated range) corresponds to a defect portion. In this case, it can be judged without fail that each of the signals A and B corresponds to a defect portion and the signals C-F correspond to normal portions. Alternatively, a circular region 0-403 may be calculated as a defect judgment criterion using average values and standard deviations of the distribution of the plotted points. This also enables correct judgment.

FIG. 26(*b*) shows an alternative method. A judgment criterion J1 that a signal that is plotted outside the range 0-401 (i.e., $I_1$<Th1− or $I_1$>Th1+, where Th1− and Th1+ are the lower limit and the upper limit of the range 0-401, respectively) should be judged as corresponding to a defect is applied to polarization component signals $I_1$. A judgment criterion J2 that a signal that is plotted outside the range 0-402 (i.e., $I_2$<Th2− or $I_2$>Th2+, where Th2− and Th2+ are the lower limit and the upper limit of the range 0-402, respectively) should be judged as corresponding to a defect is applied to polarization component signals $I_2$. A final defect judgment criterion is that one of the judgment criteria J1 and J2 is satisfied (J1 or J2). Also in this case, correct judgment is possible as in the case of the above method. This is equivalent to the defect judgment criterion that a signal that is plotted outside the rectangular region 0-404 should be judged as corresponding to a defect.

FIG. 26(*c*) shows another alternative method. Values obtained by performing a prescribed computation processing on polarization component signals $I_1$ and $I_2$ are plotted. Defect judgment is performed by defining a range to be used for judging whether each plotted point corresponds to a normal portion or a defect portion. FIG. 26(*c*) shows an example that a formula $f(I_1, I_2)=(I_1−a)^2+(I_2−a)^2$ is calculated for polarization component signals $I_1$ and $I_2$ and results are plotted. A signal that is plotted outside a range 0-405 (f ($I_1$, $I_2$)>Th) is judged as corresponding to a defect. This method also enables correct judgment like the above methods. This is equivalent to the defect judgment criterion that a signal that is plotted outside the circular region 0-403 should be judged as corresponding to a defect. In general, where a defect judgment criterion is written by using an Nth-order formula of $I_1$ and $I_2$, the issue comes down to a problem of plotting signals on a plane defined by axes $I_1$ and $I_2$ and judging whether the signals correspond to a normal portion or a defect portion depending on whether they are located inside an Nth-order curve.

Defect judgment can also be performed by employing, as axes, physical quantities obtained on the basis of plural polarization component signals and plotting polarization component signals. As shown in FIG. 27(*a*), physical quantities obtained by performing arbitrary computations on plural polarization component signals are employed as respective axes.

FIG. 27(*b*) shows an example in which the physical quantities are the total light intensity (horizontal axis) and the ellipticity of polarization (vertical axis). In the case of scattering by a particulate defect such as a foreign particle, it is known that scattered light of linearly polarized illumination light is linearly polarized light in a Rayleigh scattering range in which the particle diameter is shorter than the light wavelength and that scattered light of linearly polarized illumination light is elliptically polarized light in a Mie scattering range in which the particle diameter is equivalent to or longer than the light wavelength. Therefore, the ellipticity of the polarization components of detected scattered light tends to increase as the defect dimension increases. This makes it possible to estimate a defect dimension on the basis of the ellipticity of polarization components corresponding to a detected defect portion.

FIG. 27(*c*) shows an example in which the physical quantities are the total light intensity (horizontal axis) and the longer-axis azimuth angle of polarization (vertical axis) It is known that the polarization direction of reflection-scattered light may be different from that of illumination light depending on the type of defect or pattern. In the example of FIG. 27(*c*), a foreign particle and a scratch are discriminated from each other on the basis of the longer-axis azimuth angle of polarization components corresponding to a defect.

FIG. 27(*d*) shows an example in which an amplitude reflectance ratio $\Psi$ and a phase difference $\Delta$ used in ellipsometry are calculated from a polarization state of illumination light (known physical quantity) and plural detected polarization component signals and are used as the horizontal axis and the vertical axis. Pieces of information relating to a thickness and a refractive index of a thin film at each position are obtained from these physical quantities, and hence processing can be performed on the basis of these pieces of information.

FIGS. 28(*a*)-28(*c*) show examples in which quantities based on three physical quantities obtained from plural polarization component signals are employed as axes and plural polarization component signals or values obtained through computations from them are plotted. FIG. 28(*a*) shows an example in which the polarization detecting section 0-200*a* acquires four different polarization component signals, calculate Stokes parameters S0-S3, and employs, as axes, the Stokes parameters S1-S3 as normalized by the Stokes parameter S0. This corresponds to a case that polarization states are indicated in connection with a Poincaré sphere having a radius 1. A point corresponding to a polarization state is plotted on the Poincaré sphere if it is complete polarization and inside the Poincaré sphere if it is partial polarization.

Defect judgment is performed by calculating a region (defect judgment criterion) in the three-dimensional space to be used for judging whether each plotted point corresponds to a defect portion or a normal portion. Since normalization is performed by the light intensity S0, the defect judgment is not affected by brightness variation of original scattered light even if it is large. Defect judgment based on a distribution which reflects polarization state differences is thus realized. As shown in FIG. 28(*b*), in the case where the S1-S2 plane is employed as the equatorial plane in the Poincaré sphere representation, the latitude corresponds to the ellipticity angle (arctangent of ellipticity) and the longitude corresponds to two times the longer-axis azimuth angle of polarization. Therefore, estimation of a defect dimension and classification into defect types are possible as in the cases of FIGS. 27(*b*) and 27(*c*). As shown in FIG. 28(*c*), plotting S1-S3 as they are without normalization by S0 makes it possible to perform defect detection on the basis of a distribution in which the light intensity is taken into consideration in addition to the polarization state.

A first modification of the third embodiment will be described below with reference to FIGS. 29-32.

Figure 29:
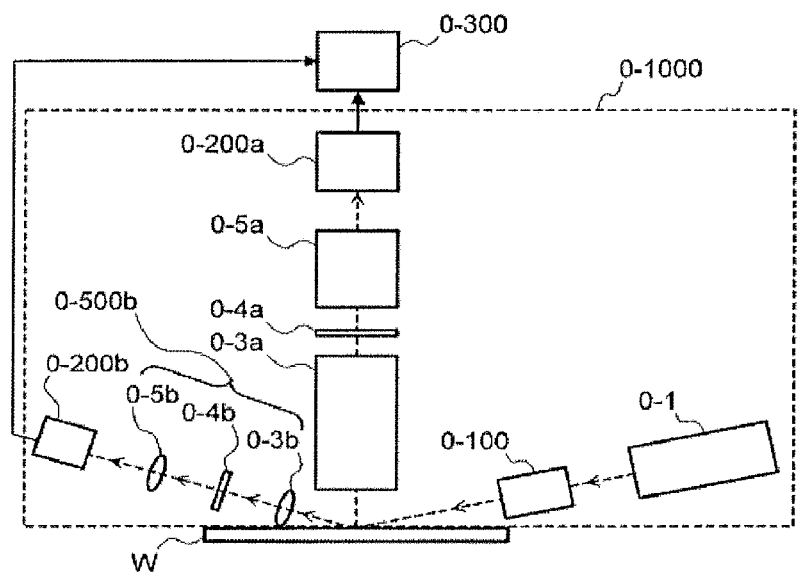
FIG. 29 shows a general configuration of an optical system of a first modification of the defect inspection apparatus according to the third embodiment.

FIG. 29 shows the configuration of the first modification. An object lens 0-3b, a spatial filter 0-4b, an image-forming lens 0-5b, and a polarization detecting section 0-200b are added to the configuration according to the third embodiment. The object lens 0-3b, the spatial filter 0-4b, the image-forming lens 0-5b constitute an oblique detection system 0-500b. A reflection-scattered light component having a different elevation and azimuth angle than one to shine on the objective lens 0-3a is guided by the oblique detection system 0-500b to the polarization detecting section 0-200b. The configuration of the polarization detecting section 0-200b can be the same as that of one of the above-described polarization detecting sections 0-200a' to 0-200a''''. Although it is desirable that the polarization detecting section 0-200b have the same configuration as the polarization detecting section 0-200a, this is not an absolute requirement. Like ones detected by the polarization detecting section 0-200a, plural polarization component signals detected by the polarization detecting section 0-200b are input to the signal processing section 0-300. Defect judgment is performed on the basis of the plural polarization component signals detected by the polarization detecting section 0-200a and the plural polarization component signals detected by the polarization detecting section 0-200b. Alternatively, a signal processing section 0-300b (not shown) may be provided separately from the signal processing section 0-300 so as to perform defect judgment on the basis of the plural polarization component signals detected by the polarization detecting section 0-200b independently of the signal processing section 0-300.

Figure 30:
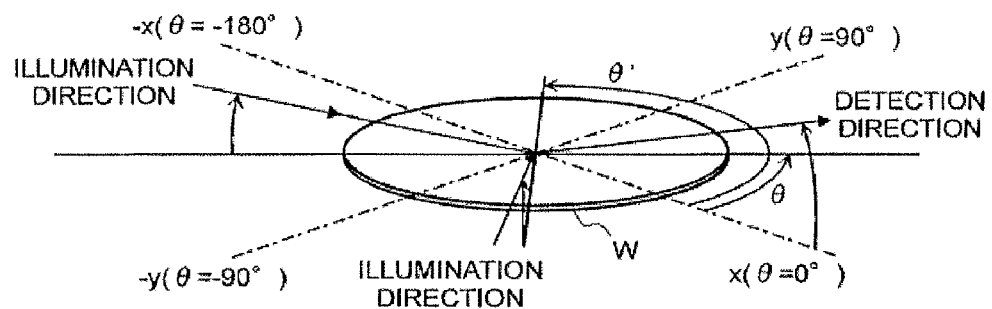
FIG. 30 is a schematic diagram showing a detection direction of an oblique detection system of the first modification of the defect inspection apparatus according to the third embodiment.

FIG. 30 shows a relationship between the detection direction and the illumination direction of the oblique detection system 0-500b. The oblique detection system 0-500b is disposed so that its detection direction coincides with the stage X-direction. The illumination azimuth angle can be set in the manner described with reference to FIGS. 21(*b*)-21(*d*). FIG. 30 shows a case that the illumination advancement azimuth angle θ with respect to the stage X-direction (θ being equal to 0° means that the illumination advancement direction is the same as the detection direction) is in a range of 0° to −90° and a case that θ is in a range of −90° to −180°. The arrangement that θ is in the range of 0° to −90° is suitable for detection of defects that are large relative to the wavelength because forward scattering light produced by such defects shines on the oblique detection system 0-500b. On the other hand, the arrangement that θ is in the range of −90° to −180° is suitable for detection of defects that are small relative to the wavelength because back scattering light produced by such defects shines on the oblique detection system 0-500b.

Figure 31:
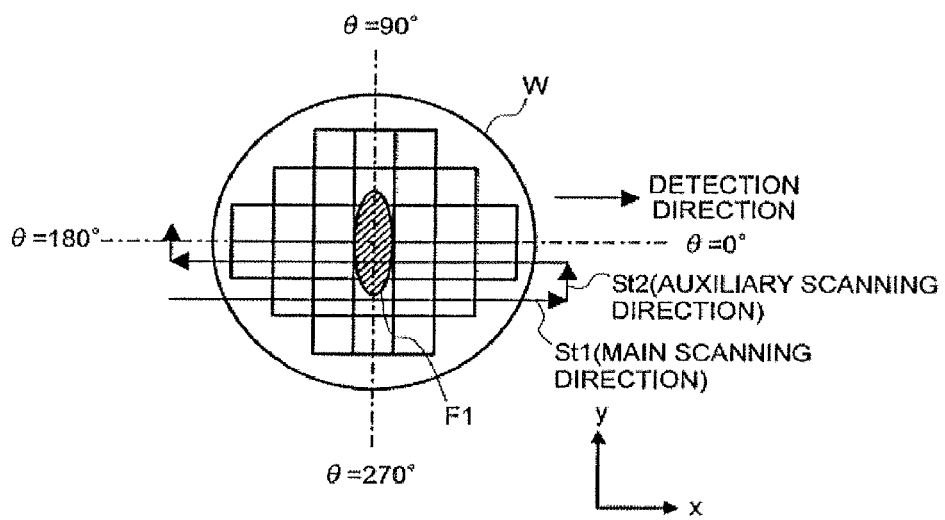
FIG. 31 is a schematic diagram showing relationships between the detection direction of the oblique detection system, the stage scanning directions, and the longitudinal direction of an illumination region of the first modification of the defect inspection apparatus according to the third embodiment.

FIG. 31 shows relationships between the detection direction of the oblique detection system 0-500b, the main scanning direction St1 and the auxiliary scanning direction St2 of the X-Y-Z-θ stage 0-11, and the longitudinal direction of an illumination region F1. Setting the longitudinal direction of the illumination region F1 perpendicular to the main scanning direction St1 makes it possible to scan the entire surface of the inspection subject substrate W efficiently. Setting the detection direction parallel with the main scanning direction St1 and perpendicular to the longitudinal direction of the illumination region F1 makes it possible to inspect the inspection subject substrate W at a high throughput in the case where the photodetector of the oblique detection system 0-500b is a linear sensor.

Figure 32:
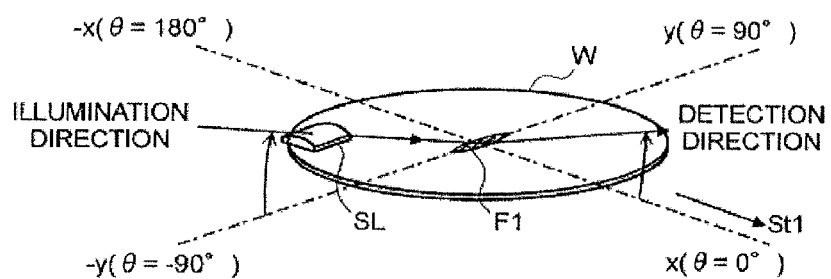
FIG. 32 is a schematic diagram showing a configuration example of the first modification of the defect inspection apparatus according to the third embodiment in which the illumination region forming method is different than in the third embodiment.

FIG. 32 shows a configuration example which is different from the one shown in FIG. 30 in the illumination direction and the detection direction. Illumination light is applied from a direction that is perpendicular to the stage main scanning direction St1, and a cylindrical lens SL is disposed so that the rotation axis of its cylindrical surface is set parallel with the stage main scanning direction St1 and the longitudinal direction of the illumination region F1 is perpendicular to the stage main scanning direction St1. This arrangement makes it possible to make the width of the illumination region F1 in its shorter direction smaller than in the case where the plane of the illumination elevation is inclined in the illumination light narrowing direction. Furthermore, the detection sensitivity is made stable because the position variation of the illumination region F1 in its shorter direction due to very small fluctuation of the X-Y-Z-θ stage 0-11 in the Z direction during a scan can be suppressed.

FIG. 33 shows the configuration of a version of the optical system 0-1000 according to a second modification of the third embodiment. Illumination light emitted from a light source 0-1 passes through an illumination optical system 0-100' and is guided to an illumination region F1 on the inspection subject substrate W by a half mirror 0-150 and an objective lens 0-3a. In this configuration, a polarization detecting section 0-200 detects a bright-field image. A detection signal that is output from the polarization detecting section 0-200 is processed in the signal processing section 0-300 and defects are thereby detected.

FIG. 34 shows the configuration of a version of the optical system 0-1000 according to a third modification of the third embodiment. Illumination light emitted from a light source 0-1 passes through an illumination optical system 0-100' and is guided to an illumination region F1 on the inspection subject substrate W by a dark-field objective lens 0-3a'. In this configuration, a polarization detecting section 0-200 detects a ring illumination dark-field image.

FIG. 35 shows the configuration of the illumination optical system 0-100'. The intensity of illumination light is controlled by an attenuator 0-101'. A polarizing plate 0-102' is provided when necessary, whereby illumination light emitted from the light source 0-1 is given linear polarization. The polarization state of illumination light is set arbitrarily by a λ/2 plate 0-103' and a λ/4 plate 0-104' which are rotatable about the optical axis. Where the light source 0-1 is a laser light source, generation of speckle noise can be suppressed by disposing a speckle reducing means 0-111'. Examples of the speckle reducing means 0-111' are a means for generating plural light beams having different optical path lengths and superimposing them on each other by using plural optical fibers having different optical path lengths, a quartz plate, a glass plate, or the like and a means for causing the illumination light to pass through a rotary diffusing plate 0-105'.

Figure 36:
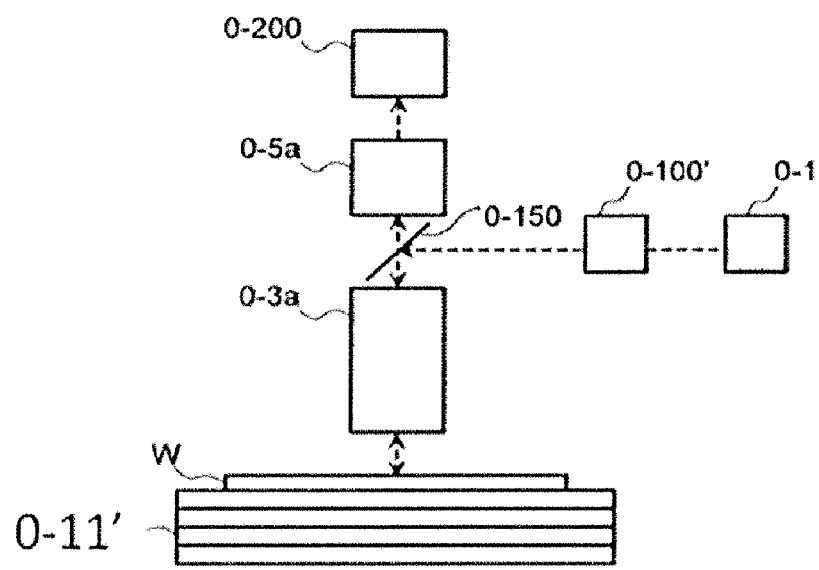
FIG. 36 shows a general configuration of an optical system and a stage of the fourth modification of the defect inspection apparatus according to the third embodiment.

FIG. 36 shows the configurations of versions of the optical system 0-1000 and the X-Y-Z-θ stage 0-11 according to a fourth modification of the third embodiment. A light source 0-1' is a strobe light source which emits light intermittently. More specifically, the use of a pulsed laser, an LD-pumped Q switch pulsed laser, a lamp-pumped Q switch pulsed laser, a flash lamp, or the like is appropriate. An area sensor is used as the photodetector of a polarization detecting section 0-200. With this configuration, a two-dimensional image without distortion can be acquired and highly accurate chip comparison is enabled by performing strobe shooting in such a manner that the light emission of the light source 0-1', the scanning of the X-Y-Z-θ stage 0-11, and the signal storage of the photodetector are synchronized with each other. If an r-θ rotary stage 0-11' is used in place of the X-Y-Z-θ stage 0-11, the entire surface of the inspection subject substrate W can be scanned faster than by the XY scanning.

Figure 37:
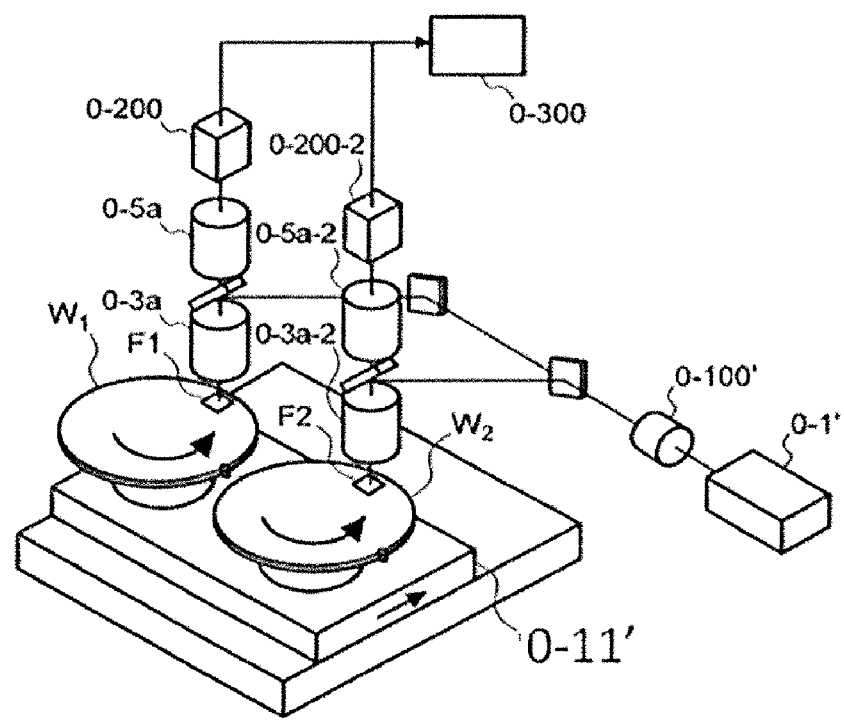
FIG. 37 shows a general configuration of an optical system and a stage of the fifth modification of the defect inspection apparatus according to the third embodiment.

FIG. 37 shows the configuration of a fifth modification of the third embodiment. The same patterns, in design, are formed on inspection subject substrates W1 and W2. Light emitted from a light source 0-1' is split, and split light beams shine on the inspection subject substrates W1 and W2 which are mounted on an r-θ rotary stage 0-11'. Reflection-diffused light from the inspection subject substrate W1 shines on a polarization detecting section 0-200 via an objective lens 0-3a and an image-forming lens 0-5a. Reflection-diffused light from the inspection subject substrate W2 shines on a polarization detecting section 0-200-2 via an objective lens 0-3a-2 and an image-forming lens 0-5a-2. Strobe shooting is performed in such a manner that the light emission of the light source 0-1', the scanning of the r-O rotary stage 0-11', and the signal storage of the photodetectors in the polarization detecting sections 0-200 and 0-200-2 are synchronized with each other.

Where rotary scanning is performed by using the r-θ rotary stage 0-11', as shown in FIG. 38(*a*), the polarization state of illumination light and the direction of the polarization detecting section 0-200 or 0-200-2 with respect to the patterns on the inspection subject substrate W, W1, or W2 vary depending on the view field position on the inspection subject substrate W, W1, or W2. The polarization state of illumination light with respect to the patterns formed on the inspection subject substrate W, W1 or W2 can be kept the same by making the polarization state of illumination light polarizationless or circular polarization which is symmetrical about the optical axis or rotating the longer-axis direction of the polarization of illumination light according to the stage rotation angle which corresponds to the view field position. Furthermore, as shown in FIG. 38(*b*), the influence of the rotation of the direction of the polarization detecting section 0-200 or 0-200-2 with respect to the patterns formed on the inspection subject substrate W, W1, or W2 can be eliminated by correcting the azimuth angle of a detected polarization component (i.e., rotating its direction) according to the stage rotation angle which corresponds to the view field position. This makes it possible to inspect the entire surface of the inspection subject substrates W, W1, and W2 with constant sensitivity irrespective of the rotation of the direction of the polarization detecting section 0-200 or 0-200-2 with respect to the patterns formed on the inspection subject substrates W, W1, and W2.

Embodiment 4 of the Invention for Solving the Second Problems

Next, an optical system according to a fourth embodiment which replaces the illumination optical system 0-100 in the case where a pulsed UV laser light source 0-2001 is used in place of the light source 0-1 in the configuration of FIG. 20 and FIGS. 21(*a*)-21(*d*) will be described with reference to FIG. 39, FIG. 40(*a*), FIG. 40(*b*), FIG. 40(*c*), FIG. 41(*a*), FIG. 41(*b*) and FIG. 42.

Where the light source 0-2001 (pulsed UV laser) is used, to obtain sufficiently strong scattered light to detect very small foreign particles (defects) measuring about 10 nm, for example, it is necessary to increase the light quantity of illumination pulse laser light. However, as a result, the peak value (maximum output power) becomes very large for the average output power of the pulsed laser. For example, in the case of a laser having an average output power of 2 (W), a light emission frequency of 100 (MHz), a pulse interval of 10 (ns), and a pulse width of 10 (ps), the peak value (maximum output power) becomes as large as 2 (kW) and a sample may be damaged. Therefore, it is desirable to lower the peak value (maximum output power) while maintaining the average output power.

This embodiment employs the following method to lower the peak value while maintaining the average output power.

As shown in FIG. 39, a laser beam L0 emitted from the light source 0-2001 is expanded by a beam expanding optical system 0-2016 and input to a pulse light dividing optical system 0-2017. In the pulse dividing optical system 0-2017, the laser beam is split into beams that go along plural optical paths having different optical path lengths and are then combined together. In this manner, a laser beam of one pulse emitted from the light source 0-2001 is divided into plural pulse beams whose peak values are lowered. The plural divisional pulse laser beams are input to a splitting optical element 0-2018 (corresponds to the optical system shown in FIG. 21(*a*) and 21(*b*) that consists of the mirror M1-M9 and the cylindrical lenses 0-109 to 0-111) and are guided so as to go along one of optical paths L1-L3 (correspond to the optical paths 0-106 to 0-108 shown in FIGS. 21(*a*) and 21(*b*)). Slit-shaped beams are thereby formed and illuminate a slit-shaped region 0-2100 on the wafer W.

Since plural divisional pulse laser beams are applied to the inspection subject substrate W, imaging can be performed in such a manner that speckle noise caused by laser beams is average in time and hence a noise-reduced image can be obtained. For example, if a UV pulse laser beam having an emission frequency 100 MHz is divided into plural beams and applied to the inspection subject substrate W under conditions that the movement speed in the X-direction (see FIG. 30) of the X-Y-Z-θ stage 0-11 mounted with the inspection subject substrate W is 20 cm/s and the size of the detection field of view per pixel in the case where the detector 0-220 or 0-221 of the polarization detecting section 0-200a' shown in FIG. 22(*a*) is a time-integration-type (CCD or CMOS) linear image sensor is 1 μm, laser beams of more than hundreds of pulses are applied to each region to be detected by one pixel of the detector 0-220 or 0-221.

Figure 40A:
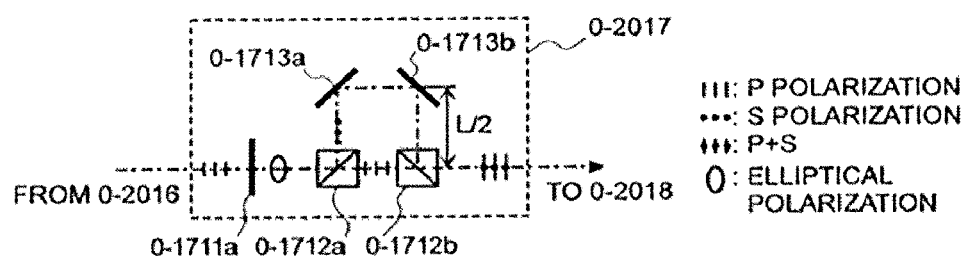
FIG. 40(a) is a block diagram showing a general configuration of a pulse light splitting optical system according to the fourth embodiment.
Figure 40B:
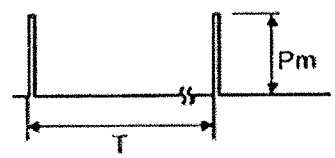
FIG. 40(b) is a waveform diagram of pulse laser beams emitted from a laser light source.
Figure 40C:
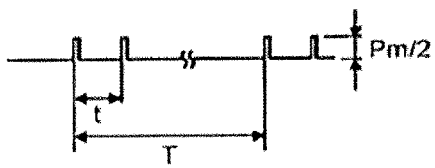
FIG. 40(c) is a waveform diagram showing how a one pulse laser beam emitted from the laser source is split into two pulse beams.

FIG. 40(*a*) shows an example of the pulse light dividing optical system 0-2017. In this example, the pulse light dividing optical system 0-2017 is composed of a λ/4 plate 0-1711a, polarizing beam splitters (PBSs) 0-1712a and 0-1712b, and mirrors 0-1713a and 0-1713b. A linearly polarized (in this example, p-polarized) laser beam that has been expanded by the beam expanding optical system 0-2016 is converted into elliptically polarized light by the λ/4 plate 0-1711a and then split into p-polarized light and s-polarized light by the polarizing beam splitter 0-1712a. The p-polarized component passes through the polarizing beam splitters 0-1712a and 0-1712b. The other split component, that is, the s-polarized component, is reflected by polarizing beam splitter 0-1712a, the mirrors 0-1713a and 0-1713b, and the polarizing beam splitter 0-1712b and thereby comes to go along the same optical axis as the p-polarized component that has passed through the polarizing beam splitters 0-1712a and 0-1712b. If the interval between the polarizing beam splitter 0-1712a and the mirror 0-1713a and the interval between the polarizing beam splitter 0-1712b and the mirror 0-1713b are set at L/2 (m), the s-polarized light and the p-polarized light are given an optical path difference L (m). A time difference $$t(s)=L(m)/c(m/s)$$

occurs between the s-polarized light and the p-polarized light, where c (m/s) is the speed of light. If two pulse beams which are emitted from the laser light source 0-2001 at a time interval T (see FIG. 40(*b*)) is divided in time, each laser beam pulse can be divided into two pulses (p-polarized pulse and s-polarized pulse) having the time interval t and the peak value can be halved.

For example, if a laser having a pulse interval 10 ns ($10^{-8}$ s) and a pulse width 10 ps ($10^{-11}$ s) is used and the interval between the polarizing beam splitter 0-1712a and the mirror 0-1713a and the interval between the polarizing beam splitter 0-1712b and the mirror 0-1713b are set at 15 cm (0.15 m), the time difference between the s-polarized component and the p-polarized component becomes 1 ns ($10^{-9}$ s). That is, the wafer surface is illuminated with peak-value-halved, 1-nm-spaced pulse laser beams two times (one time by each of p-polarized light and s-polarized light) in 10 ns.

If the ratio between the s-polarized component and the p-polarized component of an incident beam to the polarizing beam splitter 0-1712a is set at 1:1 (circular polarization) by adjusting the rotation angle of the λ/4 plate 0-1711a, the s-polarized component and the p-polarized component of exit pulse beams from the polarizing beam splitter 0-1712b have different peak values due to losses (reflectance and transmittance) of the optical components used (polarizing beam splitters 0-1712a and 0-1712b and mirrors 0-1713a and 0-1713b) To reduce the maximum value of the peak values of the s-polarized and p-polarized pulse beams, it is necessary to make the peak values of those pulse beams approximately identical.

With the configuration of the pulse light dividing optical system 0-2017 shown in FIG. 40(a), whereas the p-polarized component is influenced by only the p-polarization transmittance Tp) of the polarizing beam splitters 0-1712a and 0-1712b, the s-polarized component is influenced by the s-polarization reflectance (Rs) of the polarizing beam splitters 0-1712a and 0-1712b and the s-polarization reflectance (Rm) of the mirrors 0-1713a and 0-1713b. The loss ratio P1 is given by $P1 = Ls/Lp = Rm^2 \times Rs^2/Tp^2$ where Ls and Lp are the loss of the s-polarized component and the loss of the p-polarized component, respectively.

Therefore, the peak values of the s-polarized component and the p-polarized component of exit beams from the polarizing beam splitter 0-1712b can be made approximately identical by adjusting the rotation angle of the λ/4 plate 0-1711a so that the ellipticity of the polarization of an incident beam to the polarizing beam splitter 0-1712a becomes approximately equal to the above loss ratio P1. A P-polarized component pulse beam and an s-polarized component pulse beam that have been separated from each other so as to have approximately the same peak values are applied to the wafer W with a time interval corresponding to the difference between the optical path lengths after going along one of the optical paths 0-106 to 0-108 shown in FIG. 21(a).

Figure 41A:
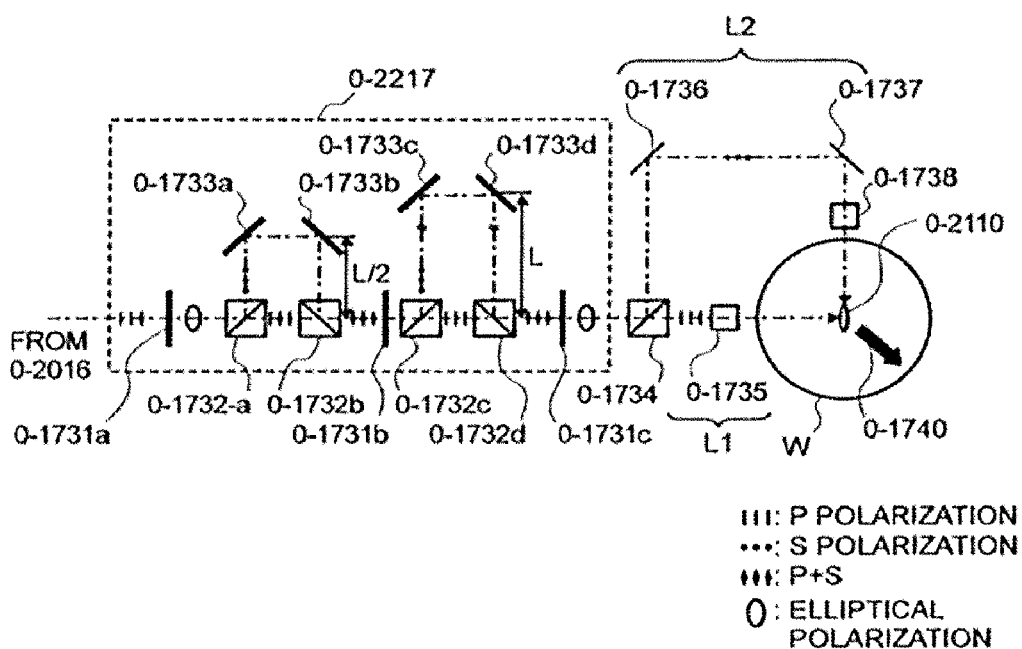
FIG. 41(a) is a block diagram showing a general configuration of a modification of the pulse light splitting optical system according to the fourth embodiment.

Although the above description is directed to the case of dividing a pulse beam into two beams using the pulse light dividing optical system 0-2017, a method for division into four beams as a modification (for increasing the number of divisional beams) of the pulse light dividing optical system 0-2017 will be described below with reference to FIGS. 41(a) and 41(b). A pulse light dividing optical system 0-2217 shown in FIG. 41(a) is configured by connecting two pulse light dividing optical systems 0-2017 of FIG. 40(a) in series. The interval between a polarizing beam splitter 0-1732c and a mirror 0-1733c of the second stage and the interval between a polarizing beam splitter 0-1732d and a mirror 0-1733d of the second stage are set two times the interval between the polarizing beam splitter 0-1732a and the mirror 0-1733a of the first stage and the interval between the polarizing beam splitter 0-1732b and the mirror 0-1733b of the first stage.

Exit beams from the first-stage polarizing beam splitter 0-1732b are a p-polarized pulse beam and an s-polarized pulse beam delayed form it. This pulse beam sequence is converted into circularly polarized beams by a λ/4 plate 0-1731b, whereby p-polarized beams that are ½, in intensity, of a pulse beam sequence that has passed through the λ/4 plate 0-1731b pass through the polarizing beam splitters 0-1732c and 0-1732d. And s-polarized beams that are ½, in intensity, of the pulse beam sequence that has passed through the λ/4 plate 0-1731b are reflected by the polarizing beams splitter 0-1732c, the mirrors 0-1733c and 0-1733d, and the polarizing beams splitter 0-1732d and thereby come to share the same optical axis with the p-polarized beams. In this manner, each pulse laser beam emitted from the light source 0-2001 is divided into four beams whose peak values are as small as ¼ of the peak value of the original pulse beam. More strictly, as described above, the peak values are smaller than ¼ of the original pulse beam because of the losses of the optical components.

In the configuration of FIG. 41(a), p-polarized pulse beams that have passed through the polarizing beam splitters 0-1732c and 0-1732d and s-polarized pulse beams that have been reflected by the mirror 0-1733d and the polarizing beam splitter and 0-1732d go along the same optical axis and are converted into circularly polarized beams by a λ/4 plate 0-1731c. The circularly polarized beams enter a polarizing beam splitter 0-1734, which causes the p-polarized beams and the s-polarized beams to take different optical paths. The thus-separated p-polarized component beams go along an optical path L1, are shaped by a cylindrical lens 0-1735 (corresponds to one of the cylindrical lenses 0-109 to 0-111 shown in FIG. 21(b)), and illuminate a line-shaped region 0-2110 on the wafer W.

On the other hand, the s-polarized beams that have been reflected by the polarizing beam splitter 0-1734 (the optical path is bent by 90°) go along an optical path L2, are reflected by mirrors 0-1736 and 0-1737 (the optical path is changed), shaped by a cylindrical lens 0-1738, and illuminate the line-shaped region 0-2110 on the wafer W from the direction perpendicular to the direction of the optical path L1 from which the p-polarized beams shine on the wafer W.

Figure 41B:
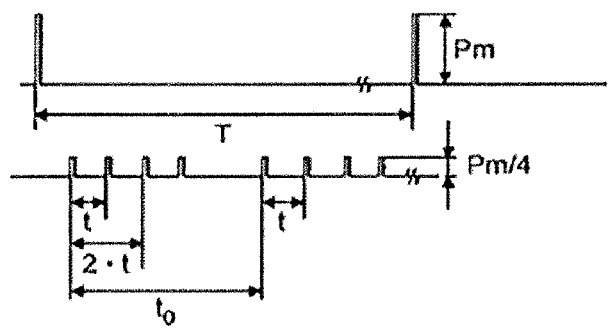
FIG. 41(b) is a waveform diagram showing how pulse beam splitting is performed.

Since the optical system is designed so that the optical paths L1 and L2 have different optical path lengths, the p-polarized beams and the s-polarized beams that illuminate the line-shaped region 0-2110 on the wafer W have a time difference $t_0$ which corresponds to the optical path length (see FIG. 41(b)) and hence shine on the wafer W with a deviation in timing. This prevents interference between the p-polarized beams and the s-polarized beams that illuminate the line-shaped region 0-2110 on the wafer W.

The photodetectors 0-220 and 0-221 detect reflection-scattered light beams produced by illumination light beams that originate from the laser light source 0-2001 and come from the 90°-deviated directions, in each one-pixel detection time. This makes it possible to reduce variation in detection sensitivity due to the difference in illumination direction and thereby detect finer foreign particle defects stably. Where the oblique detection system 0-500b shown in FIG. 29 is also used, the oblique detection system 0-500b detects reflection-scattered light traveling in an arrow direction 0-1740.

Figure 42:
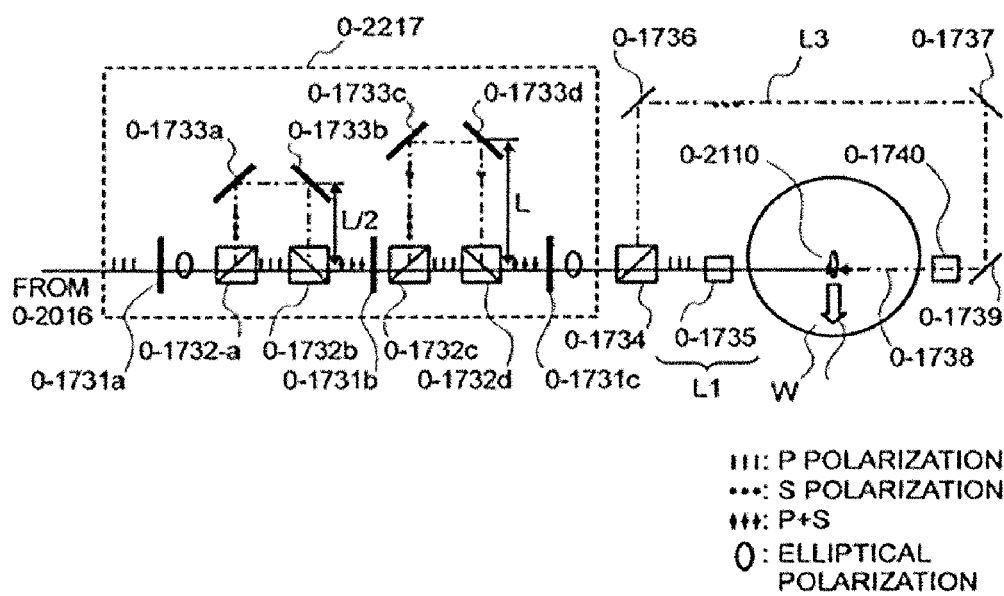
FIG. 42 is a block diagram showing a general configuration of another modification of the pulse light splitting optical system according to the fourth embodiment.

FIG. 42 shows a configuration which is different from the configuration of FIG. 41(a) in that the optical path L2 is replaced by an optical path L3. In this configuration, s-polarized beams that have been reflected by the polarizing beam splitter 0-1734 (the optical path is bent by 90°) are reflected by mirrors 0-1736, 0-1737 and 0-1739 (the optical path is changed) and shaped by a cylindrical lens 0-1740 in the optical path L3, and illuminate a line-shaped region 0-2110 on the wafer W from the direction opposite to the direction of the optical path L1.

The configurations of FIGS. 41(a) and 42 employ the λ/4 plate 0-1731c and the polarizing beam splitter 0-1734. Another configuration is possible in which the λ/4 plate 0-1731c is omitted and a non-polarizing beam splitter (not shown) is used in place of the polarizing beam splitter 0-1734. In this case, p-polarized beams and s-polarized beams shine on the wafer W with different timings from each of the optical paths L1 and L2 or L3. The photodetectors 0-220 and 0-221 detect reflection-scattered light beams that are produced as the wafer W is sequentially illuminated with p-polarized beams and s-polarized beams that come from the 90° or 180°-deviated direction in each one-pixel detection time. As a result, reflection-scattered light beams are detected from the wafer W that is illuminated under plural illumination conditions in each one-pixel detection time, whereby the detection sensitivity can be made higher than in the case of illumination under a single illumination condition. This makes it possible to detect finer foreign particle defects stably.

signals produced by the photodetectors 0-220 and 0-221 are processed by the signal processing section 0-300 in the same manner as described in the third embodiment, whereby defects are detected.

Although the fourth embodiment has been described with the assumption that the polarization detecting section 0-200a has the configuration of FIG. 22(a), any of the polarization detecting sections described above with reference to FIG. 22(b), FIGS. 23(a) and 23(b), and FIGS. 24(a) and 24(b) may be used.

The fourth embodiment makes it possible to detect, with high sensitivity, very fine defects that are about 0.1 μm or even smaller in size without damaging a wafer because peak-value-reduced UV pulse laser beams can be applied to the wafer.

As described above, the configurations according to the aspect of the invention for solving the second problems make it possible to detect, at high speed with high accuracy, fine defects on an inspection subject substrate bearing patterns that produce scattered light.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A defect inspection method comprising the steps of:
   acquiring images of a sample whose surface is formed with patterns by sequentially shooting inspection regions including a pattern;
   correcting, as pre-processing, the images taken by the sequential shooting;
   generating inspection images and reference images sequentially from the corrected images;
   extracting defect candidates on the sample using a set or sets of an inspection image and a reference image; and
   determining defects from the extracted defect candidates and classifying the defects,
   wherein the defect candidate extracting step comprises the substeps of:
      calculating a correction value for positioning the inspection image and the reference image of the same set;
      positioning the inspection image and the reference image with respect to each other on the basis of the calculated correction value; and
      extracting defect candidates by comparing the positioned inspection image and reference image using plural computing devices in such a manner that pieces of processing are performed in parallel by the plural computing devices, the plural computation processing devices and a parent computing device being connected to each other by a bidirectional data communication bus.

2. The defect inspection method according to claim 1, wherein images of the sample are acquired by plural detection optical systems; and wherein the defect candidate extracting step comprises the substeps of:
   calculating correction values for positioning the inspection image and the reference image of the same set for the plural respective detection optical systems on the basis of images acquired for the plural respective detection optical systems by processing, in parallel, with the plural computing devices, images of the same position on the sample acquired by the plural detection optical systems;
   positioning the inspection image and the reference image with respect to each other for the plural respective detection optical systems on the basis of the calculated correction values;
   calculating feature quantities of pairs of corresponding pixels of the positioned inspection image and reference image for the plural respective detection optical systems;
   forming a feature space by unifying sets of feature quantities calculated for the plural respective detection optical systems;
   finding pixels whose feature quantities are excessively deviated from a distribution in the feature space; and
   extracting, as defect candidates, the pixels whose feature quantities are excessively deviated from the distribution.

3. The defect inspection method according to claim 1, wherein the substep of extracting defect candidates by comparing the positioned inspection image and reference image calculates feature quantities of pairs of corresponding pixels of an image of an inspection subject pattern and an image of a reference pattern, decomposes the image into divisional areas according to the feature quantities of the pixels, and extracts pixels as defect candidates for each divisional area.

4. The defect inspection method according to claim 1, wherein the substep of extracting defect candidates by comparing the positioned inspection image and reference image calculates feature quantities of pairs of corresponding pixels of the positioned inspection image and reference image, finds pixels whose feature quantities are excessively deviated from a distribution of the calculated feature quantities, and extracts, as defect candidates, the pixels whose feature quantities are excessively deviated from the distribution of the calculated feature quantities.

5. The defect inspection method according to claim 4, wherein the feature quantities are a combination of plural feature quantities selected from brightness, contrast, a density difference, a brightness variance of nearby pixels, a correlation coefficient, a brightness increase or decrease from nearby pixels, and a second-order differential coefficient.

6. A defect inspection method for inspecting, for defects, a sample whose surface is formed with patterns, comprising the steps of:
   acquiring plural images, corresponding to plural respective detection optical systems, of an inspection region including a pattern on the sample by illuminating the inspection region and shooting the illuminated inspection region with the plural detection optical systems;

correcting, as pre-processing, the plural images of the inspection region taken by the plural respective detection optical systems;

generating sets of an inspection image and a reference image from the plural respective corrected images of the inspection region;

extracting defect candidates for each of the plural images of the inspection region by processing, in parallel, the sets of an inspection image and a reference image using plural computing devices that are connected to each other via a bidirectional data bus; and unifying sets of defect candidates extracted for the plural respective images of the inspection region.

7. The defect inspection method according to claim 6, wherein the unifying step unifies results of classification performed after the extraction of the sets of defect candidates for the plural respective images of the inspection region.

8. The defect inspection method according to claim 6, wherein the unifying step unifies sets of feature quantities of the defect candidates extracted for the plural respective images of the inspection region.

9. A defect inspection apparatus comprising:
image acquiring means for acquiring images of a sample whose surface is formed with patterns by sequentially shooting inspection regions including a pattern;
pre-processing means for correcting, as pre-processing, the images taken sequentially by the image acquiring means;
inspection image and reference image generating means for generating inspection images and reference images sequentially from the images corrected by the pre-processing means
defect candidate extracting means for extracting defect candidates on the sample using a set or sets of an inspection image and a reference image generated by the inspection image and reference image generating means;
defect classifying means for classifying defects determined from the defect candidates extracted by the defect candidate extracting means; and
control means for controlling the image acquiring means, the pre-processing means, the inspection image and reference image generating means, the defect candidate extracting means, and the defect classifying means, and for outputting a defect classification result of the defect classifying means, wherein the defect candidate extracting means comprises:
plural computing units;
a parent computing unit for controlling the plural computing units; and
a bidirectional data communication bus that connects the plural computing units and the parent computing unit to each other, the parent computing unit extracting defect candidates on the sample by comparing the inspection image and reference image of the same set by controlling the plural computing units.

10. The defect inspection apparatus according to claim 9, wherein the image acquiring means comprises plural detection optical systems; and wherein the defect candidate extracting means calculates correction values for positioning the inspection image and the reference image of the same set for the plural respective detection optical systems on the basis of images acquired by the plural respective detection optical systems by processing, in parallel, with the plural computing units, images of the same position on the sample acquired by the plural detection optical systems, positions the inspection image and the reference image with respect to each other for the plural respective detection optical systems on the basis of the calculated correction values, calculates feature quantities, of the positioned inspection image and reference image for the plural respective detection optical systems, forms a feature space by unifying sets of feature quantities calculated for the plural respective detection optical systems, finds pixels whose feature quantities are excessively deviated from a distribution in the feature space, and extracts, as defect candidates, the pixels whose feature quantities are excessively deviated from the distribution.

11. The defect inspection apparatus according to claim 9, wherein the defect candidate extracting means positions the inspection image and the reference image of the same set generated by the inspection image and reference image generating means, calculates feature quantities of pairs of corresponding pixels of the positioned inspection image and reference image, finds pixels whose feature quantities are excessively deviated from a distribution of the calculated feature quantities, and extracts, as defect candidates, the pixels whose feature quantities are excessively deviated from the distribution of the calculated feature quantities.

12. The defect inspection apparatus according to claim 11, wherein the feature quantities of pairs of corresponding pixels calculated by the defect candidate extracting means are a combination of plural feature quantities selected from brightness, contrast, a density difference, a brightness variance of nearby pixels, a correlation coefficient, a brightness increase or decrease from nearby pixels, and a second-order differential coefficient.

13. A defect inspection apparatus comprising:
light source means for emitting laser light;
illumination optical system means for illuminating a surface of a sample on which patterns are formed with laser light from a direction that is inclined from the surface of the sample while controlling a polarization state of the laser light emitted from the light source means;
detecting means for separately detecting, via a spatial filter, polarization components of reflection-scattered light coming from the sample being illuminated with the laser light by the illumination optical system means;
signal processing means for detecting defects on the sample by processing detection signals corresponding to the respective polarization components detected separately by the detecting means; and
output means for outputting information of the defects detected by the signal processing means
wherein the signal processing means extracts feature quantities by using the detection signals corresponding to the respective polarization components and detects defects on the sample by detecting deviated points in a feature space which is formed by the feature quantities.

14. The defect inspection apparatus according to claim 13, wherein the signal processing means detects defects on the sample using pieces of information obtained by processing detection signals corresponding to a p-polarized component and an s-polarized component detected separately by the detecting means, respectively, and classifies the detected defects.

15. The defect inspection apparatus according to claim 13, wherein the signal processing means extracts plural defect candidates by processing detection signals corresponding to the respective, separately detected polarization components, compares feature quantities of the extracted plural defect candidates, and detects, as defects, defect candidates whose feature quantities are excessively deviated statistically.

16. The defect inspection apparatus according to claim 13, wherein the illumination optical system means comprises a cylindrical lens, and illuminates an elliptical or line-shaped region of the surface of the sample with the laser light from the direction that is inclined from the surface of the sample via the cylindrical lens.

17. The defect inspection apparatus according to claim 13, wherein the illumination optical system means comprises an optical path switching section capable of switching an azimuth angle and/or an elevation at which the surface of the sample is illuminated with the laser light whose polarization state is controlled.

18. The defect inspection apparatus according to claim 13, wherein the detecting means comprises a first detection optical system section for detecting light that is reflection-scattered from the sample being illuminated with the laser light in a direction of a first elevation with respect to the surface of the sample and a second detection optical system section for detecting light that is reflection-scattered from the sample being illuminated with the laser light in a direction of a second elevation with respect to the surface of the sample.

19. The defect inspection apparatus according to claim 13, wherein the light source means emits pulsed laser light, and wherein the illumination optical system means comprises plural optical paths having different optical path length, and divides each pulse beam of the pulsed laser light emitted form the light source means into plural pulse beams by introducing it to the plural optical paths and illuminates the surface of the sample with the plural pulse beams.

20. A defect inspection method comprising the steps of:
   illuminating a surface of a sample on which patterns are formed from a direction that is inclined from the surface of the sample with laser light that is emitted from a light source and whose polarization state is controlled;
   separately detecting, via a spatial filter, polarization components of reflection-scattered light coming from the sample being illuminated with the laser light;
   detecting defects on the sample by processing detection signals corresponding to the respective, separately detected polarization components; and
   outputting information of the detected defects,
   wherein feature quantities are extracted using the detection signals corresponding to the respective polarization components, and the defects are detected on the sample by detecting deviated points in a feature space which is formed by the feature quantities.

21. The defect inspection method according to claim 20, wherein the defect detecting step detects defects on the sample using pieces of information obtained by processing detection signals corresponding to a p-polarized component and an s-polarized component detected separately, respectively, and classifies the detected defects.

22. The defect inspection method according to claim 20, wherein the defect detecting step extracts plural defect candidates by processing detection signals corresponding to the respective, separately detected polarization components, compares feature quantities of the extracted plural defect candidates, and detects, as defects, defect candidates whose feature quantities are excessively deviated statistically.

23. The defect inspection method according to claim 20, wherein the illuminating step illuminates an elliptical or line-shaped region of the surface of the sample with the laser light that is emitted from the light source and whose polarization state is controlled from the direction that is inclined from the surface of the sample via a cylindrical lens.

24. The defect inspection method according to claim 20, wherein the illuminating step illuminates the surface of the sample with the laser light whose polarization state is controlled while switching an azimuth angle and/or an elevation at which the surface of the sample is illuminated with the laser light.

25. The defect inspection method according to claim 20, wherein the defect detecting step detects defects using a signal obtained by detecting light that is reflection-scattered from the sample being illuminated with the laser light in a direction of a first elevation with respect to the surface of the sample and a signal obtained by detecting light that is reflection-scattered from the sample being illuminated with the laser light in a direction of a second elevation with respect to the surface of the sample.

26. The defect inspection method according to claim 20, wherein the laser light is pulsed laser light, and wherein the illuminating step divides each pulse beam of the pulsed laser light into plural pulse beams by introducing it to plural optical paths having different optical path lengths, and illuminates the surface of the sample with the plural pulse beams.

* * * * *